(12) United States Patent
Fauvarque et al.

(10) Patent No.: US 11,306,063 B2
(45) Date of Patent: Apr. 19, 2022

(54) HETEROCYCLIC NAPHTHOQUINONES DERIVATIVES FOR USE IN THE TREATMENT OF CANCERS INCLUDING CUSHING DISEASE

(71) Applicants: Commissariat a l'Energie Atomique et aux Energies Alternatives, Paris (FR); Universite Grenoble Alpes, St Martin d'Heres (FR); Universite d'Aix Marseille, Marseilles (FR)

(72) Inventors: Marie-Odile Fauvarque, Seyssins (FR); Magda Mortier, Grenoble (FR); Catherine Pillet, Vif (FR); Carmen Aguilar, Grenoble (FR); Emmanuelle Soleilhac, St Etienne de Crossey (FR); Caroline Barette, Sassenage (FR); Vincent Remusat, Marseilles (FR); Thierry Terme, Arles (FR); Patrice Vanelle, Marseilles (FR)

(73) Assignees: Commissariat a l'Energie Atomique et aux Energies Alternatives, Paris (FR); Universite d'Aix Marseille, Marseilles (FR); Universite Grenoble Alpes

(*) Notice: Subject to any disclaimer, the term of this patent is extended or adjusted under 35 U.S.C. 154(b) by 489 days.

(21) Appl. No.: 16/323,691

(22) PCT Filed: Aug. 7, 2017

(86) PCT No.: PCT/EP2017/069919
§ 371 (c)(1),
(2) Date: Feb. 6, 2019

(87) PCT Pub. No.: WO2018/029137
PCT Pub. Date: Feb. 15, 2018

(65) Prior Publication Data
US 2019/0169136 A1    Jun. 6, 2019

(30) Foreign Application Priority Data

Aug. 8, 2016  (EP) .................................. 16306033

(51) Int. Cl.
| | | |
|---|---|---|
| *C07D 263/62* | (2006.01) | |
| *C07D 241/38* | (2006.01) | |
| *A61P 35/00* | (2006.01) | |
| *A61K 31/498* | (2006.01) | |
| *A61K 31/423* | (2006.01) | |
| *C07D 241/52* | (2006.01) | |
| *C07D 263/60* | (2006.01) | |
| *C07D 403/14* | (2006.01) | |
| *C07D 221/06* | (2006.01) | |
| *C07D 263/52* | (2006.01) | |

(52) U.S. Cl.
CPC ............ *C07D 241/52* (2013.01); *A61P 35/00* (2018.01); *C07D 221/06* (2013.01); *C07D 241/38* (2013.01); *C07D 263/52* (2013.01); *C07D 263/60* (2013.01); *C07D 263/62* (2013.01); *C07D 403/14* (2013.01)

(58) Field of Classification Search
CPC ..... A61K 31/498; A61K 31/423; A61P 35/00; C07D 263/62; C07D 241/38
See application file for complete search history.

(56) References Cited

FOREIGN PATENT DOCUMENTS

| WO | 2005/016000 A1 | 2/2005 |
|---|---|---|
| WO | 2011/137320 A2 | 11/2011 |

OTHER PUBLICATIONS

PubChem CID 11230523—National Center for Biotechnology Information. PubChem Compound Summary for CID 11230523, 2-Isobutenylnaphtho[2,3-d]oxazole-4,9-dione. https://pubchem.ncbi.nlm.nih.gov/compound/2-Isobutenylnaphtho_2_3-d_oxazole-4_9-dione. Accessed May 25, 2021, create date Oct. 26, 2006. (Year: 2006).*
Golub et al., Science, vol. 286, Oct. 15, 1999, pp. 531-537. (Year: 1999).*
International Search Report issued in corresponding International Patent Application No. PCT/EP2017/069919 dated Sep. 28, 2017.
Giorgi-Renault et al., "Heterocyclic quinones. VI: synthesis and antitumoral effects of 5,10-benzol[g]quinoxalinediones and aza-analogues," European Journal of Medicinal Chemistry, 20: 144-148 (1985).
Remusat et al., "Synthesis of Original Benzo[g]quinoxaline-5,10-diones by Bis-Srn1 Methodology," Journal of Heterocyclic Chemistry, 41: 221-225 (2004).
Lee et al., "Synthesis and In Vitro Cytotoxicity of 3- or 4-Dialkylaminomethyl-1-azaanthraquinones," Archives of Pharmacal Research, 21: 749-752 (1998).
Rathelot et al., "Synthesis of 3-Alkenyl-1-azaanthraquinones via Diels-Alder and Electron Transfer Reactions," Molecules, 7: 917-921 (2002).
Rathelot et al., "Preparation of 2-Substituted Naphth[2,3-d]Oxazole-4-9-Diones via a Radical Chain Process," Heterocycles Communication, 53:1075-1084 (2000).
Written Opinion issued in corresponding International Patent Application No. PCT/EP2017/069919 dated Sep. 28, 2017.

* cited by examiner

*Primary Examiner* — Laura L Stockton
(74) *Attorney, Agent, or Firm* — Morgan, Lewis & Bockius LLP

(57) ABSTRACT

The present invention concerns heterocyclic naphthoquinones derivatives for use in the treatment of Cushing disease and other cancers, in particular via the inhibition of Ubiquitin Specific Proteases (USP) 8 and/or 2.

12 Claims, 13 Drawing Sheets

FIGURE 1
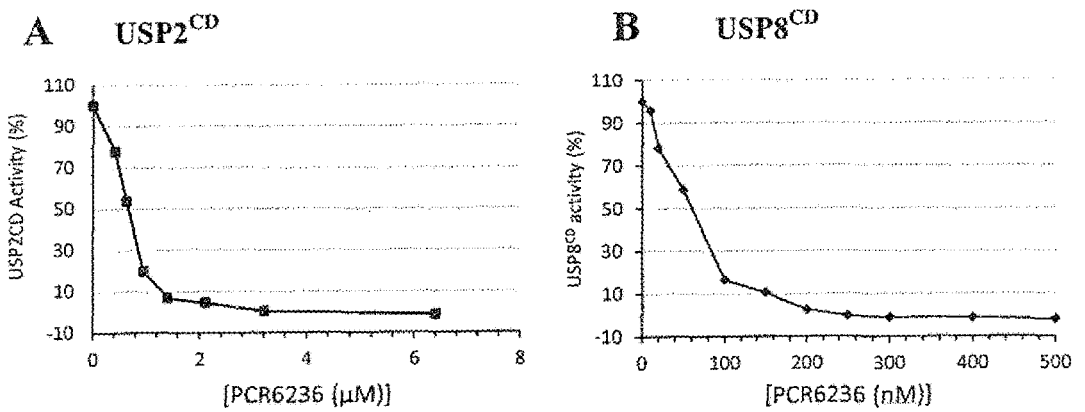
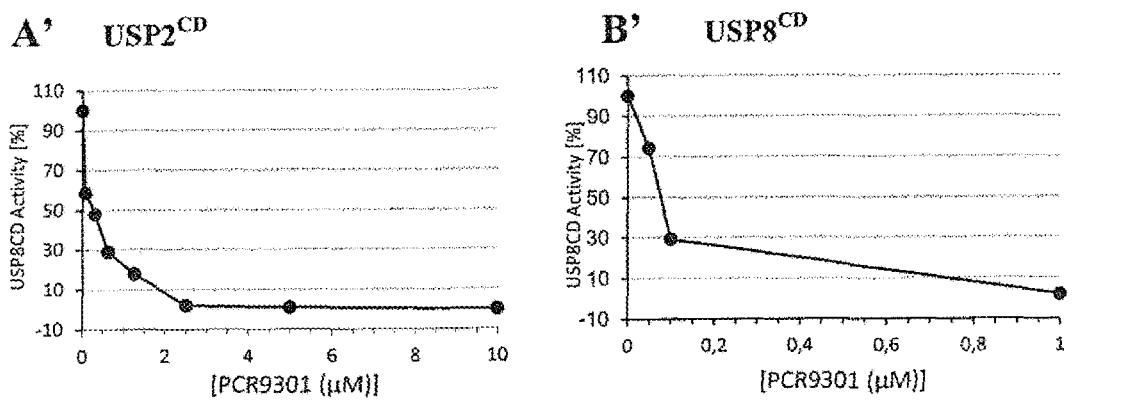
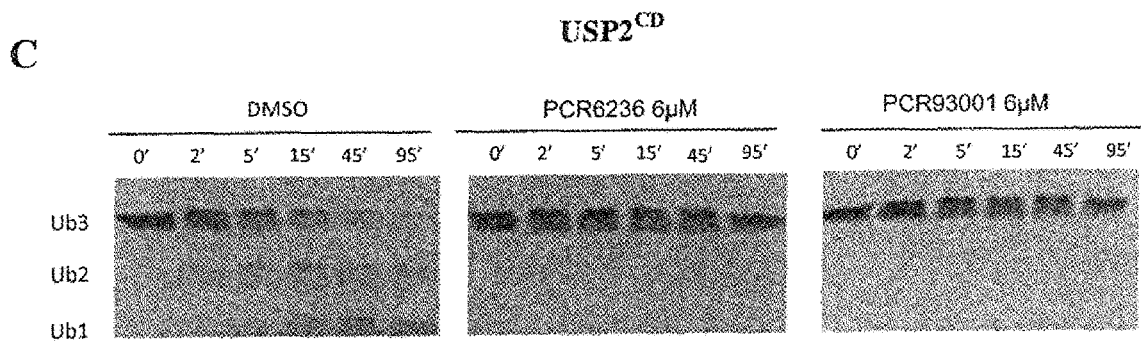
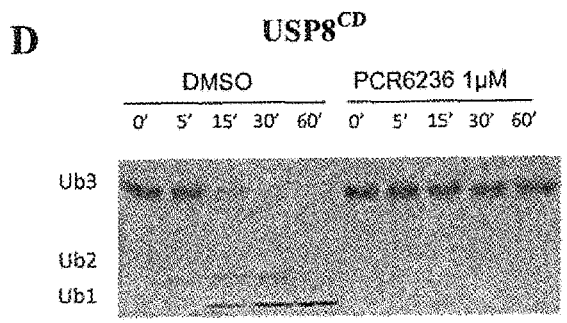

FIGURE 9B
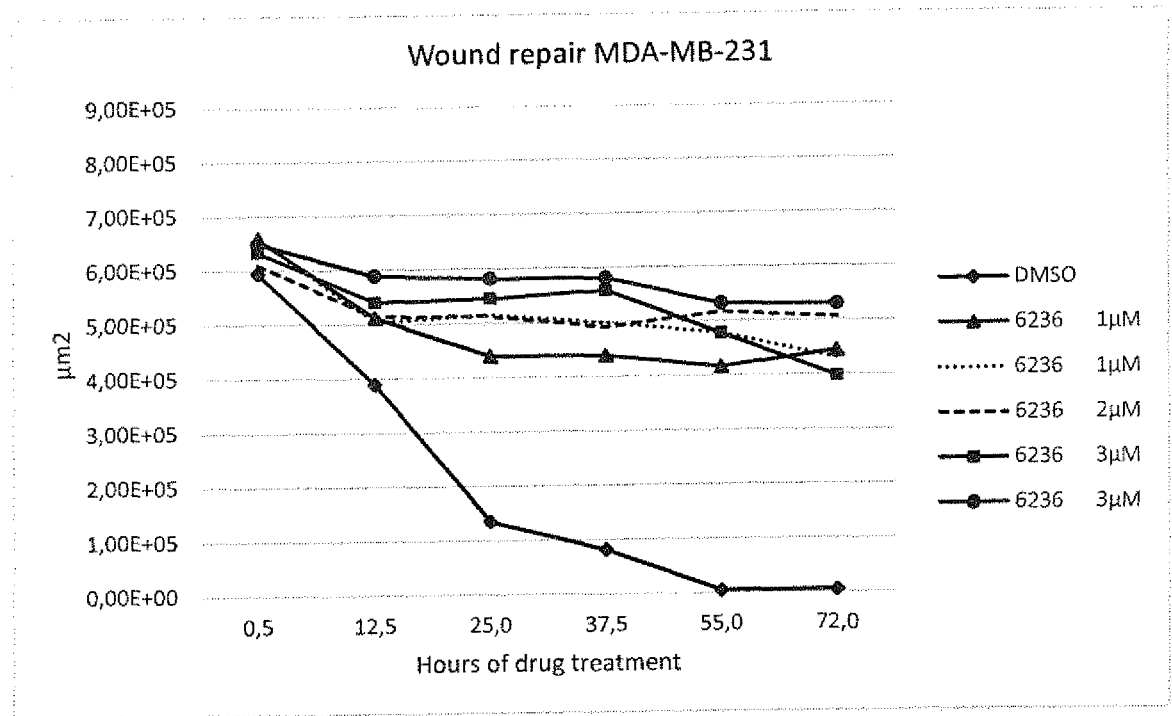
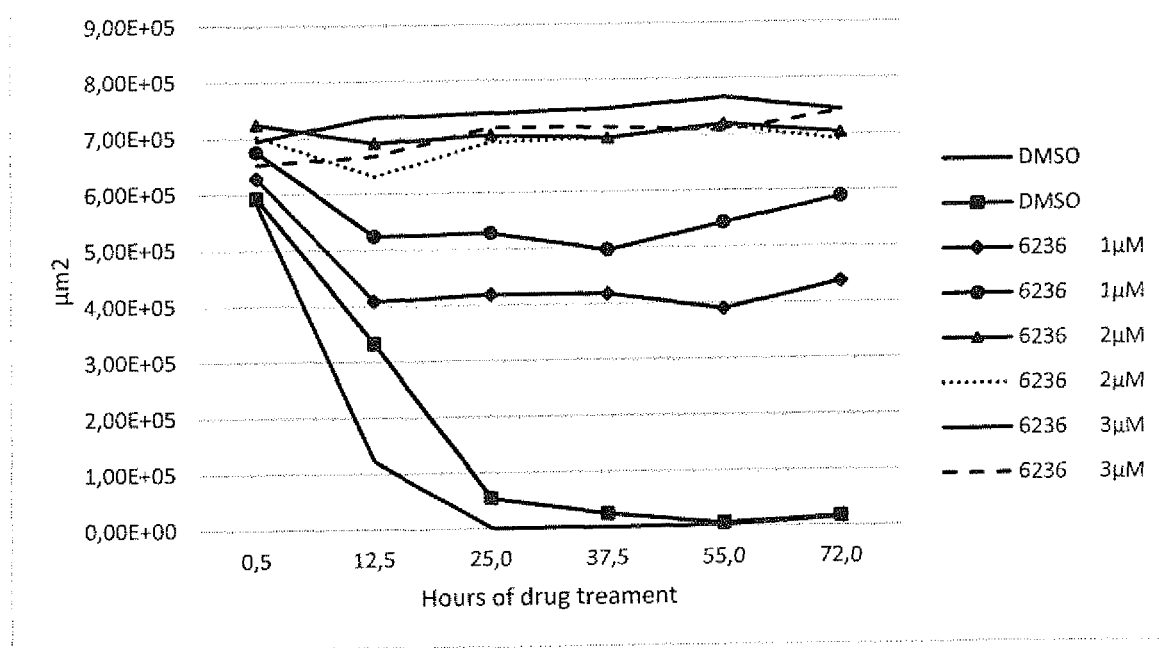

6 hours incubation

FIGURE 12
A HCC827 and H1975
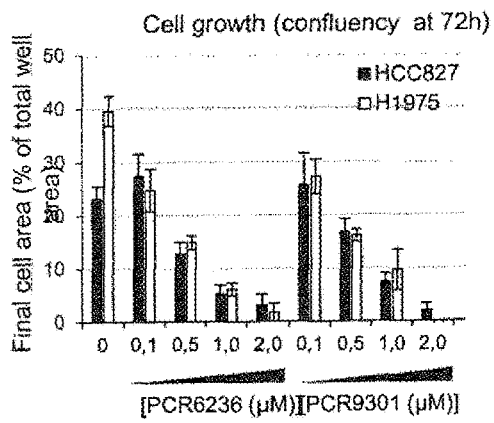
B HCC827 and H1975
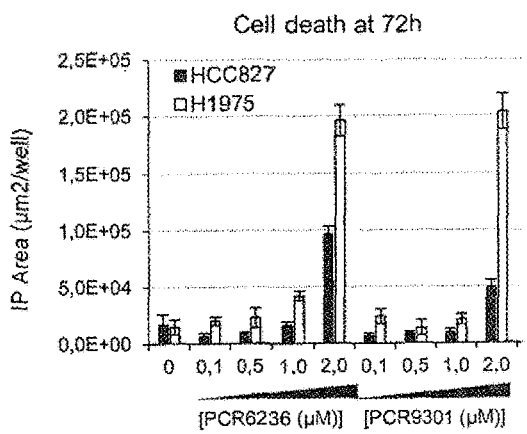
C PC-3
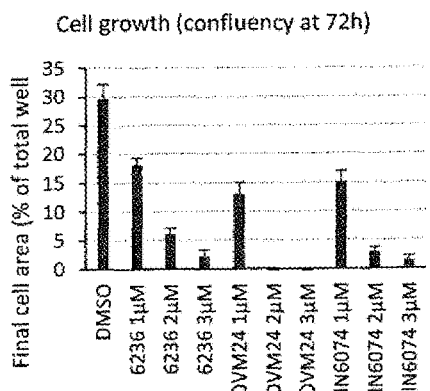
D PC-3
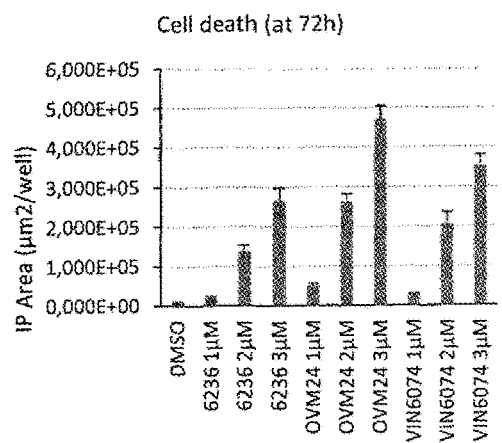
E LNCaP
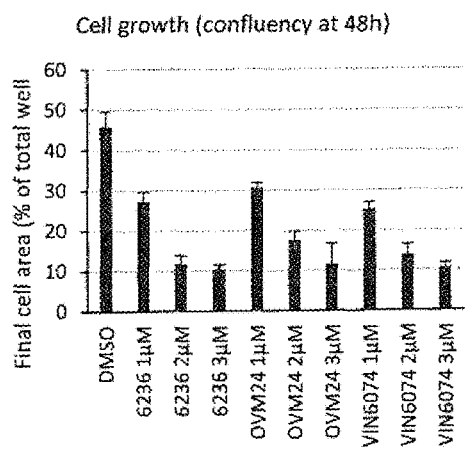
F LNCaP
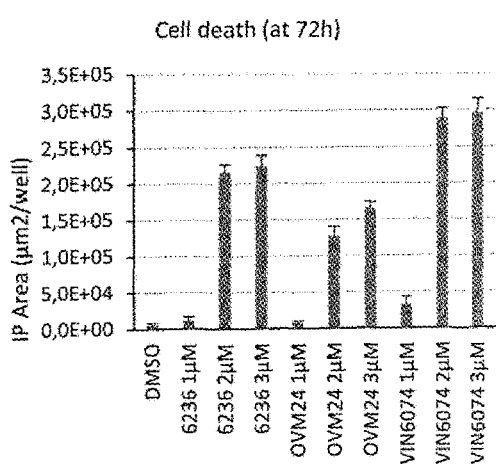

FIGURE 13
A In vitro assay
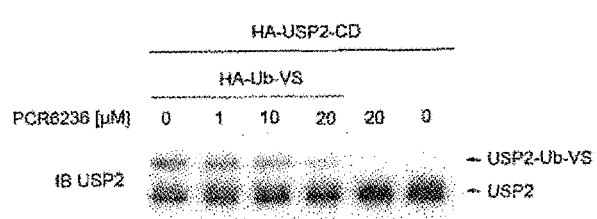
B In vitro assay
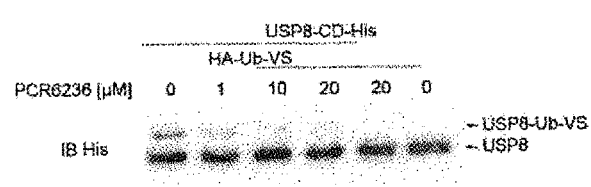
C HEK-293 T whole cell lysate
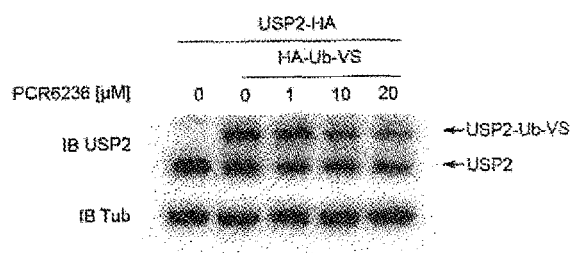
D HEK-293 T whole cell lysate
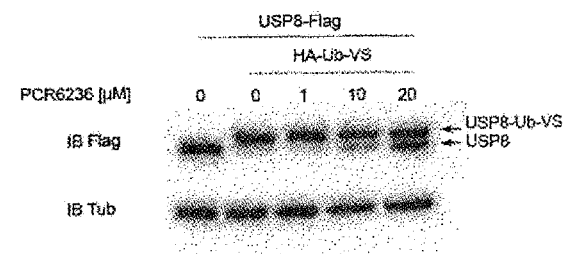

HETEROCYCLIC NAPHTHOQUINONES DERIVATIVES FOR USE IN THE TREATMENT OF CANCERS INCLUDING CUSHING DISEASE

The present invention concerns heterocyclic naphthoquinones derivatives for use in the treatment of Cushing disease and other cancers, in particular via the inhibition of Ubiquitin Specific Proteases (USP) 8 and/or 2.

Ubiquitination is an essential mechanism for the regulation of protein activity or stability in eukaryotes consisting in the reversible chemical linkage of monomers and polymers of ubiquitin polypeptide to lysine residues within target proteins. Ubiquitin contains itself several lysine residues allowing for the formation of different ubiquitin polymerized chains. While the linkage of lysine-48 ubiquitin polymers ($Ub^{K48}$) drives proteins to proteasomal dependent degradation, other ubiquitin moieties, such as linear, $Ub^{K63}$, or ubiquitin monomers regulate protein activity or protein-protein interaction in a plethora of cellular processes such as cell trafficking, endocytosis, signal transduction or DNA repair. Linkage of ubiquitin moieties depends on the successive action of E1, E2, E3 ubiquitin conjugating enzymes and ligases while ubiquitin proteases, also known as deubiquitinases (DUBs), catalyse the reverse reaction. DUBs contain a catalytic domain that has sequence similarity within subfamilies and structural similarity across subfamilies, and unrelated flanking sequences that presumably serve as substrate or regulatory partners binding domains.

Mammalian genomes contain about one hundred DUBs divided in 5 subfamilies among which the Ubiquitin Specific Proteases (USP) subfamily represents the major class in human genome. Importantly, the number of DUBs mutations found to be associated with human pathologies like inflammatory diseases (CYLD, A20, . . . ), cancers (USP2, USP7/HAUSP, USP8, A20, CYLD, . . . ) and neurodegenerative disorders (UCH-L1, MJD, . . . ) is rapidly increasing. The power of the ubiquitin system for therapeutic benefit was first evidenced with the approval in 2003 by the Federal Drug Administration in the United State of the proteasome inhibitor Bortezomib for clinical use (B cell lymphoma, myeloma). However, more specific effects may be reached by targeting DUBs enzymatic activity, a strategy which is in its infancy inside the scientific community with only a few molecules inhibiting DUB activity published or patented to date (Ritorto et al. (2014), *Nature communications* 5, 4763; D'Arcy et al., (2015), *Pharmacology & therapeutics* 147, 32-54, Ndubaku et al. (2015), *Journal of medicinal chemistry* 58, 1581-1595).

Mammalian Usp2 gene encodes three isoforms (USP2a, USP2b, UBP-41) that are expressed in many adult and embryonic tissues and display distinct properties. The USP2a major isoform has a clear oncogenic role in many cellular systems. In prostate cancer cells, overexpressed USP2a protects cancer cells from apoptosis and favours their growth and survival by stabilizing the fatty acid synthase (FAS) which has been associated with the malignancy of some aggressive prostate cancers. At the molecular level, USP2a deubiquitinates and stabilizes oncogenic proteins including Cyclin D1 in HEK293 and HCT116 cells, Cyclin A1 in bladder cancer cells and the two ubiquitin ligases MDM2 and MDMx in various tumour derived cell lines (H1299, testicular embryonal carcinoma and MCF7 breast cancer cells, . . . ), therefore indirectly favouring the destabilization of the tumor suppressor p53 and the subsequent stabilization of the Myc oncogene as shown in prostatic cancer cells. In addition, recent studies show that USP2 also alters the chemotherapeutic response via modulating redox homeostasis (Benassi et al. (2013), *Cell death & disease* 4, e812) and that overexpression of USP2a is a biomarker associated with poor prognosis and enhanced invasiveness of the triple negative aggressive subtype of breast cancer cells (Qu et al. (2015), *Tumour biology: the journal of the International Society for Oncodevelopmental Biology and Medicine* 36, 5415-23). Indeed, partial silencing of USP2 in the highly invasive breast cancer cells MDA-MB-231 cells reduced their migratory capacity in a Transwell® migration assay.

USP8 (also known as UBPY) is a cysteine protease that belongs to the ubiquitin-specific protease family. USP8 appears to be recruited to EGFR-containing early endosomes upon stimulation of the receptor by EGF (Epidermal Growth Factor). USP8 protects EGFR from degradation and might be notably required for the removal of ubiquitin from EGFR prior to incorporation into multivesicular bodies (MVBs). The analysis of tumour DNA samples from patients diagnosed with pituitary adenomas, including Cushing's disease, showed that USP8 is mutated in 30% of the cases (Ma et al. (2015), *Cell research* 25, 306-317, Reincke et al. (2015), *Nature genetics* 47, 31-38). Identified mutations in USP8 are found in a region upstream of the catalytic domain spanning residues 713 and 720 resulting in mutated USP8 exhibiting higher catalytic activity toward ubiquitinated EGFR. In Cushing's disease, the most recurrent mutation on USP8 affects the serine residue S718 that is either mutated or deleted and/or the proline residue P720. These mutations are heterozygous and reduce the ability of USP8 to bind the 14-3-3 proteins, a conserved family of regulatory proteins expressed in all eukaryotic cells. As a consequence USP8 mutants show constitutive and dominant deubiquitinating activity. Permanent activation of USP8 in corticotroph adenomas favours EGFR accumulation and recycling back to the plasma membrane (ibid.) resulting in higher ACTH production and secretion compared to wild-type situation. These finding demonstrate that USP8 inhibition is a promising therapeutic strategy in Cushing's disease. USP8 is also a target in lung cancer, in particular for overcoming Gefitinib resistance (Byun et al. (2013), *Clin. Cancer Res.* 19, 3894-3904).

However, very few inhibitors of the UPS system have been disclosed to date. In addition, their biological activity and their selectivity towards the DUBs family is rarely described.

Proliferative diseases and other diseases that depend on deviations of regulation e.g. in signaling and/or metabolic pathways are a very common cause of death in humans and also in other warm-blooded animals.

Accordingly, it is an object of the present invention to provide new potent compounds for the treatment of cancers including Cushing disease, which are pharmacologically advantageous and/or are effective via the inhibition of USP8 and/or USP2.

Compounds of Formula (I) for Use in the Treatment of Cancer, in Particular Cushing Disease Thus, in one aspect, the present invention relates to a compound of following formula (I) for its use in the treatment of cancer:

(I)

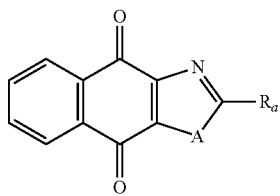

wherein:
A is selected from the group comprising:

(A$_1$)

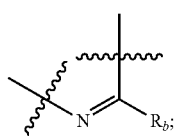

(A$_2$)

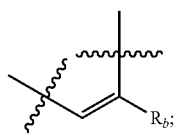

(A$_3$)

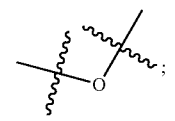

R$_a$ and R$_b$ each independently represent:
  when A is A$_1$ or A$_3$, a group of one of the following formulae:

(R$_{ab1}$)

(R$_{ab2}$)

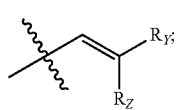

when A is A$_2$, H or a group of one of the following formulae:

(R$_{ab1}$)

(R$_{ab2}$)

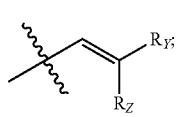

provided that at least one of R$_a$ and R$_b$ is not H;
R$_Y$ and R$_Z$ each independently represent H, a C$_1$-C$_{10}$ linear or branched alkyl group, a C$_3$-C$_{10}$ cycloalkyl group, or together form with the carbon atom to which they are attached a C$_3$-C$_{10}$ cycloalkyl group;

X represents an halogen or a group of the following formula X$_1$:

(X$_1$)

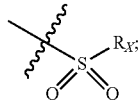

R$_X$ represents a C$_1$-C$_{10}$ linear or branched alkyl group, a C$_3$-C$_{10}$ cycloalkyl group, an aryl group, in particular a phenyl or naphtyl group, a C$_5$-C$_{10}$-membered heteroaryl, in particular a thiophenyl or an indolyl;
said C$_1$-C$_{10}$ linear or branched alkyl group, and/or C$_3$-C$_{10}$ cycloalkyl group being optionally substituted by at least one group selected from:
  a C$_3$-C$_{10}$ cycloalkyl group;
  a phenyl optionally substituted by at least one group selected from a C$_1$-C$_{10}$ linear or branched alkyl group, a C$_3$-C$_{10}$ cycloalkyl group, an halogen, a —OR$_{ii}$ group, an amine of formula —NR$_{ii}$'R$_{ii}$", a nitrile or a nitro group;
  a —OR$_i$ group;
  an amine of formula —NR$_i$'R$_i$";
said aryl and/or C$_5$-C$_{10}$-membered heteroaryl being optionally substituted by at least one group selected from:
  a C$_1$-C$_{10}$ linear or branched alkyl group;
  a C$_3$-C$_{10}$ cycloalkyl group;
  a phenyl optionally substituted by at least one group selected from a C$_1$-C$_{10}$ linear or branched alkyl group, a C$_3$-C$_{10}$ cycloalkyl group, an halogen, a —OR$_i$ group, an amine of formula —NR$_{ii}$'R$_{ii}$", a nitrile or a nitro group;
  an halogen, in particular —F;
  a —OR$_i$ group; two adjacent —OR$_i$ groups forming possibly with the two C atoms bearing said —OR$_4$ groups a 1,4-dioxane ring;
  an amine of formula —NR$_i$'R$_i$";
  a nitrile;
  a nitro group;
  a CF$_3$ group;
R$_i$ and R$_{ii}$ each independently represent H, a C$_1$-C$_{10}$ linear or branched alkyl group, a C$_3$-C$_{10}$ cycloalkyl group;
R$_i$' and R$_i$" each independently represent H, a C$_1$-C$_{10}$ linear or branched alkyl group, a C$_3$-C$_{10}$ cycloalkyl group, or together form with the nitrogen atom to which they are attached a C$_4$-C$_7$ heterocycloalkyl group;
R$_i$' and R$_i$" each independently represent H, a C$_1$-C$_{10}$ linear or branched alkyl group, a C$_3$-C$_{10}$ cycloalkyl group, or together form with the nitrogen atom to which they are attached a C$_4$-C$_7$ heterocycloalkyl group.

In particular, the present invention relates to a compound of following formula (I) for its use in the treatment of cancer:

(I)

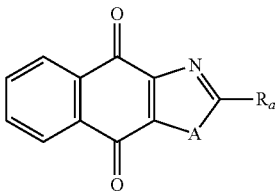

wherein:
A is selected from the group comprising:

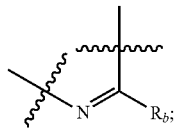

(A₁)

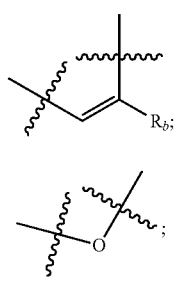

(A₂)

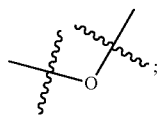

(A₃)

$R_a$ and $R_b$ each independently represent:
when A is $A_1$ or $A_3$, a group of one of the following formulae:

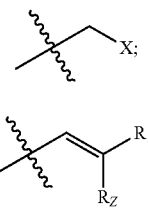 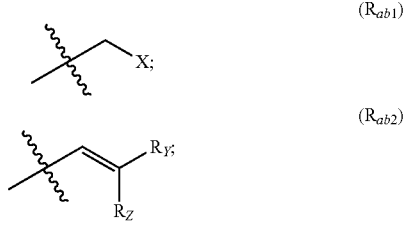

($R_{ab1}$)

($R_{ab2}$)

when A is $A_2$, H or a group of one of the following formulae:

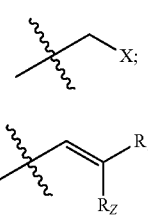 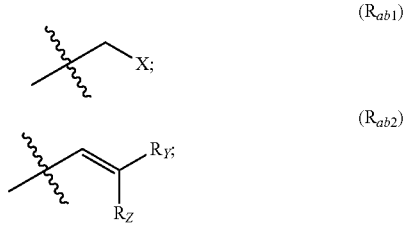

($R_{ab1}$)

($R_{ab2}$)

provided that at least one of $R_a$ and $R_b$ is not H;
$R_Y$ and $R_Z$ each independently represent H, a $C_1$-$C_{10}$ linear or branched alkyl group, a $C_3$-$C_{10}$ cycloalkyl group, or together form with the carbon atom to which they are attached a $C_3$-$C_{10}$ cycloalkyl group;
X represents an halogen or a group of the following formula $X_1$:

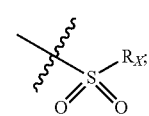

($X_1$)

$R_X$ represents a $C_1$-$C_{10}$ linear or branched alkyl group, a $C_3$-$C_{10}$ cycloalkyl group, a phenyl group, a $C_5$-$C_{10}$-membered heteroaryl, in particular a thiophenyl;
said $C_1$-$C_{10}$ linear or branched alkyl group, and/or $C_3$-$C_{10}$ cycloalkyl group being optionally substituted by at least one group selected from:
a $C_3$-$C_{10}$ cycloalkyl group;
a phenyl optionally substituted by at least one group selected from a $C_1$-$C_{10}$ linear or branched alkyl group, a $C_3$-$C_{10}$ cycloalkyl group, an halogen, a —$OR_{ii}$ group, an amine of formula —$NR_{ii}'R_{ii}''$, a nitrile or a nitro group;
a —$OR_i$ group;
an amine of formula —$NR_i'R_i''$;
said phenyl and/or $C_5$-$C_{10}$-membered heteroaryl being optionally substituted by at least one group selected from:
a $C_1$-$C_{10}$ linear or branched alkyl group;
a $C_3$-$C_{10}$ cycloalkyl group;
a phenyl optionally substituted by at least one group selected from a $C_1$-$C_{10}$ linear or branched alkyl group, a $C_3$-$C_{10}$ cycloalkyl group, an halogen, a —$OR_{ii}$ group, an amine of formula —$NR_{ii}'R_{ii}''$, a nitrile or a nitro group;
an halogen, in particular —F;
a —$OR_i$ group;
an amine of formula —$NR_i'R_i''$;
a nitrile;
a nitro group;
$R_i$ and $R_{ii}$ each independently represent H, a $C_1$-$C_{10}$ linear or branched alkyl group, a $C_3$-$C_{10}$ cycloalkyl group;
$R_i'$ and $R_i''$ each independently represent H, a $C_1$-$C_{10}$ linear or branched alkyl group, a $C_3$-$C_{10}$ cycloalkyl group, or together form with the nitrogen atom to which they are attached a $C_4$-$C_7$ heterocycloalkyl group;
$R_{ii}'$ and $R_{ii}''$ each independently represent H, a $C_1$-$C_{10}$ linear or branched alkyl group, a $C_3$-$C_{10}$ cycloalkyl group, or together form with the nitrogen atom to which they are attached a $C_4$-$C_7$ heterocycloalkyl group.

By "said $C_1$-$C_{10}$ linear or branched alkyl group, and/or $C_3$-$C_{10}$ cycloalkyl group being optionally substituted by" is in particular meant some of the possible meanings of $R_X$, $R_Y$ and/or $R_Z$.

By "said phenyl and/or $C_5$-$C_{10}$-membered heteroaryl being optionally substituted by" is in particular meant others of the possible meanings of $R_X$, $R_Y$ and/or $R_Z$.

In particular, the group A is connected to the rest of the compound of formula (I), via the carbon atoms a and b as follows:

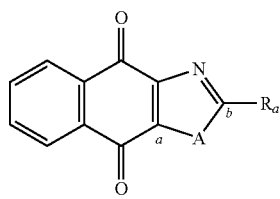

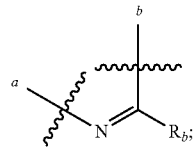

(A₁)

In particular, A is

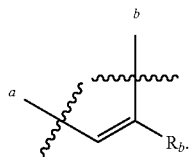
(A₂)

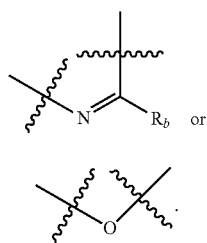
(A₁)

or

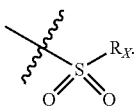
(A₃)

In particular X represents —Cl, or a group of formula

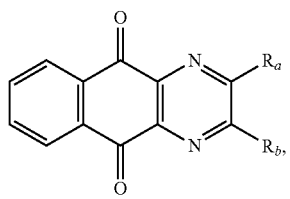
(X₁)

The present invention also relates to a method of treatment of cancer including Cushing's disease comprising the administration of a therapeutically effective amount of a compound of formula (I) to a patient in need thereof.

In a particular embodiment, there are included compounds of formula (I) for use as defined above, of following formula ($I_A$):

($I_A$)

$R_a$ and $R_b$ being as defined above.

In another advantageous embodiment, there are included compounds of formula ($I_A$) for use as defined above, wherein $R_a$ and $R_b$ represent a group of the following formula:

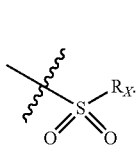
($R_{ab1}$)

In another advantageous embodiment, there are included compounds of formula ($I_A$) for use as defined above, wherein X—Cl, or a group of the following formula:

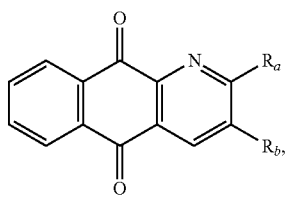
(X₁)

In another advantageous embodiment, there are included compounds of formula (I) or ($I_A$), for use as defined above, wherein $R_a$ and $R_b$ are identical.

In an particular embodiment, there are included compounds of formula (I) for use as defined above, of following formula ($I_B$):

($I_B$)

$R_a$ and $R_b$ being as defined above.

In another advantageous embodiment, there are included compounds of formula ($I_B$) for use as defined above, wherein $R_a$ is H.

In another advantageous embodiment, there are included compounds of formula ($I_B$) for use as defined above, wherein $R_b$ represents a group of the following formula:

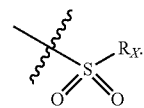
($R_{ab1}$)

In another advantageous embodiment, there are included compounds of formula ($I_B$) for use as defined above, wherein X represents a group of the following formula:

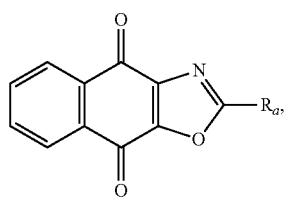
(X₁)

In an particular embodiment, there are included compounds of formula (I) for use as defined above, of following formula ($I_C$):

($I_C$)

$R_a$ being as defined above.

In another advantageous embodiment, there are included compounds of formula ($I_C$) for use as defined above, wherein $R_b$ represents a group of the following formula:

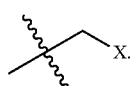

($R_{ab1}$)

In another advantageous embodiment, there are included compounds of formula ($I_C$) for use as defined above, wherein X represents —Cl, or a group of the following formula:

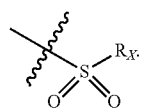

($X_1$)

In a particular embodiment, there are included compounds of formula (I), ($I_A$), ($I_B$) or ($I_C$), for use as defined above, wherein $R_X$ represents a $C_1$-$C_{10}$ linear or branched alkyl group, a $C_3$-$C_{10}$ cycloalkyl group, an aryl, in particular a phenyl, a naphtyl, a $C_5$-$C_{10}$-membered heteroaryl, in particular a thiophenyl or an indolyl;
said $C_1$-$C_{10}$ linear or branched alkyl group, $C_3$-$C_{10}$ cycloalkyl group and $C_5$-$C_{10}$-membered heteroaryl being optionally substituted as defined above;
said aryl or $C_5$-$C_{10}$-membered heteroaryl being optionally substituted by at least one group selected from:
  a $C_1$-$C_{10}$ linear or branched alkyl group;
  a $C_3$-$C_{10}$ cycloalkyl group;
  a phenyl optionally substituted by at least one group selected from a $C_1$-$C_{10}$ linear or branched alkyl group, a $C_3$-$C_{10}$ cycloalkyl group, an halogen, a —$OR_{ii}$ group, an amine of formula —$NR_{ii}'R_{ii}''$, a nitrile or a nitro group;
  —F;
  a —$OR_i$ group; two adjacent —$OR_i$ groups forming possibly with the two C atoms bearing said —$OR_i$ groups a 1,4-dioxane ring;
  an amine of formula —$NR_i'R_i''$;
  a nitrile;
  a nitro group;
  a $CF_3$ group.

In a particular embodiment, there are included compounds of formula (I), ($I_A$), ($I_B$) or ($I_C$), for use as defined above, wherein $R_X$ represents a $C_1$-$C_{10}$ linear or branched alkyl group, a $C_3$-$C_{10}$ cycloalkyl group, a phenyl, a $C_5$-$C_{10}$-membered heteroaryl;
said $C_1$-$C_{10}$ linear or branched alkyl group, $C_3$-$C_{10}$ cycloalkyl group and $C_5$-$C_{10}$-membered heteroaryl being optionally substituted as defined above;
said phenyl being optionally substituted by at least one group selected from:
  a $C_1$-$C_{10}$ linear or branched alkyl group;
  a $C_3$-$C_{10}$ cycloalkyl group;
  a phenyl optionally substituted by at least one group selected from a $C_1$-$C_{10}$ linear or branched alkyl group, a $C_3$-$C_{10}$ cycloalkyl group, an halogen, a —$OR_{ii}$ group, an amine of formula —$NR_{ii}'R_{ii}''$, a nitrile or a nitro group;
  —F;
  a —$OR_i$ group;
  an amine of formula —$NR_i'R_i''$;
  a nitrile;
  a nitro group.

In a more particular embodiment, there are included compounds of formula (I), ($I_A$), ($I_B$) or ($I_C$), for use as defined above, wherein $R_X$ represents a $C_1$-$C_{10}$ linear or branched alkyl group, a $C_3$-$C_{10}$ cycloalkyl group, a phenyl, a naphytl, a thiophenyl, an indolyl; said phenyl, naphtyl, thiophenyl or indolyl being optionally substituted by at least one group selected from:
  a $C_1$-$C_{10}$ linear or branched alkyl group;
  a $C_3$-$C_{10}$ cycloalkyl group;
  —F;
  a —$OR_i$ group; two adjacent —$OR_i$ groups forming possibly with the two C atoms bearing said —$OR_i$ groups a 1,4-dioxane ring;
  a nitro group;
  a $CF_3$ group.

In a more particular embodiment, there are included compounds of formula (I), ($I_A$), ($I_B$) or ($I_C$), for use as defined above, wherein $R_X$ represents a $C_1$-$C_{10}$ linear or branched alkyl group, a $C_3$-$C_{10}$ cycloalkyl group, a phenyl, a thiophenyl;
said phenyl and thiophenyl being optionally substituted by at least one group selected from:
  a $C_1$-$C_{10}$ linear or branched alkyl group;
  a $C_3$-$C_{10}$ cycloalkyl group;
  —F;
  a —$OR_i$ group;
  a nitro group.

In particular embodiment, there are included compounds of formula (I) for use as defined above, wherein said compound is not of the following formula:

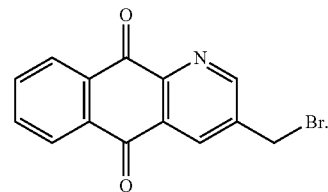 [SMILES: O=C1c2ccccc2C(=O)c2ncc(CBr)cc21]

In particular embodiment, there are included compounds of formula (I) for use as defined above, wherein said compound is not of one of the following formulae:

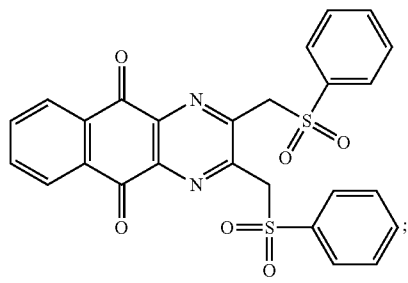

-continued
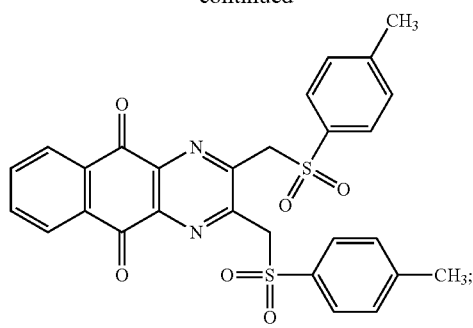
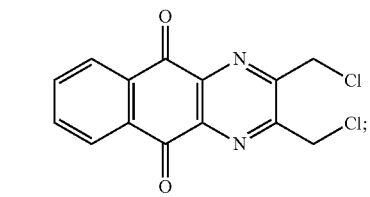
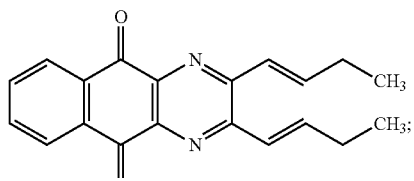
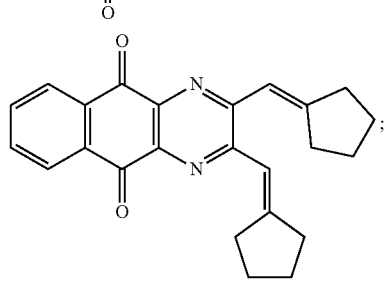
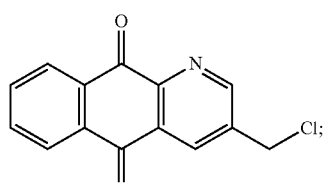
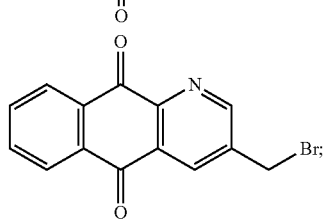
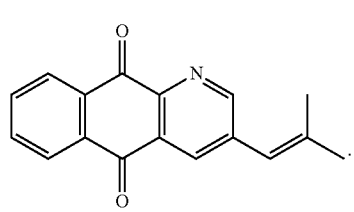 [SMILES: CC(C)=Cc1cnc2c(c1)C(=O)c1ccccc1C2=O ; "."]
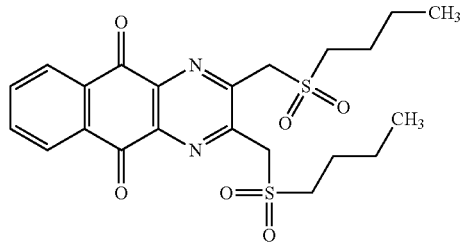
PCR6236
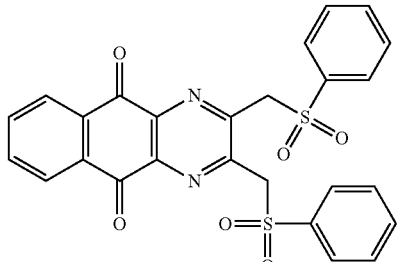
PCR7986
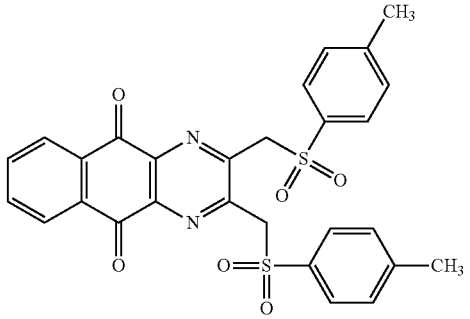
PCR7985
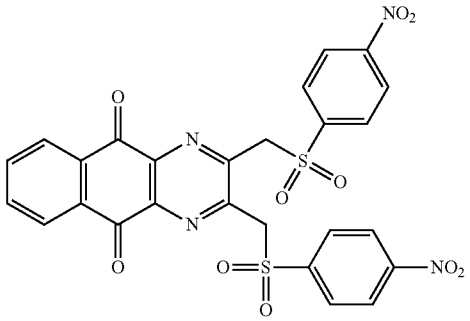
PCR7991
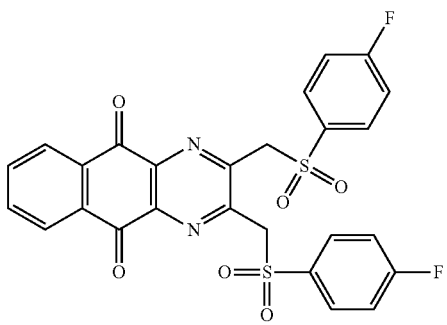
PCR7993
In particular embodiment, there are included compounds of formula (I) for use as defined above, of one of the following formulae:

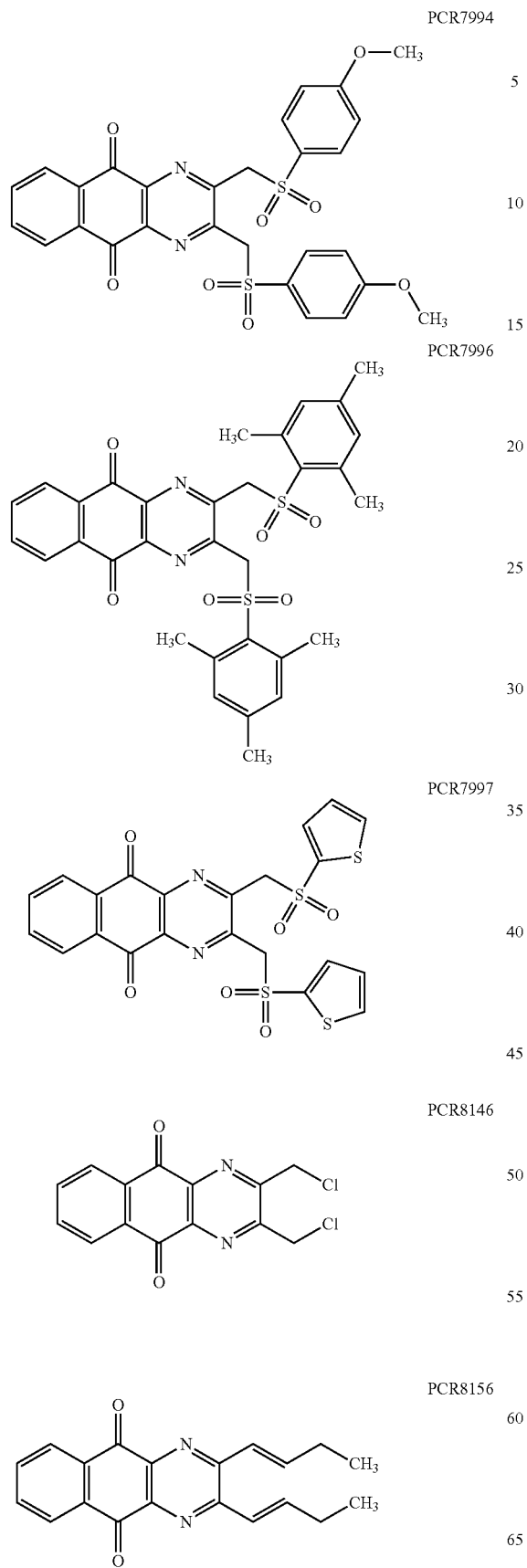
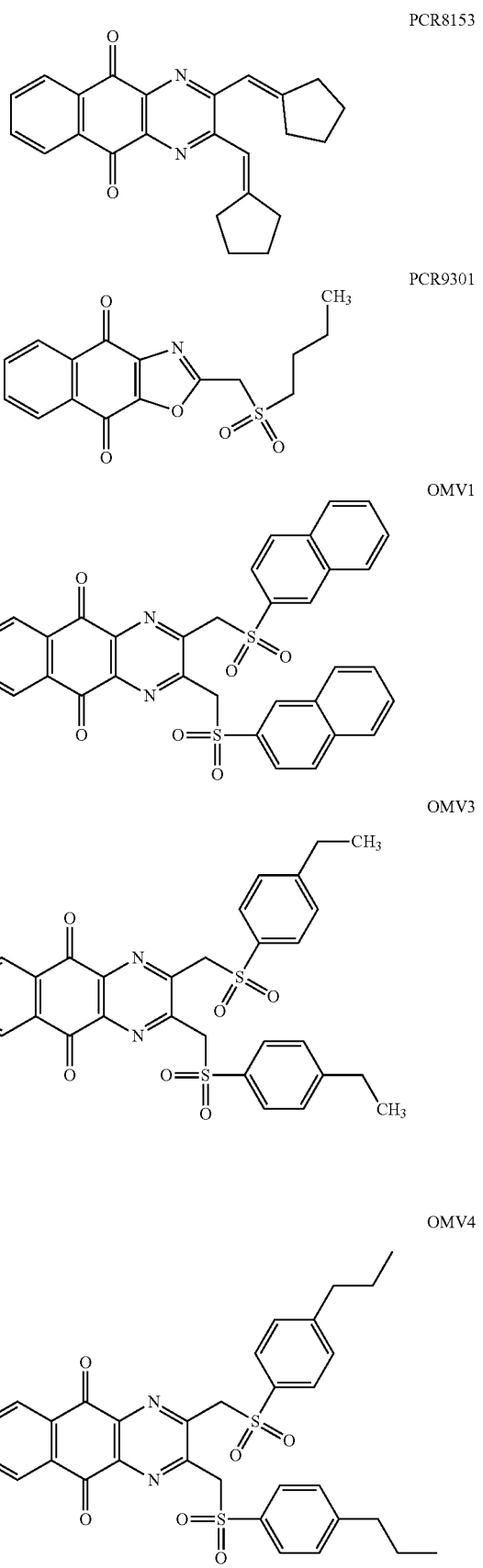

-continued
OMV5
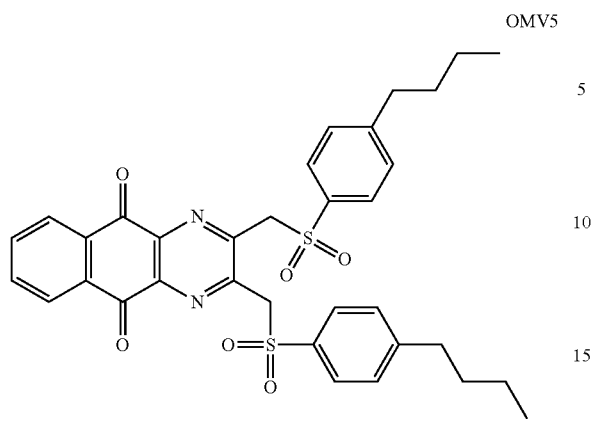
OMV13
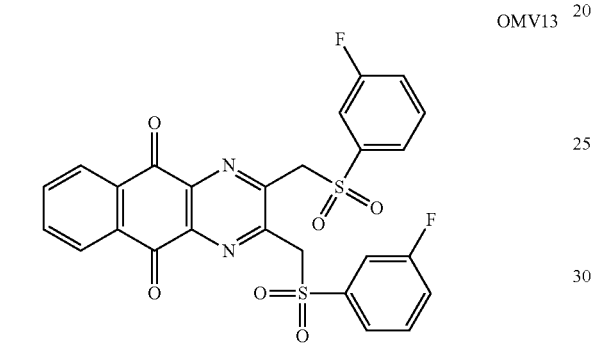
OMV14
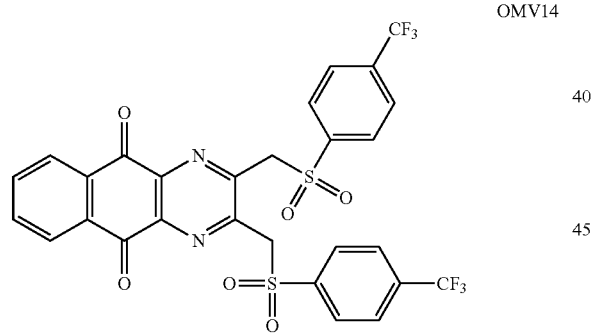
OMV15
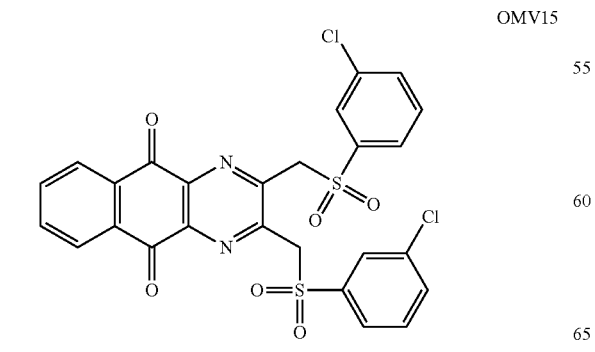
OMV16
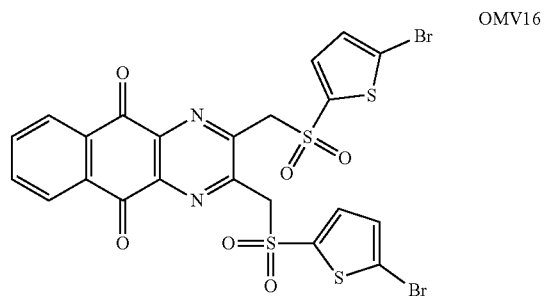
OMV17
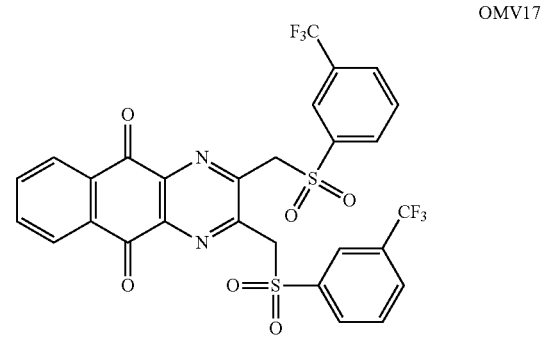
OMV18
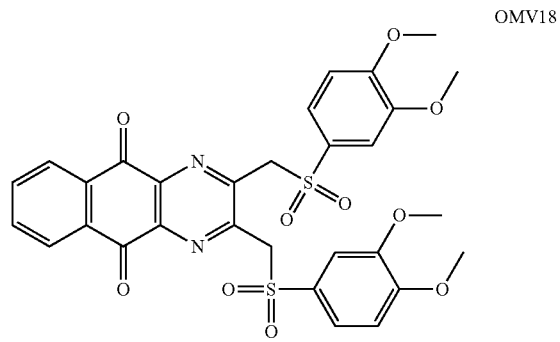
OMV19
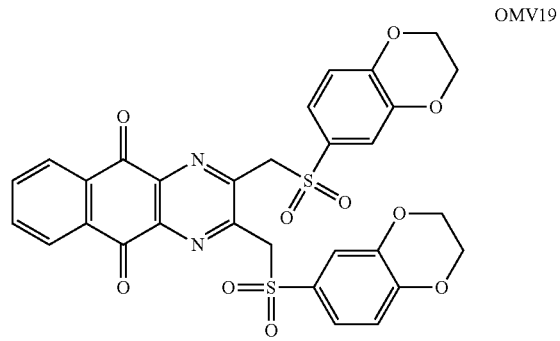
OMV20
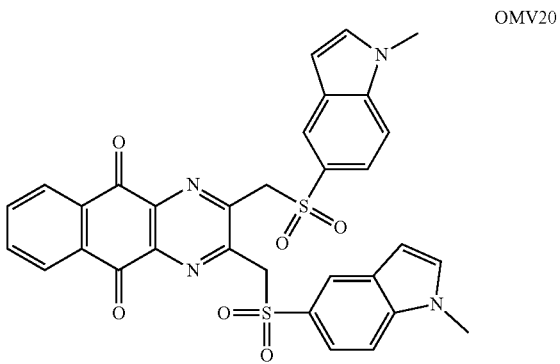

OMV21
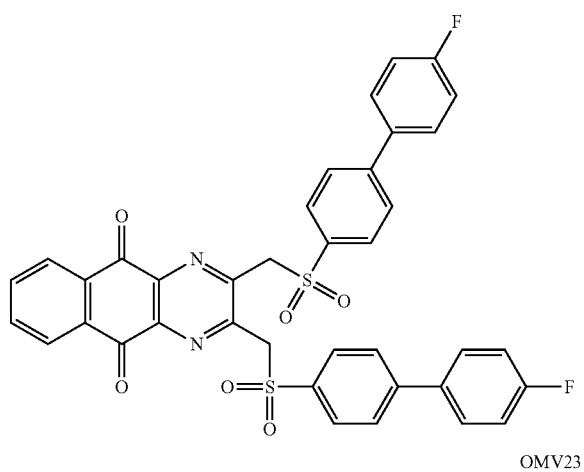

OMV23
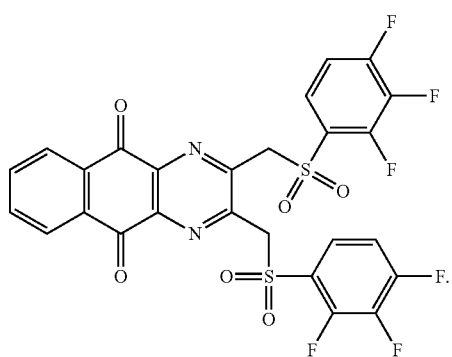

OMV24
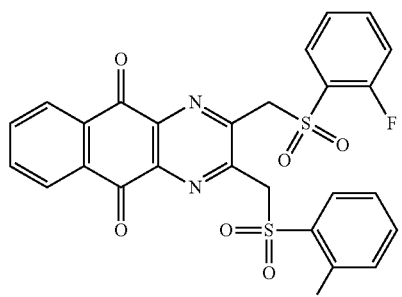

OMV8
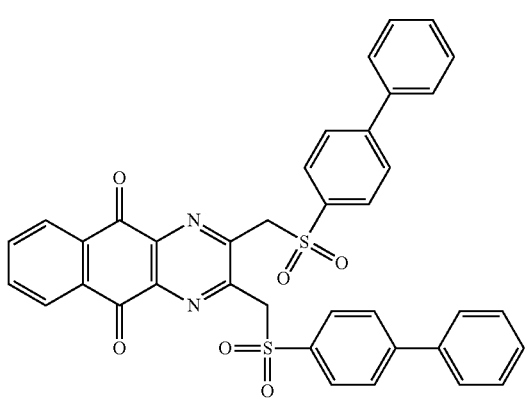

VIN6074
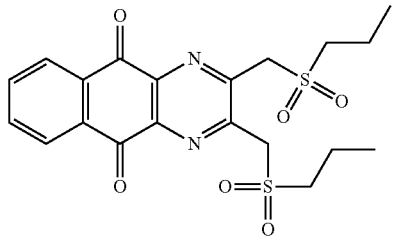

VIN6075
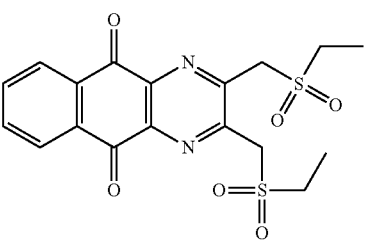

VIN6076
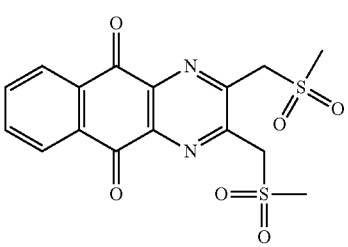

VIN6077
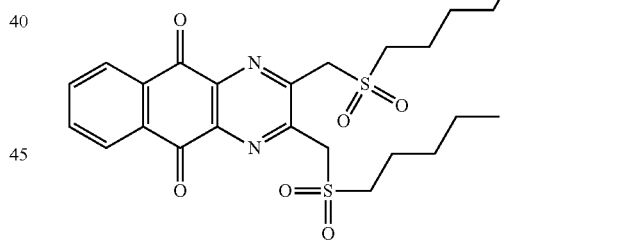

In particular embodiment, there are included compounds of formula (I) for use as defined above, wherein said cancer is selected from the group comprising prostate cancer, bladder cancer, breast cancer, lung cancer, colorectal cancer, pituitary adenomas and Cushing's disease, said cancer being in particular Cushing's disease.

In particular embodiment, there are included compounds of formula (I) for use as defined above, by inhibiting USP8 and/or USP2.

In a more particular embodiment, there are included compounds of formula (I) for use as defined above, by inhibiting USP2, said cancer being in particular selected from the group comprising prostate cancer, bladder cancer and breast cancer.

Compound for its use as defined above, by inhibiting USP2, are in particular of one of the following formulae:

PCR6236
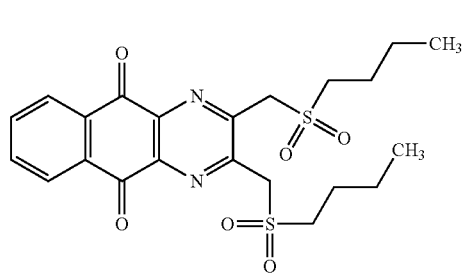 [SMILES: CCCCS(=O)(=O)Cc1nc2c(nc1CS(=O)(=O)CCCC)C(=O)c1ccccc1C2=O]
PCR7986
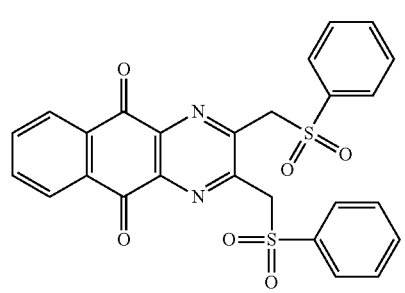 [SMILES: O=C1c2ccccc2C(=O)c2nc(CS(=O)(=O)c3ccccc3)c(CS(=O)(=O)c3ccccc3)nc21]
PCR7991
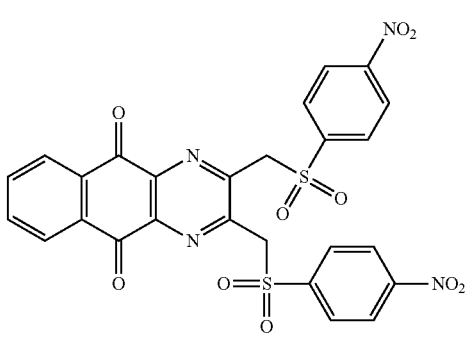
PCR7994
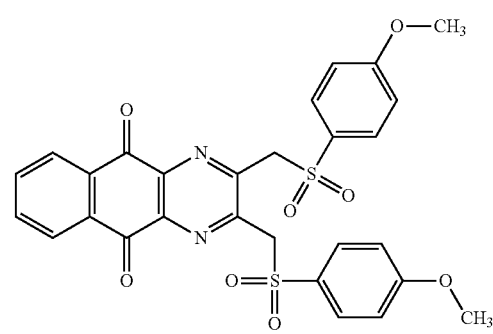
PCR7996
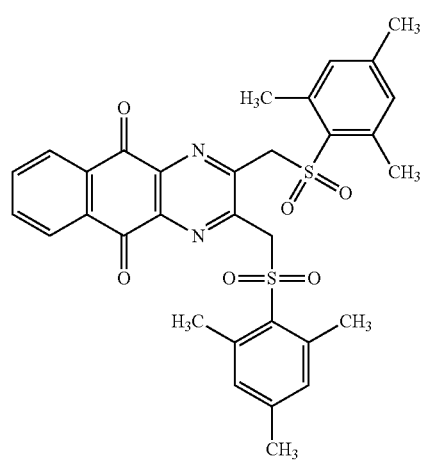
PCR7997
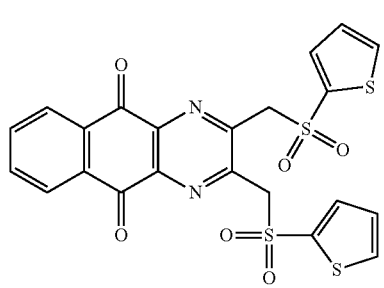
PCR8146
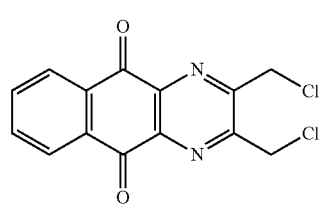
PCR8153
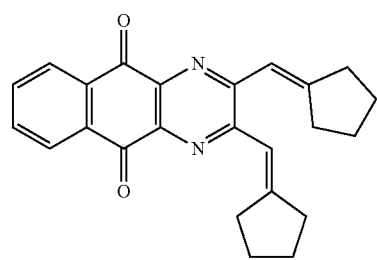
PCR9301
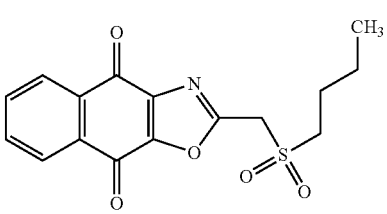

-continued

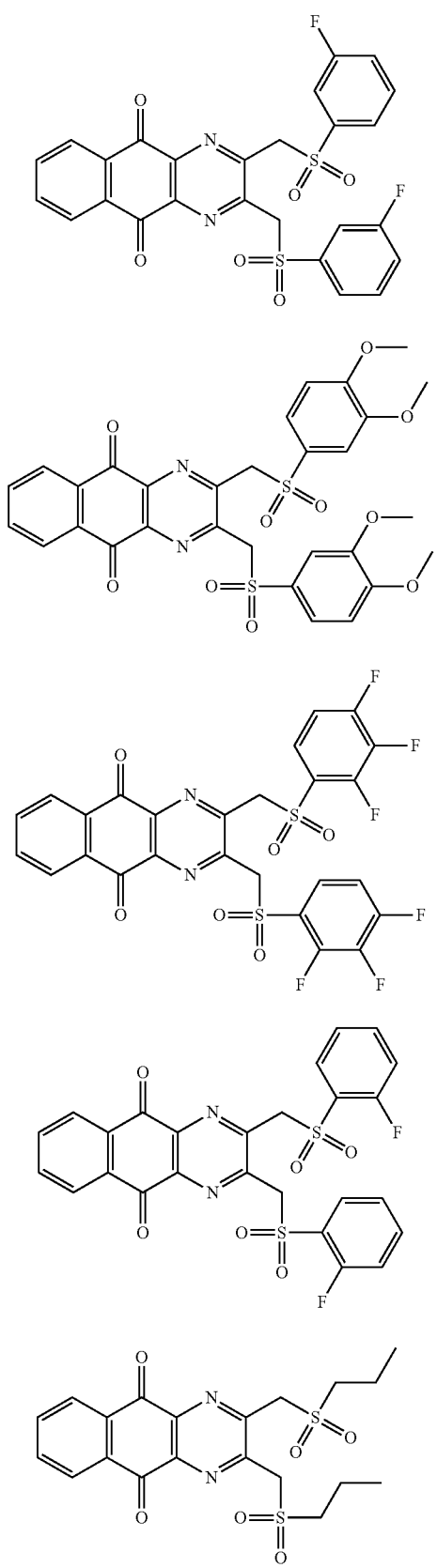

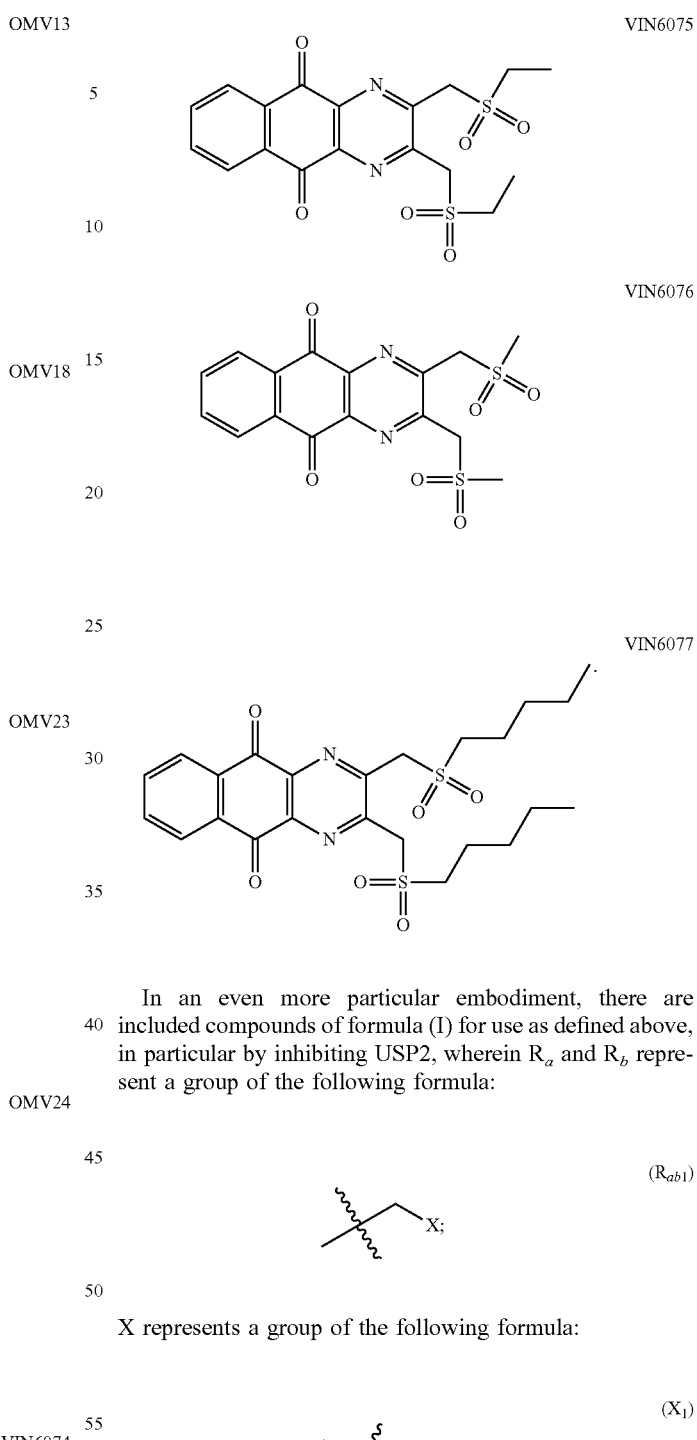

In an even more particular embodiment, there are included compounds of formula (I) for use as defined above, in particular by inhibiting USP2, wherein $R_a$ and $R_b$ represent a group of the following formula:

(R$_{ab1}$)

X represents a group of the following formula:

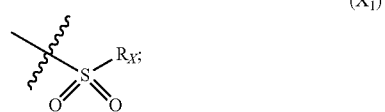

(X$_1$)

$R_X$ represents a phenyl optionally substituted by at least one —$OR_i$ group or by at least two, in particular three, $C_1$-$C_{10}$ linear or branched alkyl groups, A being in particular $A_1$.

Compound for its use as defined above, by inhibiting USP2, are in particular of one of the following formulae:

PCR7986

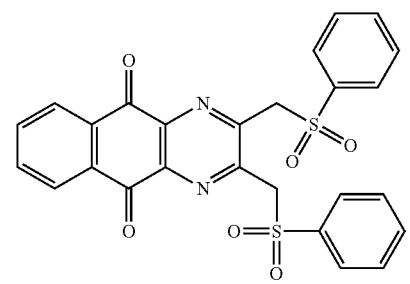

PCR7994

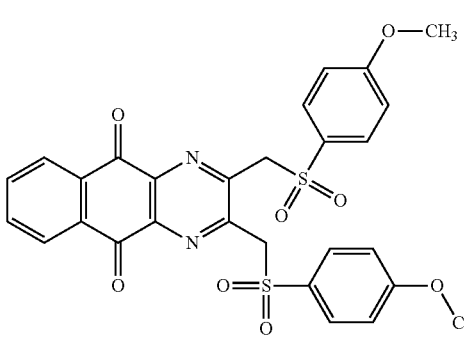

PCR7996

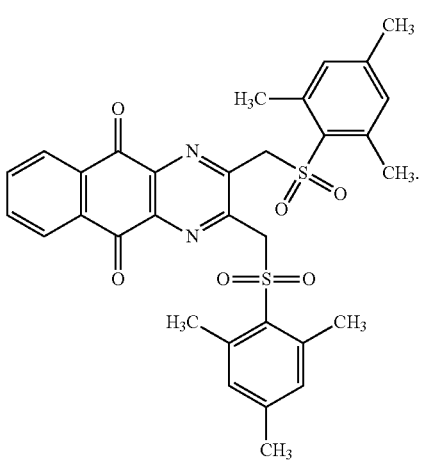

In a particular embodiment, there are included compounds of formula (I) for use as defined above, by inhibiting USP8, said cancer is selected from the group comprising lung cancer, pituitary adenomas and Cushing's disease.

Compound for its use as defined above, by inhibiting USP8, are in particular of one of the following formulae:

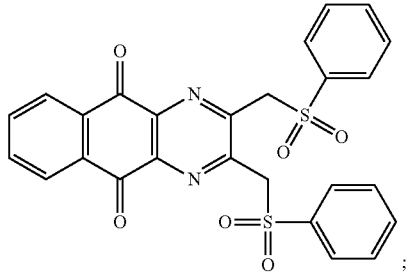

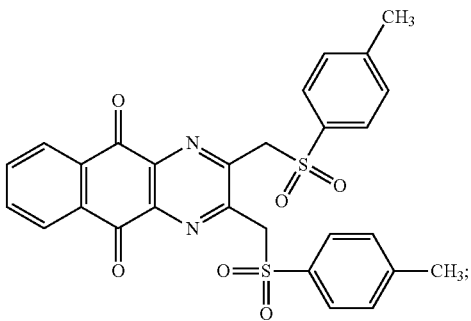

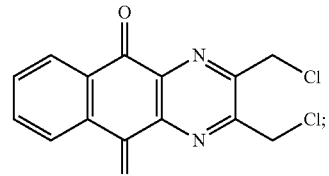

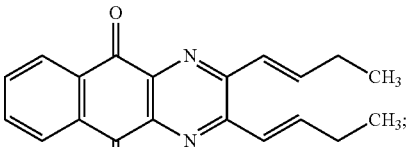

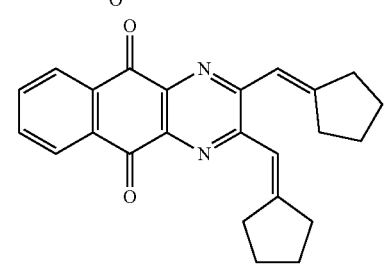

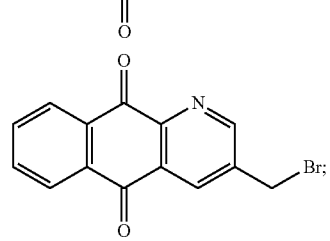

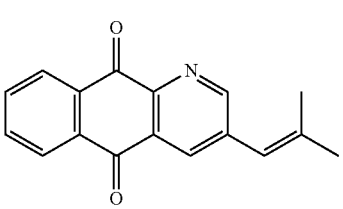

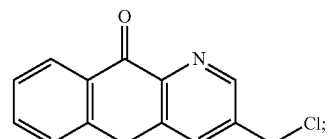

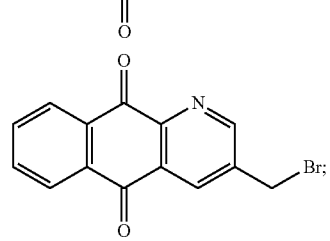

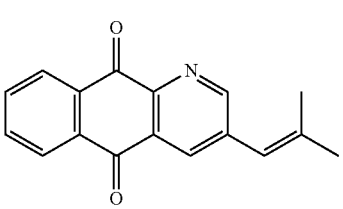

In particular embodiment, there are included compounds of formula (I) for use as defined above, of one of the following formulae:

PCR6236
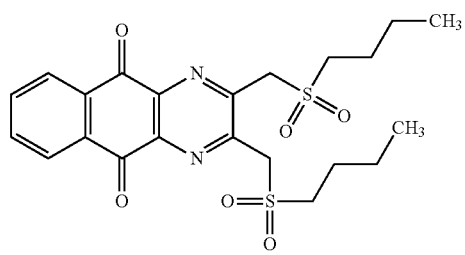
PCR7985
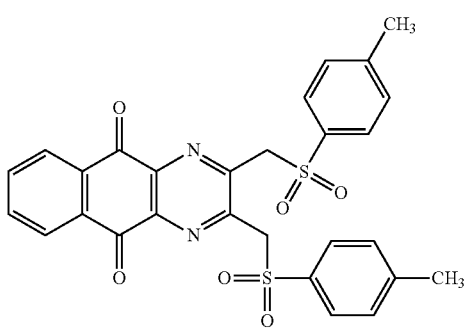 [SMILES: Cc1ccc(S(=O)(=O)Cc2nc3c(nc2CS(=O)(=O)c2ccc(C)cc2)C(=O)c2ccccc2C3=O)cc1]
PCR7991
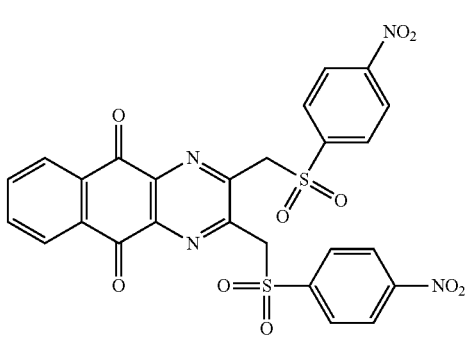 [SMILES: O=C1c2ccccc2C(=O)c2nc(CS(=O)(=O)c3ccc([N+](=O)[O-])cc3)c(CS(=O)(=O)c3ccc([N+](=O)[O-])cc3)nc21]
PCR7993
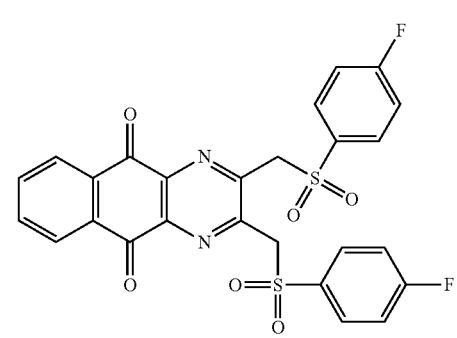 [SMILES: O=C1c2ccccc2C(=O)c2nc(CS(=O)(=O)c3ccc(F)cc3)c(CS(=O)(=O)c3ccc(F)cc3)nc21]
PCR7997
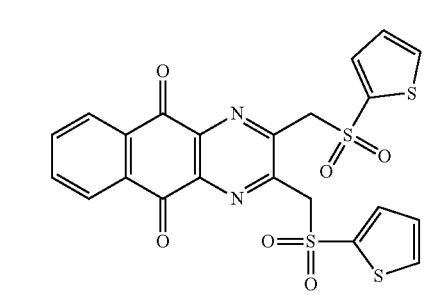
PCR8146
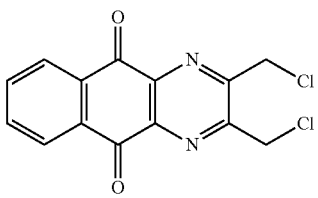
PCR8156
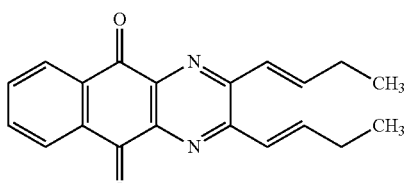
PCR8153
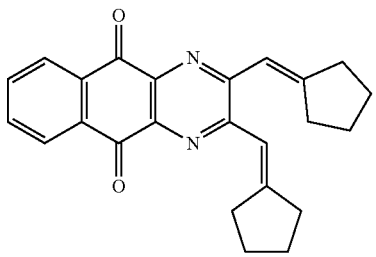
PCR9301
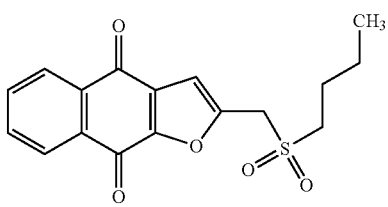
PCR7996
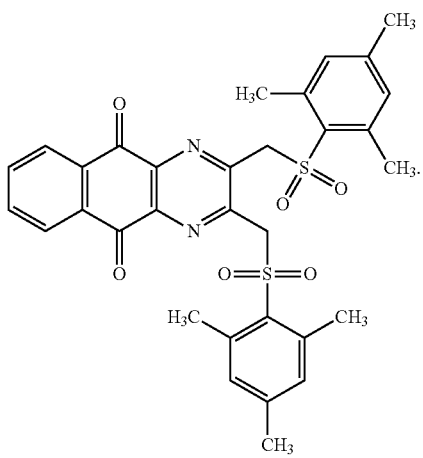
In an even more particular embodiment, there are included compounds of formula (I) for use as defined above, in particular by inhibiting USP8, wherein $R_a$ and $R_b$ represent a group of the following formula:
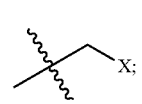
(R$_{ab1}$)

X represents a group of the following formula:

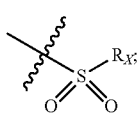

(X₁)

$R_X$ represents a $C_1$-$C_{10}$, in particular $C_4$-$C_5$, linear or branched alkyl group or a phenyl substituted by at least one nitro group and/or at least one —$OR_i$ group, in particular a —OMe, and/or at least one —Cl;
A being in particular $A_1$.

In an even more particular embodiment, there are included compounds of formula (I) for use as defined above, in particular by inhibiting USP8, wherein $R_a$ and $R_b$ represent a group of the following formula:

($R_{ab1}$)

X represents a group of the following formula:

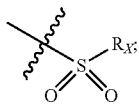

(X₁)

$R_X$ represents a $C_1$-$C_{10}$ linear or branched alkyl group or a phenyl substituted by at least one nitro group,
A being in particular $A_1$.

Compound for its use as defined above, by inhibiting USP8, are in particular of one of the following formulae:

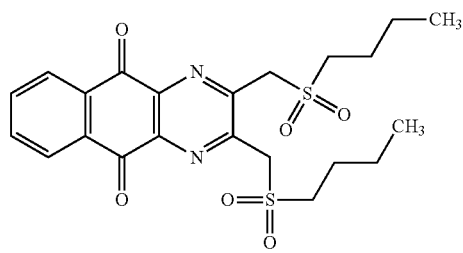

PCR6236

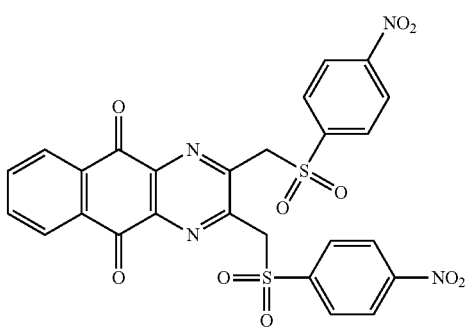

PCR7991

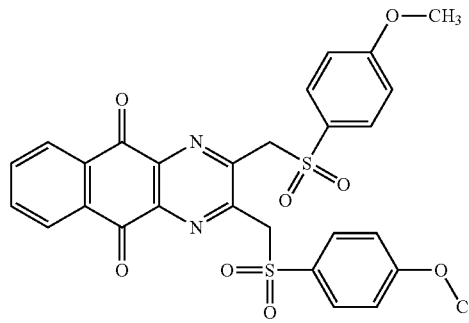

PCR7994

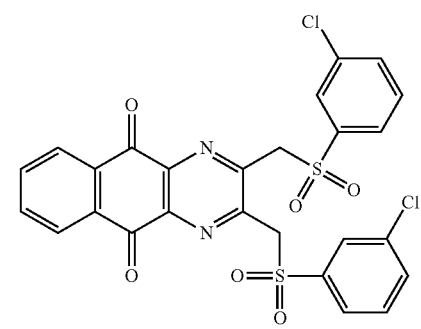

OMV15

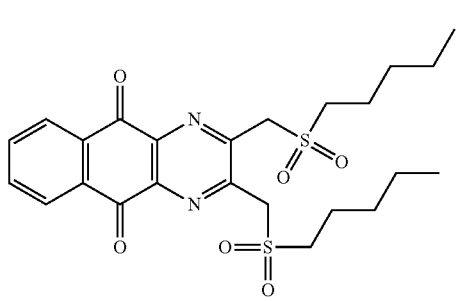

VIN6077

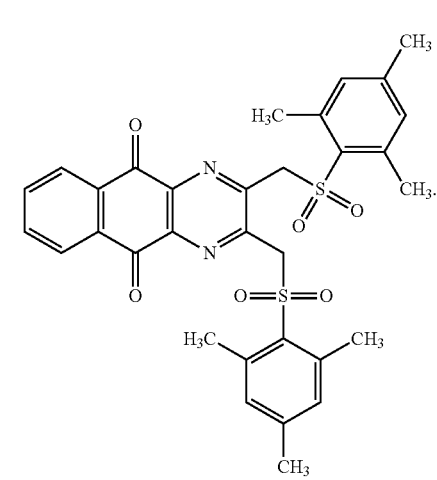

PCR7996

In a particular embodiment, there are included a compound of formula (I) for use as defined above, wherein said compound of formula (I) is administered simultaneously, separately or sequentially with an anti-cancer drug.

The anti-cancer drug is in particular chosen from pro-oxidant agents, more particularly cisplatin (CDDP), doxorubicin (Doxo), taxanes; and Gefitinib.

The compounds of the invention are indeed useful to counteract resistance to chemotherapy, in particular to the anti-cancer drugs defined above.

The present invention also relates to compounds of formula (I) as defined above, as inhibitors of USP8 and/or USP2.

It is to be noted that the present invention includes the combination of all the embodiments listed hereabove for formula (I), ($I_A$), ($I_B$) or ($I_C$).

Pharmaceutical Compositions

In a second aspect, the present invention relates to a pharmaceutical composition comprising
a compound of formula (I) as defined above, or
a stereoisomeric form, a mixture of stereoisomeric forms or
a pharmaceutically acceptable salt form thereof,
in admixture with at least one pharmaceutically acceptable excipient.

In a particular embodiment, the pharmaceutical composition further comprises an anti-cancer drug.

The anti-cancer drug is in particular chosen from pro-oxidant agents, more particularly cisplatin (CDDP), doxorubicin (Doxo), taxanes; and Gefitinib.

It is to be noted that the present invention includes the combination of all the embodiments listed hereabove for formula (I), ($I_A$), ($I_B$) or ($I_C$).

In particular embodiment, there are included compounds of formula (I) for use as defined above, wherein said compound is not of the following formula:

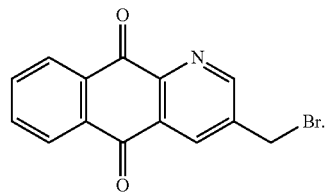

In particular embodiment, there are included pharmaceutical compositions as defined above wherein said compound is not of one of the following formulae:

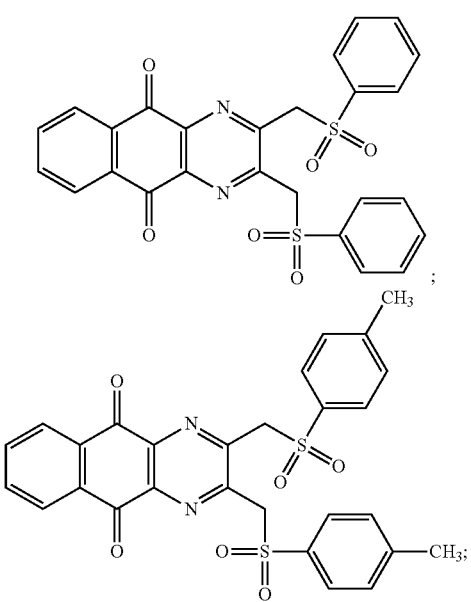

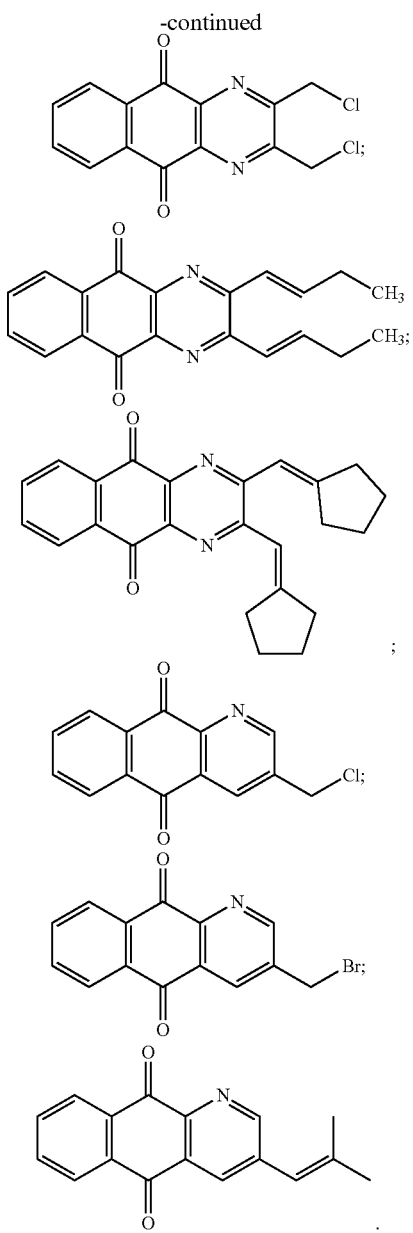

The compounds of formula (I), ($I_A$), ($I_B$) or ($I_C$) of the present invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints or into pituitary gland.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of the present invention, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavouring agents, solubilizers, lubricants, suspending agents, binders, or tablet disintegrating agents; it can also be an encapsulating material.

Tablets, powders, cachets, and capsules can be used as solid dosage forms suitable for oral administration.

Liquid form compositions include solutions, suspensions, and emulsions. For example, sterile water or propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavouring agents, stabilizers, and thickening agents as desired. Aqueous solutions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will according to one embodiment of the present invention include 0.05% to 99% weight (percent by weight), according to an alternative embodiment from 0.10 to 50% weight, of the compound of the present invention, all percentages by weight being based on total composition. A therapeutically effective amount for the practice of the present invention may be determined, by the use of known criteria including the age, weight and response of the individual patient, and interpreted within the context of the disease which is being treated or which is being prevented, by one of ordinary skills in the art.

Compounds of Formula (II)

In a third aspect, the present invention relates to a compound of following formula (II), and the stereoisomeric forms, mixtures of stereoisomeric forms or pharmaceutically acceptable salts forms thereof:

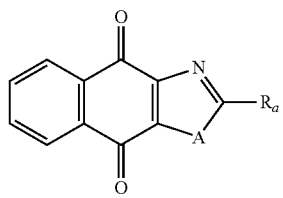

(II)

wherein:

A is selected from the group comprising:

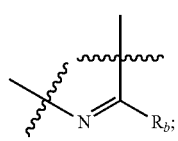

(A$_1$)

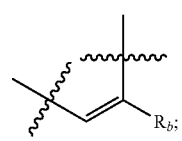

(A$_2$)

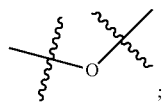

(A$_3$)

$R_a$ and $R_b$ each independently represent:
when A is A$_1$ or A$_3$, a group of one of the following formulae:

(R$_{ab1}$)

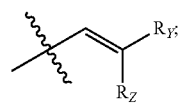

(R$_{ab2}$)

when A is A$_2$, H or a group of one of the following formulae:

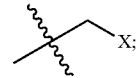

(R$_{ab1}$)

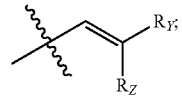

(R$_{ab2}$)

provided that at least one of $R_a$ and $R_b$ is not H;
$R_Y$ and $R_Z$ each independently represent H, a $C_1$-$C_{10}$ linear or branched alkyl group, a $C_3$-$C_{10}$ cycloalkyl group, or together form with the carbon atom to which they are attached a $C_3$-$C_{10}$ cycloalkyl group;
X represents an halogen or a group of the following formula:

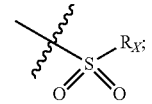

(X$_1$)

$R_X$ represents a $C_1$-$C_{10}$ linear or branched alkyl group, a $C_3$-$C_{10}$ cycloalkyl group, an aryl group, in particular a phenyl or naphtyl group, a $C_5$-$C_{10}$-membered heteroaryl; said $C_1$-$C_{10}$ linear or branched alkyl group, and $C_3$-$C_{10}$ cycloalkyl group being optionally substituted by at least one group selected from:
 a $C_3$-$C_{10}$ cycloalkyl group;
 a phenyl optionally substituted by at least one group selected from a $C_1$-$C_{10}$ linear or branched alkyl group, a $C_3$-$C_{10}$ cycloalkyl group, an halogen, a —OR$_{ii}$ group, an amine of formula —NR$_{ii}$'R$_{ii}$", a nitrile or a nitro group;
 a —OR$_i$ group;
 an amine of formula —NR$_i$'R$_i$";
said aryl and $C_5$-$C_{10}$-membered heteroaryl being optionally substituted by at least one group selected from:

a $C_1$-$C_{10}$ linear or branched alkyl group;
a $C_3$-$C_{10}$ cycloalkyl group;
a phenyl optionally substituted by at least one group selected from a $C_1$-$C_{10}$ linear or branched alkyl group, a $C_3$-$C_{10}$ cycloalkyl group, an halogen, a —$OR_{ii}$ group, an amine of formula —$NR_{ii}'R_{ii}''$, a nitrile or a nitro group;
an halogen;
a —$OR_i$ group; two adjacent —$OR_i$ groups forming possibly with the two C atoms bearing said —$OR_i$ groups a 1,4-dioxane ring;
an amine of formula —$NR_i'R_i''$;
a nitrile;
a nitro group;
a $CF_3$ group;
$R_i$ and $R_{ii}$ each independently represent H, a $C_1$-$C_{10}$ linear or branched alkyl group, a $C_3$-$C_{10}$ cycloalkyl group;
$R_i'$ and $R_i''$ each independently represent H, a $C_1$-$C_{10}$ linear or branched alkyl group, a $C_3$-$C_{10}$ cycloalkyl group, or together form with the nitrogen atom to which they are attached a $C_4$-$C_7$ heterocycloalkyl group;
$R_{ii}'$ and $R_{ii}''$ each independently represent H, a $C_1$-$C_{10}$ linear or branched alkyl group, a $C_3$-$C_{10}$ cycloalkyl group, or together form with the nitrogen atom to which they are attached a $C_4$-$C_7$ heterocycloalkyl group;
and the stereoisomeric forms, mixtures of stereoisomeric forms or pharmaceutically acceptable salts forms thereof;
provided that said compound is not of one of the following formulae:

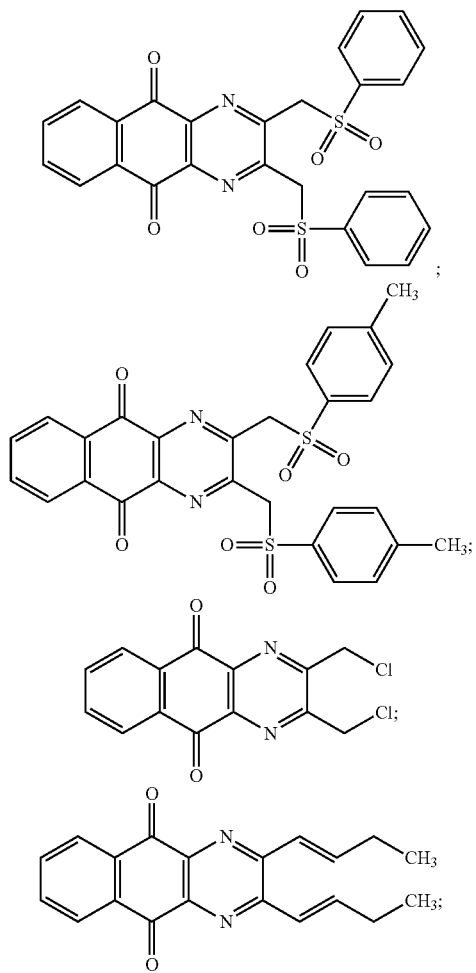

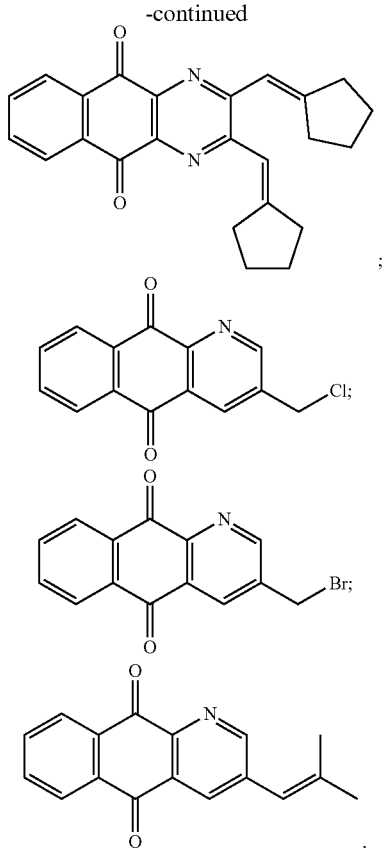

In particular, the present invention relates to a compound of following formula (II), and the stereoisomeric forms, mixtures of stereoisomeric forms or pharmaceutically acceptable salts forms thereof:

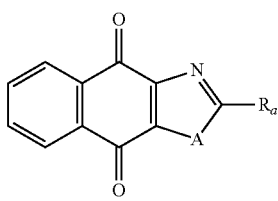

(II)

wherein:
A is selected from the group comprising:

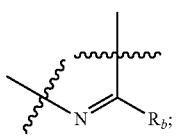

($A_1$)

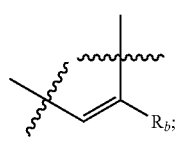

($A_2$)

-continued

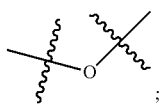
(A₃)

$R_a$ and $R_b$ each independently represent:
when A is $A_1$ or $A_3$, a group of one of the following formulae:

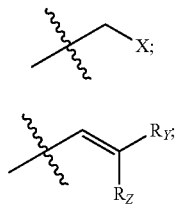
($R_{ab1}$), ($R_{ab2}$)

when A is $A_2$, H or a group of one of the following formulae:

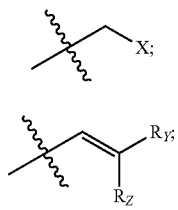
($R_{ab1}$), ($R_{ab2}$)

provided that at least one of $R_a$ and $R_b$, is not H;
$R_Y$ and $R_Z$ each independently represent H, a $C_1$-$C_{10}$ linear or branched alkyl group, a $C_3$-$C_{10}$ cycloalkyl group, or together form with the carbon atom to which they are attached a $C_3$-$C_{10}$ cycloalkyl group;
X represents an halogen or a group of the following formula:

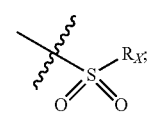
($X_1$)

$R_X$ represents a $C_1$-$C_{10}$ linear or branched alkyl group, a $C_3$-$C_{10}$ cycloalkyl group, a phenyl, a $C_5$-$C_{10}$-membered heteroaryl;
said $C_1$-$C_{10}$ linear or branched alkyl group, and $C_3$-$C_{10}$ cycloalkyl group being optionally substituted by at least one group selected from:
   a $C_3$-$C_{10}$ cycloalkyl group;
   a phenyl optionally substituted by at least one group selected from a $C_1$-$C_{10}$ linear or branched alkyl group, a $C_3$-$C_{10}$ cycloalkyl group, an halogen, a —$OR_{ii}$ group, an amine of formula —$NR_{ii}'R_{ii}''$, a nitrile or a nitro group;
   a —$OR_i$ group;
   an amine of formula —$NR_i'R_i''$;
said phenyl and $C_5$-$C_{10}$-membered heteroaryl being optionally substituted by at least one group selected from:

a $C_1$-$C_{10}$ linear or branched alkyl group;
a $C_3$-$C_{10}$ cycloalkyl group;
a phenyl optionally substituted by at least one group selected from a $C_1$-$C_{10}$ linear or branched alkyl group, a $C_3$-$C_{10}$ cycloalkyl group, an halogen, a —$OR_{ii}$ group, an amine of formula —$NR_{ii}'R_{ii}''$, a nitrile or a nitro group;
an halogen;
a —$OR_i$ group;
an amine of formula —$NR_i'R_i''$;
a nitrile;
a nitro group;
$R_i$ and $R_{ii}$ each independently represent H, a $C_1$-$C_{10}$ linear or branched alkyl group, a $C_3$-$C_{10}$ cycloalkyl group;
$R_i'$ and $R_i''$ each independently represent H, a $C_1$-$C_{10}$ linear or branched alkyl group, a $C_3$-$C_{10}$ cycloalkyl group, or together form with the nitrogen atom to which they are attached a $C_4$-$C_7$ heterocycloalkyl group;
$R_i'$ and $R_{ii}''$ each independently represent H, a $C_1$-$C_{10}$ linear or branched alkyl group, a $C_3$-$C_{10}$ cycloalkyl group, or together form with the nitrogen atom to which they are attached a $C_4$-$C_7$ heterocycloalkyl group;
and the stereoisomeric forms, mixtures of stereoisomeric forms or pharmaceutically acceptable salts forms thereof;
provided that said compound is not of one of the following formulae:

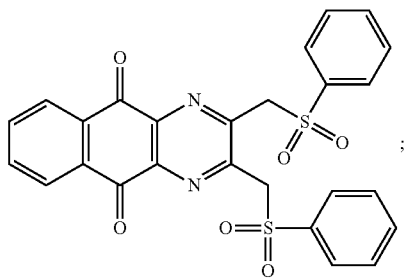

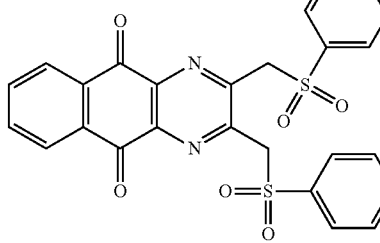

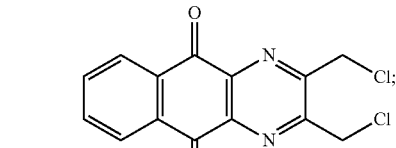

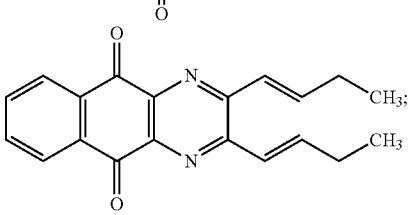

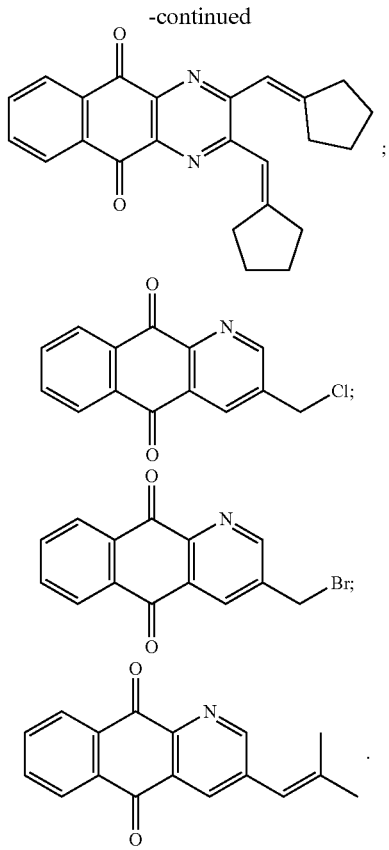

It is to be noted that the present invention includes the combination of all the embodiments listed here above for formula (I), (I$_A$), (I$_B$) or (I$_C$).

In particular embodiment, there are included compounds of formula (II) for use as defined above, wherein R$_a$ and R$_b$ each independently represent a group of the following formula:

(R$_{ab1}$)

X represents a group of the following formula:

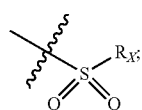

(X$_1$)

R$_X$ represents a C$_1$-C$_{10}$ linear or branched alkyl group, a C$_3$-C$_{10}$ cycloalkyl group, an aryl group, in particular a phenyl or naphtyl group, a C$_5$-C$_{10}$-membered heteroaryl; said C$_1$-C$_{10}$ linear or branched alkyl group, and C$_3$-C$_{10}$ cycloalkyl group being optionally substituted by at least one group selected from:

- a C$_3$-C$_{10}$ cycloalkyl group;
- a phenyl optionally substituted by at least one group selected from a C$_1$-C$_{10}$ linear or branched alkyl group, a C$_3$-C$_{10}$ cycloalkyl group, an halogen, a —OR$_{ii}$ group, an amine of formula —NR$_{ii}$'R$_{ii}$", a nitrile or a nitro group;
- a —OR$_i$ group;
- an amine of formula —NR$_i$'R$_i$";

said C$_5$-C$_{10}$-membered heteroaryl being optionally substituted by at least one group selected from:
- a C$_1$-C$_{10}$ linear or branched alkyl group;
- a C$_3$-C$_{10}$ cycloalkyl group;
- a phenyl optionally substituted by at least one group selected from a C$_1$-C$_{10}$ linear or branched alkyl group, a C$_3$-C$_{10}$ cycloalkyl group, an halogen, a —OR$_{ii}$ group, an amine of formula —NR$_{ii}$'R$_{ii}$", a nitrile or a nitro group;
- an halogen;
- a —OR$_i$ group; two adjacent —OR$_i$ groups forming possibly with the two C atoms bearing said —OR$_i$ groups a 1,4-dioxane ring;
- an amine of formula —NR$_i$'R$_i$";
- a nitrile;
- a nitro group;
- a CF$_3$ group;

said aryl being substituted by at least one group selected from:
- a C$_1$-C$_{10}$ linear or branched alkyl group;
- a C$_3$-C$_{10}$ cycloalkyl group;
- a phenyl optionally substituted by at least one group selected from a C$_1$-C$_{10}$ linear or branched alkyl group, a C$_3$-C$_{10}$ cycloalkyl group, an halogen, a —OR$_{ii}$ group, an amine of formula —NR$_{ii}$'R$_{ii}$", a nitrile or a nitro group;
- an halogen;
- a —OR$_i$ group; two adjacent —OR$_i$ groups forming possibly with the two C atoms bearing said —OR$_i$ groups a 1,4-dioxane ring;
- an amine of formula —NR$_i$'R$_i$";
- a nitrile;
- a nitro group;
- a CF$_3$ group;

provided that, when the R$_X$ group=phenyl is substituted by a C$_1$-C$_{10}$ linear or branched alkyl group, said phenyl is substituted by a further group as defined above.

In particular embodiment, there are included compounds of formula (II) for use as defined above, wherein R$_a$ and R$_b$ each independently represent a group of the following formula:

(R$_{ab1}$)

X represents a group of the following formula:

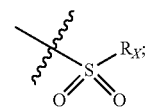

(X$_1$)

R$_X$ represents a C$_1$-C$_{10}$ linear or branched alkyl group, a C$_3$-C$_{10}$ cycloalkyl group, a phenyl, a C$_5$-C$_{10}$-membered heteroaryl;

said $C_1$-$C_{10}$ linear or branched alkyl group, and $C_3$-$C_{10}$ cycloalkyl group being optionally substituted by at least one group selected from:
- a $C_3$-$C_{10}$ cycloalkyl group;
- a phenyl optionally substituted by at least one group selected from a $C_1$-$C_{10}$ linear or branched alkyl group, a $C_3$-$C_{10}$ cycloalkyl group, an halogen, a —$OR_{ii}$ group, an amine of formula —$NR_{ii}'R_{ii}''$, a nitrile or a nitro group;
- a —$OR_i$ group;
- an amine of formula —$NR_i'R_i''$;

said $C_5$-$C_{10}$-membered heteroaryl being optionally substituted by at least one group selected from:
- a $C_1$-$C_{10}$ linear or branched alkyl group;
- a $C_3$-$C_{10}$ cycloalkyl group;
- a phenyl optionally substituted by at least one group selected from a $C_1$-$C_{10}$ linear or branched alkyl group, a $C_3$-$C_{10}$ cycloalkyl group, an halogen, a —$OR_{ii}$ group, an amine of formula —$NR_{ii}'R_{ii}''$, a nitrile or a nitro group;
- an halogen;
- a —$OR_i$ group;
- an amine of formula —$NR_i'R_i''$;
- a nitrile;
- a nitro group;

said phenyl being substituted by at least one group selected from:
- a $C_1$-$C_{10}$ linear or branched alkyl group;
- a $C_3$-$C_{10}$ cycloalkyl group;
- a phenyl optionally substituted by at least one group selected from a $C_1$-$C_{10}$ linear or branched alkyl group, a $C_3$-$C_{10}$ cycloalkyl group, an halogen, a —$OR_{ii}$ group, an amine of formula —$NR_{ii}'R_{ii}''$, a nitrile or a nitro group;
- an halogen;
- a —$OR_i$ group;
- an amine of formula —$NR_i'R_i''$;
- a nitrile;
- a nitro group;
- provided that, when the $R_X$ group=phenyl is substituted by a $C_1$-$C_{10}$ linear or branched alkyl group, said phenyl is substituted by a further group as defined above.

Definitions

The following terms and expressions contained herein are defined as follows:

As used herein, a range of values in the form "x-y" or "x to y", or "x through y", include integers x, y, and the integers therebetween. For example, the phrases "1-6", or "1 to 6" or "1 through 6" are intended to include the integers 1, 2, 3, 4, 5, and 6. Preferred embodiments include each individual integer in the range, as well as any subcombination of integers. For example, preferred integers for "1-6" can include 1, 2, 3, 4, 5, 6, 1-2, 1-3, 1-4, 1-5, 2-3, 2-4, 2-5, 2-6, etc.

As used herein, the term "alkyl" refers to a straight-chain, or branched alkyl group having 1 to 10 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. A designation such as "$C_1$-$C_4$ alkyl" refers to an alkyl radical containing from 1 to 4 carbon atoms.

As used herein, the term "cycloalkyl" refers to a saturated or partially saturated mono- or bicyclic alkyl ring system containing 3 to 10 carbon atoms. A designation such as "$C_4$-$C_7$ cycloalkyl" refers to a cycloalkyl radical containing from 4 to 7 ring carbon atoms. Preferred cycloalkyl groups include those containing 5 or 6 ring carbon atoms. Examples of cycloalkyl groups include such groups as cyclopropyl, cyclobutyl, cyclopentyl, cyclohexyl, cycloheptyl, cyclooctyl, pinenyl, and adamantanyl.

As used herein, the term "aryl" refers to a substituted or unsubstituted, mono- or bicyclic hydrocarbon aromatic ring system having 6 to 10 ring carbon atoms. Examples include phenyl and naphthyl. Preferred aryl groups include unsubstituted or substituted phenyl and naphthyl groups. As used herein, the term "heteroaryl" refers to an aromatic group containing 5 to 10 ring carbon atoms in which one or more ring carbon atoms are replaced by at least one hetero atom such as —O—, —N—, or —S—. Examples of heteroaryl groups include thiophenyl, pyrrolyl, furanyl, thienyl, pirazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl.

As used herein, the term "subject" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention effective to prevent or treat the symptoms of particular disorder.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

All other terms used in the description of the present invention have their meanings as is well known in the art.

In another aspect, the present invention is directed to pharmaceutically acceptable salts of the compounds described above. As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically-acceptable salts, other salts are included in the invention. They may serve as intermediates in the purification of the compounds, in the preparation of other salts, or in the identification and characterization of the compounds or intermediates.

It is recognized that compounds of the present invention may exist in various stereoisomeric forms. As such, the compounds of the present invention include both diastereomers and enantiomers. The compounds are normally prepared as racemates and can conveniently be used as such, but individual enantiomers can be isolated or synthesized by conventional techniques if so desired. Such racemates and individual enantiomers and mixtures thereof form part of the present invention.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J, et al. *Enantiomers, Racemates, and Resolutions*; Wiley: New York, 1981, each incorporated by reference herein in their entireties.

Synthesis

The compounds of the present invention may be prepared in a number of methods well known to those skilled in the art, including, but not limited to those described below, or through modifications of these methods by applying standard techniques known to those skilled in the art of organic synthesis. The appropriate modifications and substitutions will be readily apparent and well known or readily obtainable from the scientific literature to those skilled in the art. In particular, such methods can be found in R. C. Larock, *Comprehensive Organic Transformations*, Wiley-VCH Publishers, 1999.

All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms, isomeric forms of a structure are intended, unless the specific stereochemistry or isomeric form is specifically indicated. It is well-known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, 3$^{rd}$ ed., John Wiley and Sons, 1999; J. F. W. McOmie in *Protective Groups in Organic Chemistry*, Plenum Press, 1973.

The reagents and starting materials are commercially available, or readily synthesized by well-known techniques by one of ordinary skill in the arts. All substituents in the synthetic Schemes, unless otherwise indicated, are as previously defined.

Compounds of formula ($I_A$), wherein $R_a$ and $R_b$ represent

(R$_{ab1}$)

X being

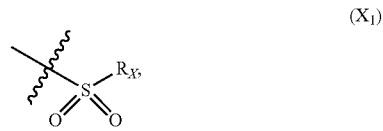

(X$_1$)

may be obtained by contacting PCR8146 (which is for instance obtained according to the procedure described in Remusat et al., *J. Heterocycl. Chem.* 2004, 41, 221-225) with a sulfonyl chloride of following formula:

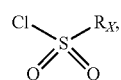

in particular in presence of sodium sulfite and sodium hydrogenocarbonate according to the procedure described in Liu, L. K. et al. *J. Org. Chem.* 1980, 45, 406-410.

Compounds of formula ($I_B$), wherein $R_a$ represent H and $R_b$ represent

(R$_{ab1}$)

X being

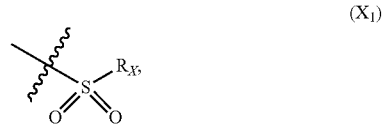

(X$_1$)

may be obtained by contacting the 3-(chloromethyl)benzo[g]quinoline-5,10-dione (which is for instance obtained according to the procedure described in Rathelot et al., *Molecules* 2002, 7, 917-921) with a sulfonyl chloride of following formula:

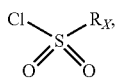

in particular in presence of sodium sulfite and sodium hydrogenocarbonate according to the procedure described in Liu, L. K. et al. *J. Org. Chem.* 1980, 45, 406-410.

Compounds of formula ($I_C$), wherein $R_a$ represents

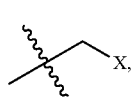 ($R_{ab1}$)

X being

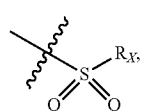 ($X_1$)

may be obtained by contacting 2-(bromomethyl)naphtho[2,3-d]oxazole-4,9-dione (which is for instance obtained according to the procedure described by Rathelot et al., *Heterocycles* 2000, 53, 1075-1084) with a sulfonyl chloride of following formula:

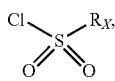

in particular in presence of sodium sulfite and sodium hydrogenocarbonate according to the procedure described in Liu, L. K. et al. *J. Org. Chem.* 1980, 45, 406-410.

DESCRIPTION OF THE DRAWINGS

FIG. 1 illustrates the differential inhibition of $USP2^{CD}$ and $USP8^{CD}$ by PCR6236 or PCR9301. IC50 were monitored on Ub-Rho substrate (0.1 µM).

PCR6236 and PCR9301 inhibit $USP2^{CD}$ activity in the micromolar range and $USP8^{CD}$ catalytic activity in the nanomolar range.

FIGS. 1A,A' and 1B,B': determination of $IC_{50}$ values. Purified $USP2^{CD}$ (FIG. 1A,A') or $USP8^D$ (FIG. 1B,B') was incubated in the presence of Ub-Rho and increasing doses of PCR6236 or PCR9301 as indicated in µM (FIG. 1A) or nM (FIG. 1A',B,B'). The curves correspond to the medium value of technical triplicates.

FIGS. 1C and 1D: visualization of tri-$Ub^{K63}$ chains hydrolysis by $USP2^{CD}$ (FIG. 1C) or $USP8^{CD}$ (FIG. 1D) in the presence of DMSO and its full inhibition in the presence of PCR6236 or PCR9301 (as indicated) at the indicated concentrations.

Figure 2:
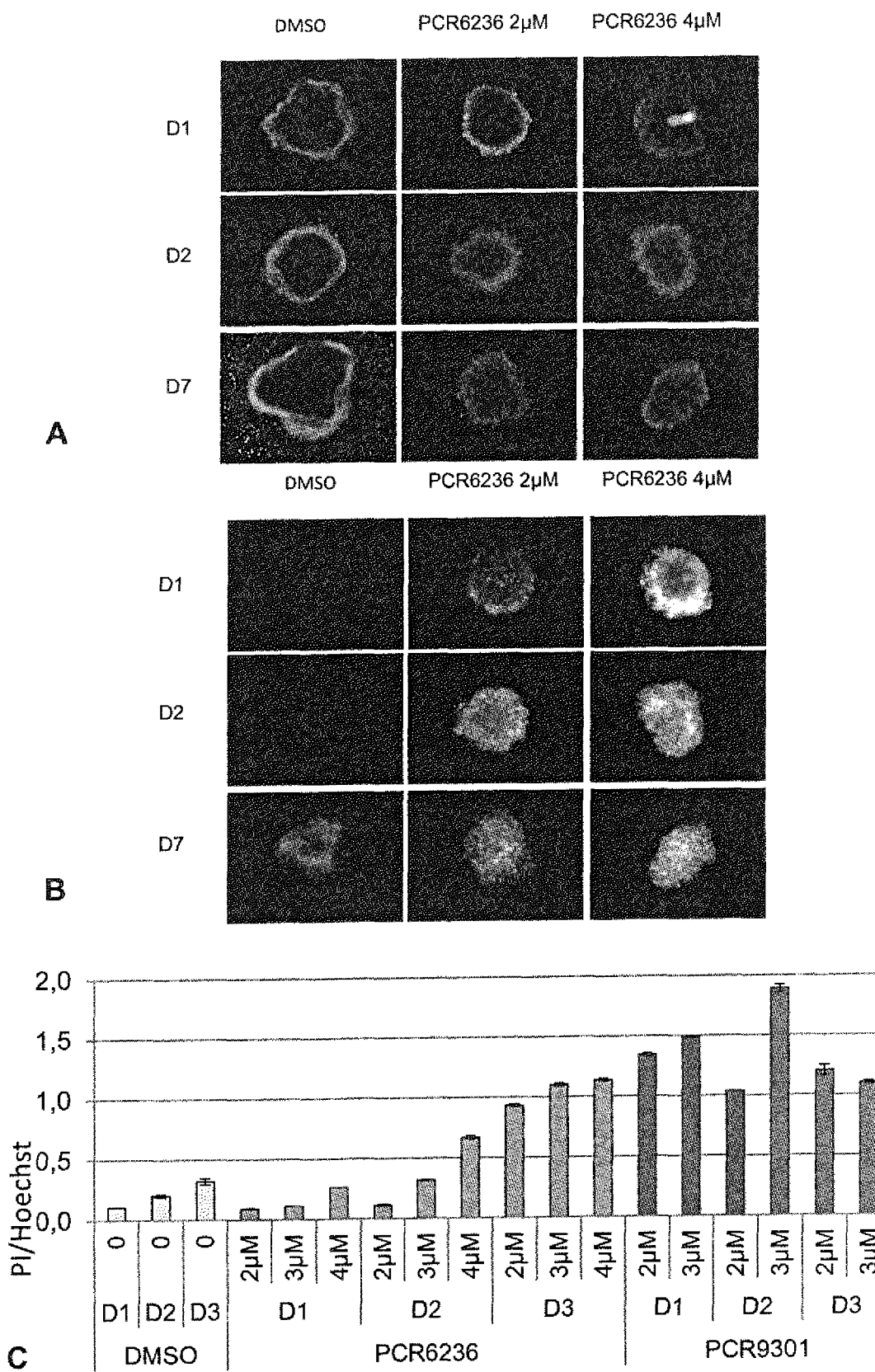

FIG. 2 shows the monitoring of cell death induced in 3D spheroids LNCaP cells.

FIGS. 2A and 2B: one Day (D1), two days (D2) and seven days (D7) old LNCaP cells spheroids were stained with Hoechst (FIG. 2A) and Propidium Iodure (PI) (FIG. 2B) to visualize living and dead cells, respectively in the presence of either DMSO, or PCR6236 at 2 µM or 4 µM final concentration.

FIG. 2C: three days old LNCaP cells spheroids were treated with DMSO or PCR6236 or PCR9301 at the indicated concentrations for one to three days (D1, D2 and D3). Spheroids were then stained with Hoechst and Propidium Iodure (PI). The area of each staining was calculated via automated imaging. Histograms represent the medium value of the PI/Hoechst areas ratio calculated on 3 to 6 independent spheroids. Error bars indicate the standard deviation between technical replicates. One out of three experiments is presented.

Figure 3:
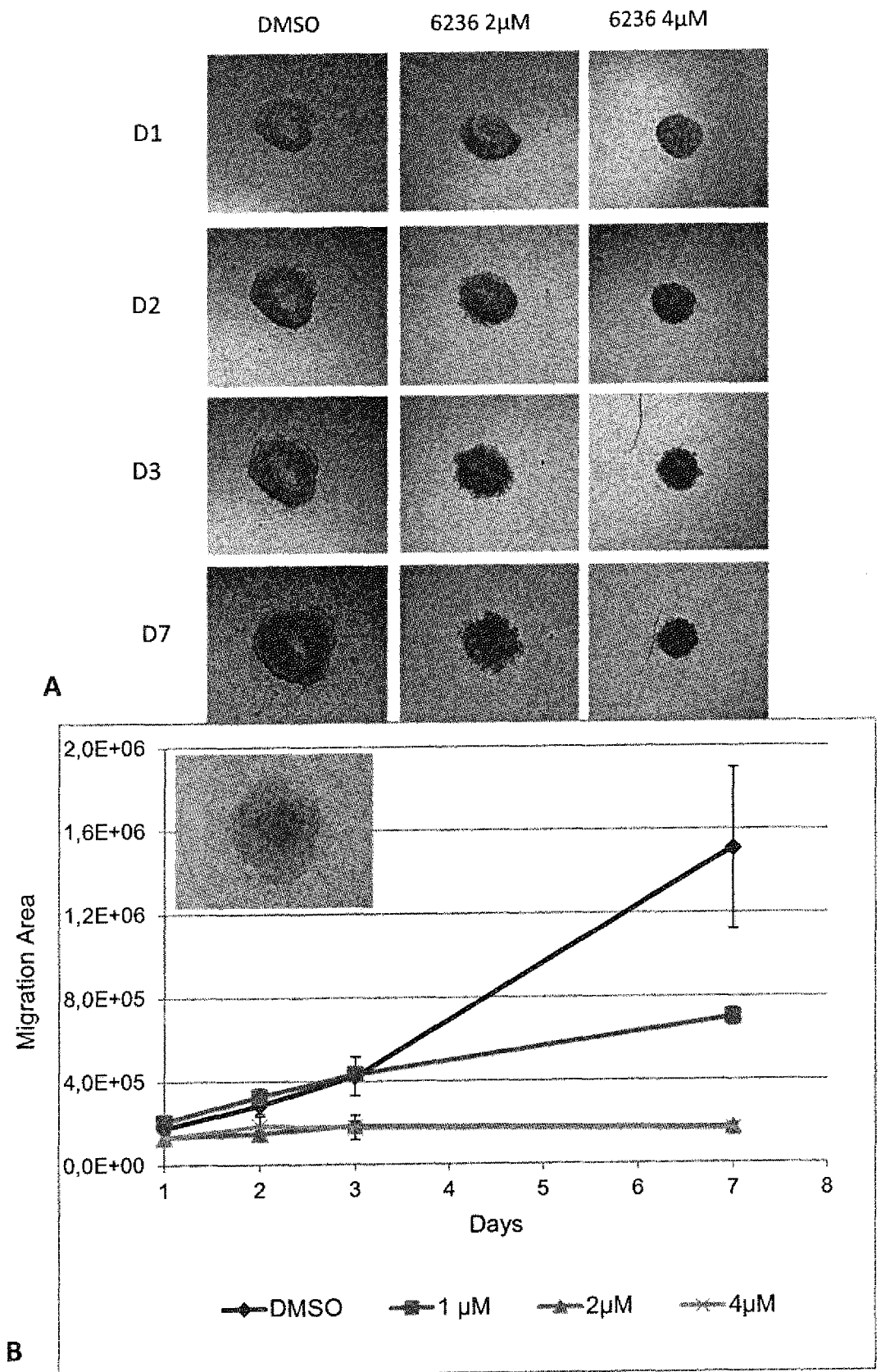

FIG. 3 shows the prevention of cell migration out of LNCaP cells 3D spheroids thanks to PCR6236. Three days old LNCaP cells spheroids were treated with DMSO or PCR6236 at the indicated concentrations for one to seven days.

FIG. 3A: pictures of spheroids observed by phase contrast at D1, D2, D3 and D7.

FIG. 3B: mean of the migration area out of the spheroids over time for 3 to 6 spheroids. Error bars indicate standard deviation between technical replicates.

Figure 4:
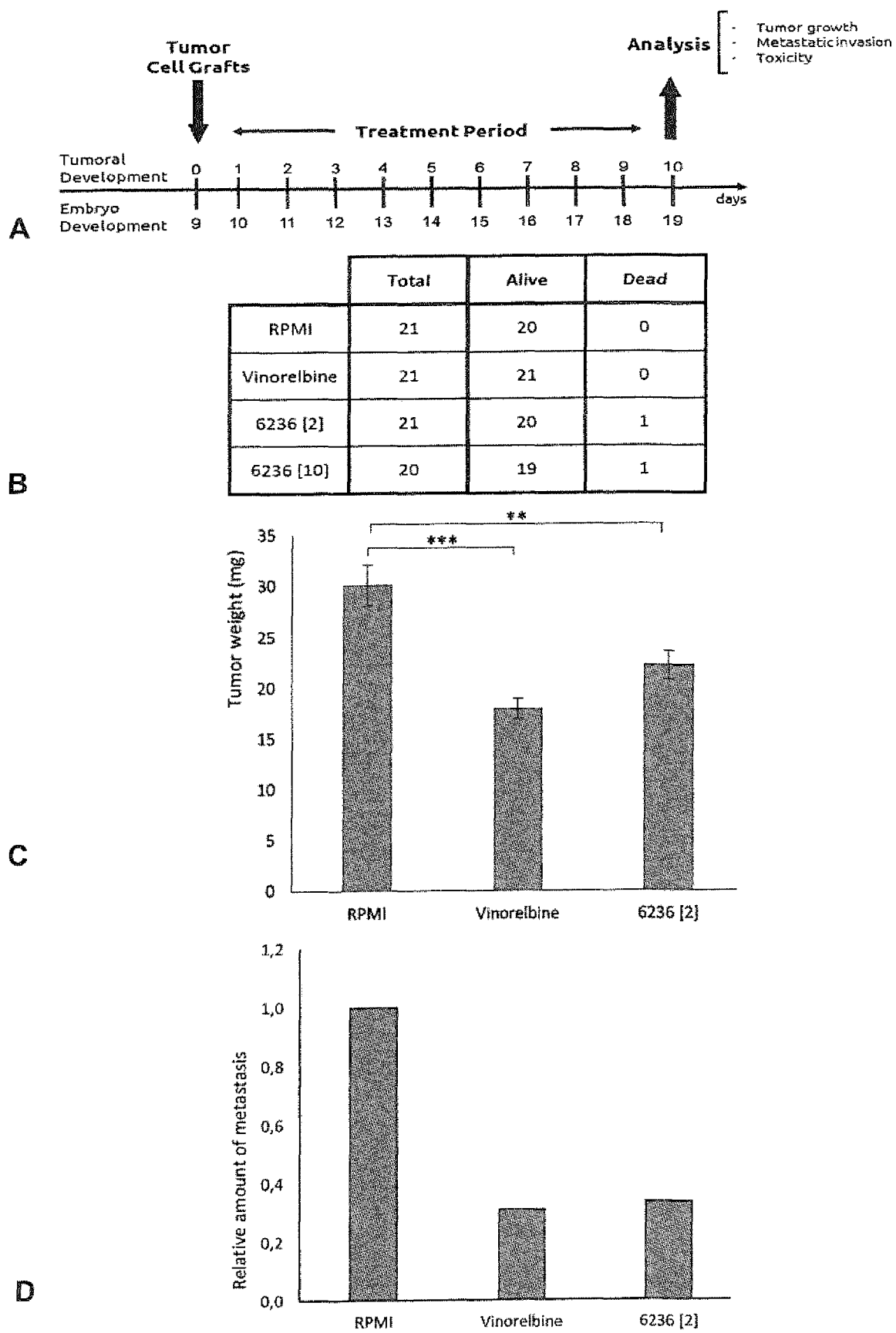

FIG. 4 illustrates the tumor growth and metastasis reduction in chicken embryos induced xenograft tumors of PC-3 cells, using PCR6236.

FIG. 4A: scheme of the experimental protocol.

FIG. 4B: number of surviving embryos used in the study.

FIG. 4C: mean values of tumor weight (error bars indicate SEM).

FIG. 4D: relative amount of metastasis in lower CAM.

B-D. RPMI: untreated embryos, Vinorelbine: reference compound used at 1 µM, 6236[2]: PCR6236 at 2 µM, 6236[10]: PCR6236 at 10 µM.

Figure 5:
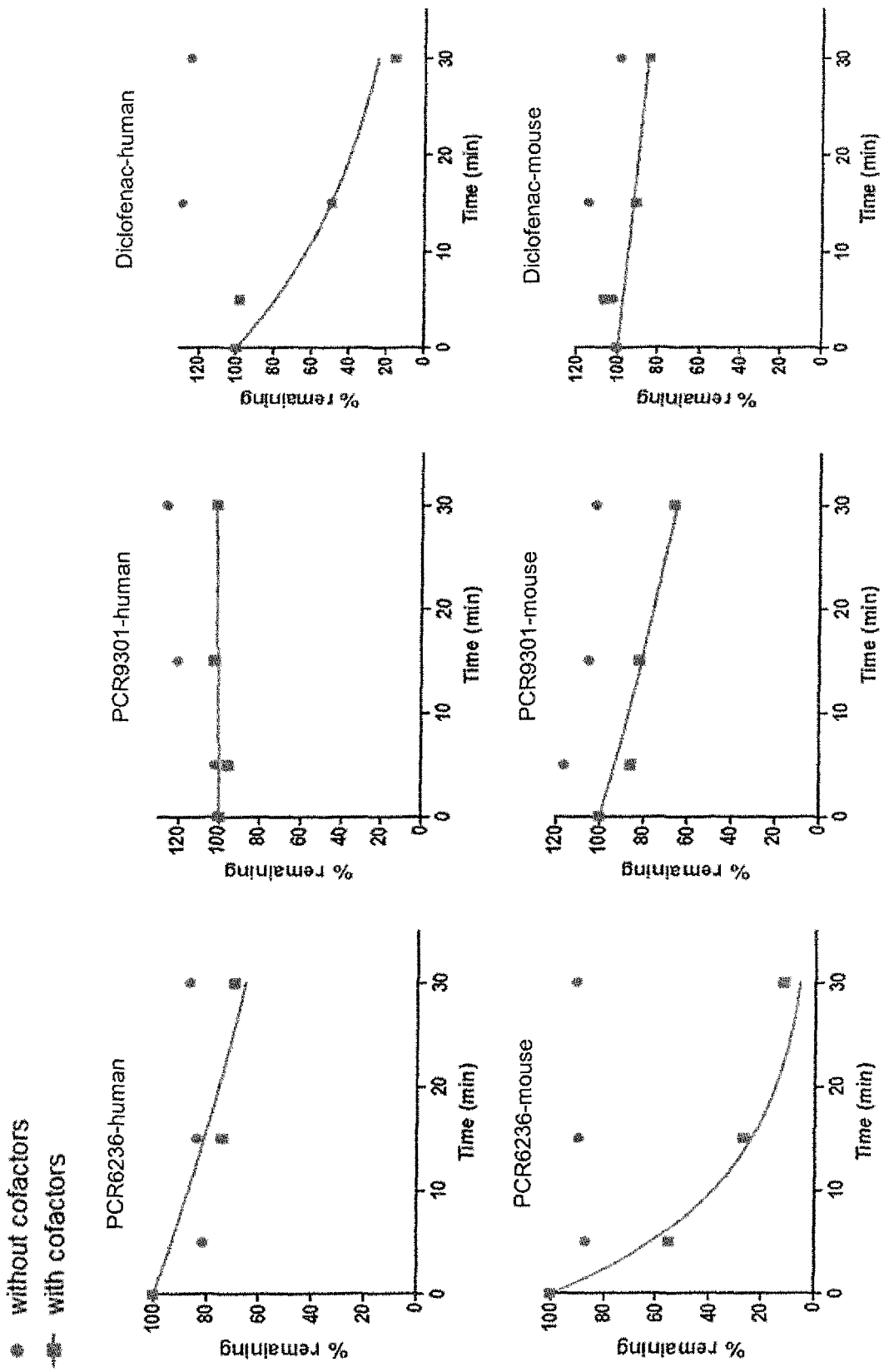

FIG. 5 shows the metabolic stability (phase I) of PCR6236 and PCR9301 on human and mouse liver microsomes. The metabolic stability of PCR6236 and PCR9301 was monitored on suspended human or mouse liver cells at a concentration of 0.5 µM for 0 min, 5 min, 15 min and 30 min incubation times. Each compound was incubated either with cofactors (n=2) or without cofactors (n=1). Positive controls were: Diclofenac, Midazolam and Amitriptyline.

Figure 6:
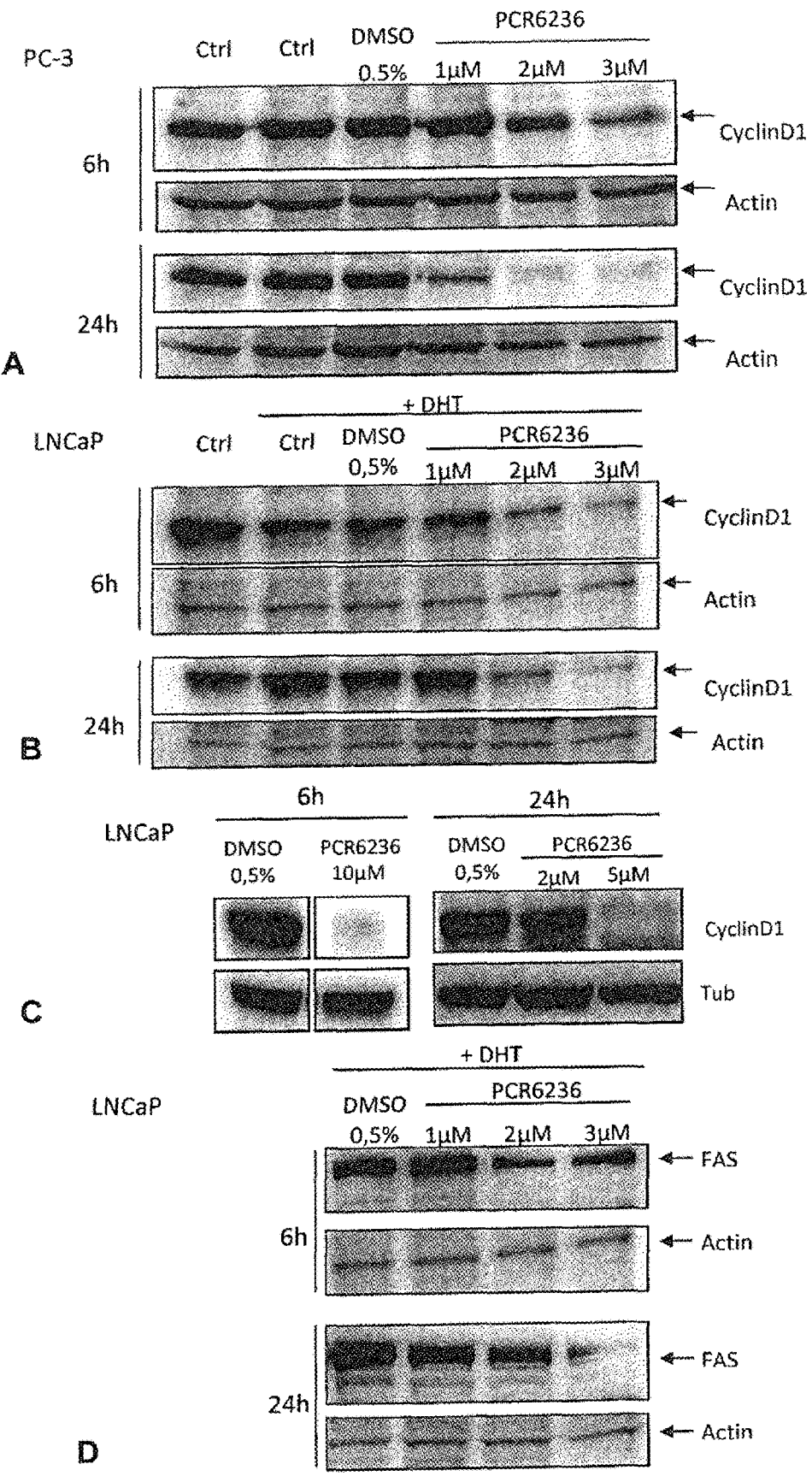

FIG. 6 shows the destabilization of CyclinD1 and FAS in prostatic cancer cells by PCR6236. Protein expression was checked by immunoblots of PC-3 (FIG. 6A) or LNCaP (FIG. 6B-D) lysates from cells treated or not with increasing concentrations of PCR6236 for 6 h or 24 hours as indicated. In FIG. 6B and FIG. 6D, LNCaP cells were treated with dihydrotestosterone (DHT) to induce hormonal dependent FAS expression. Actin or Tubulin (Tub) serve as loading controls. One representative experiment out of three is presented.

Figure 7:
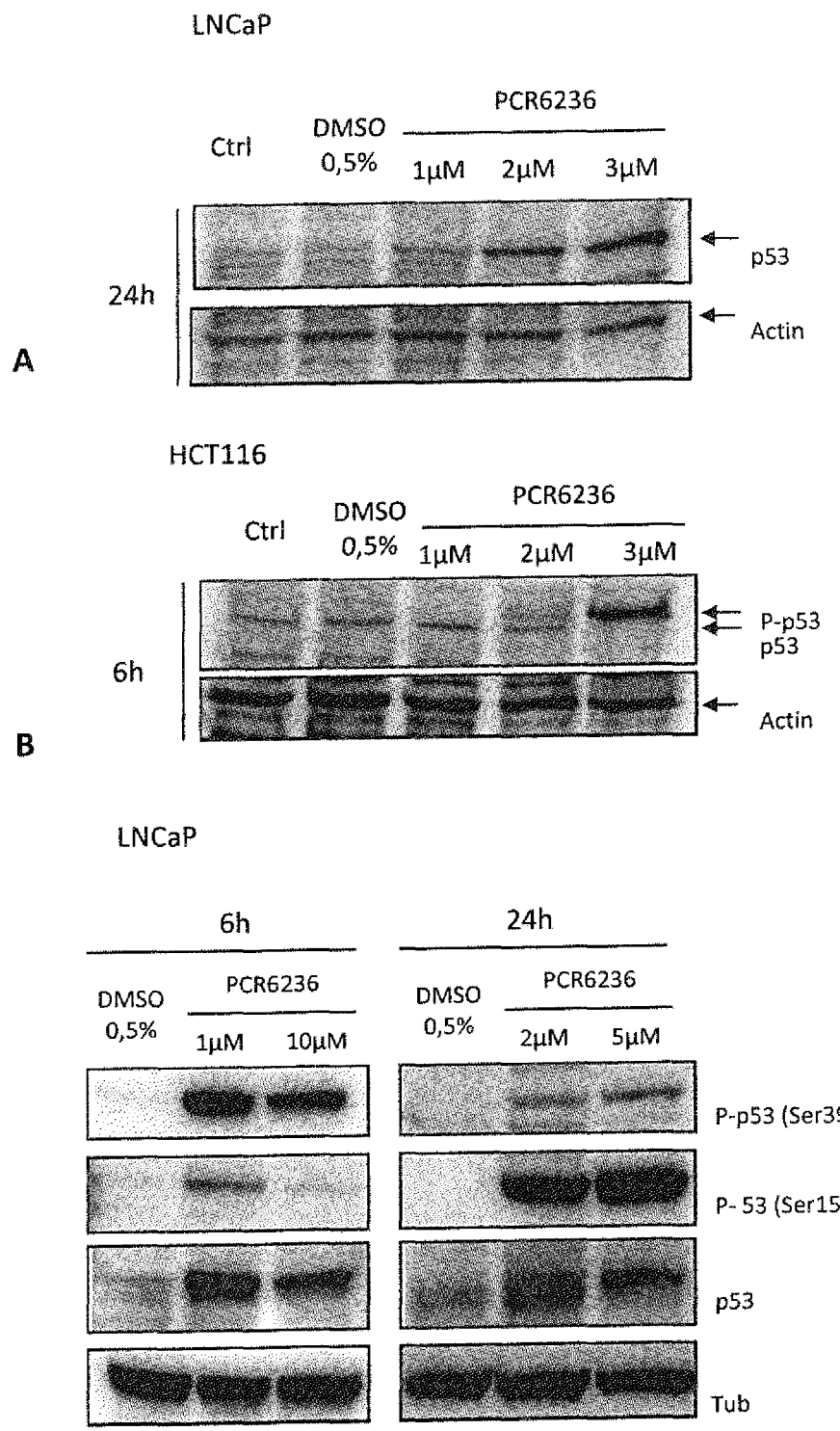

FIG. 7 illustrates the stabilization and activation of p53 in LNCaP and HCT116 cancerous cells by PCR6236. Protein expression was checked by immunoblots of LNCaP (FIG. 7A,C) or HCT116 (FIG. 7B) lysates from cells treated or not with increasing concentrations of PCR6236 for 6 h or 24 hours as indicated. Actin or Tubulin (Tub) serve as loading controls. One representative experiment out of three is presented.

Figure 8:
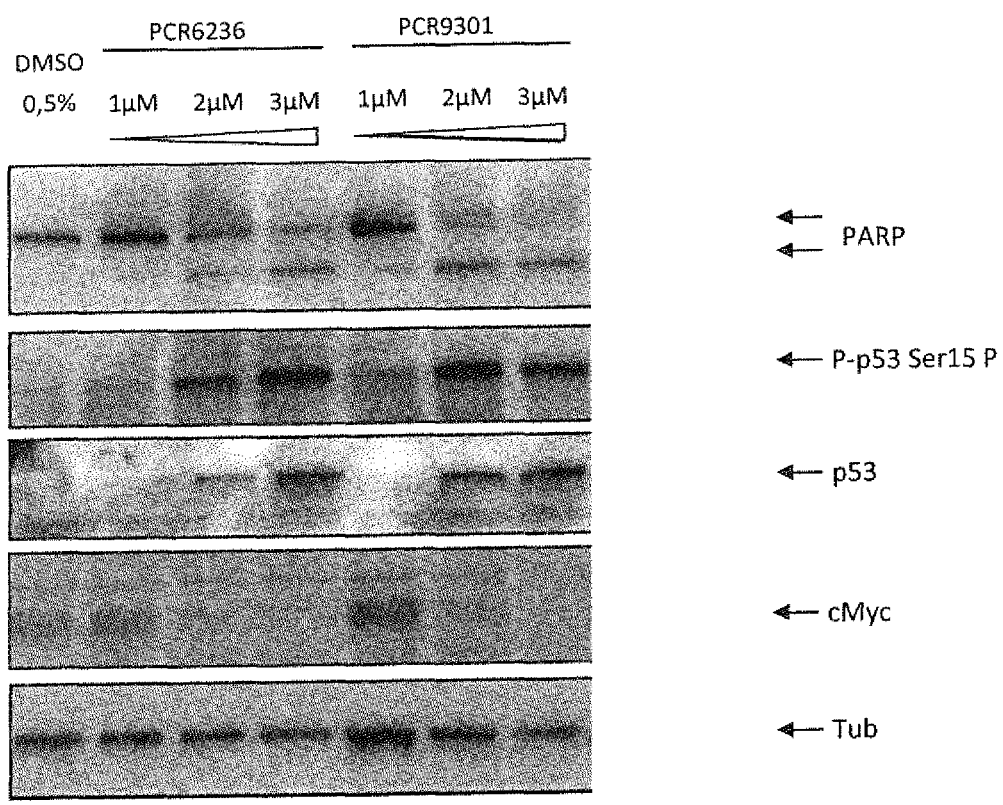

FIG. 8 shows the induction of PARP cleavage, p53 accumulation and phosphorylation and cMyc degradation in LNCaP cells by PCR6236 and PCR9301. Protein expression was checked by immunoblots of LNCaP lysates from cells treated or not for 24 hours with increasing concentrations of PCR6236 or PCR9301 as indicated. Tubulin (Tub) serves as loading controls. One representative experiment out of three is presented.

FIG. 9 shows the visualization of the cell spreading during 24 hours following addition of each compound by video-microscopy (1 acquisition each 30 min).

Figure 9A:
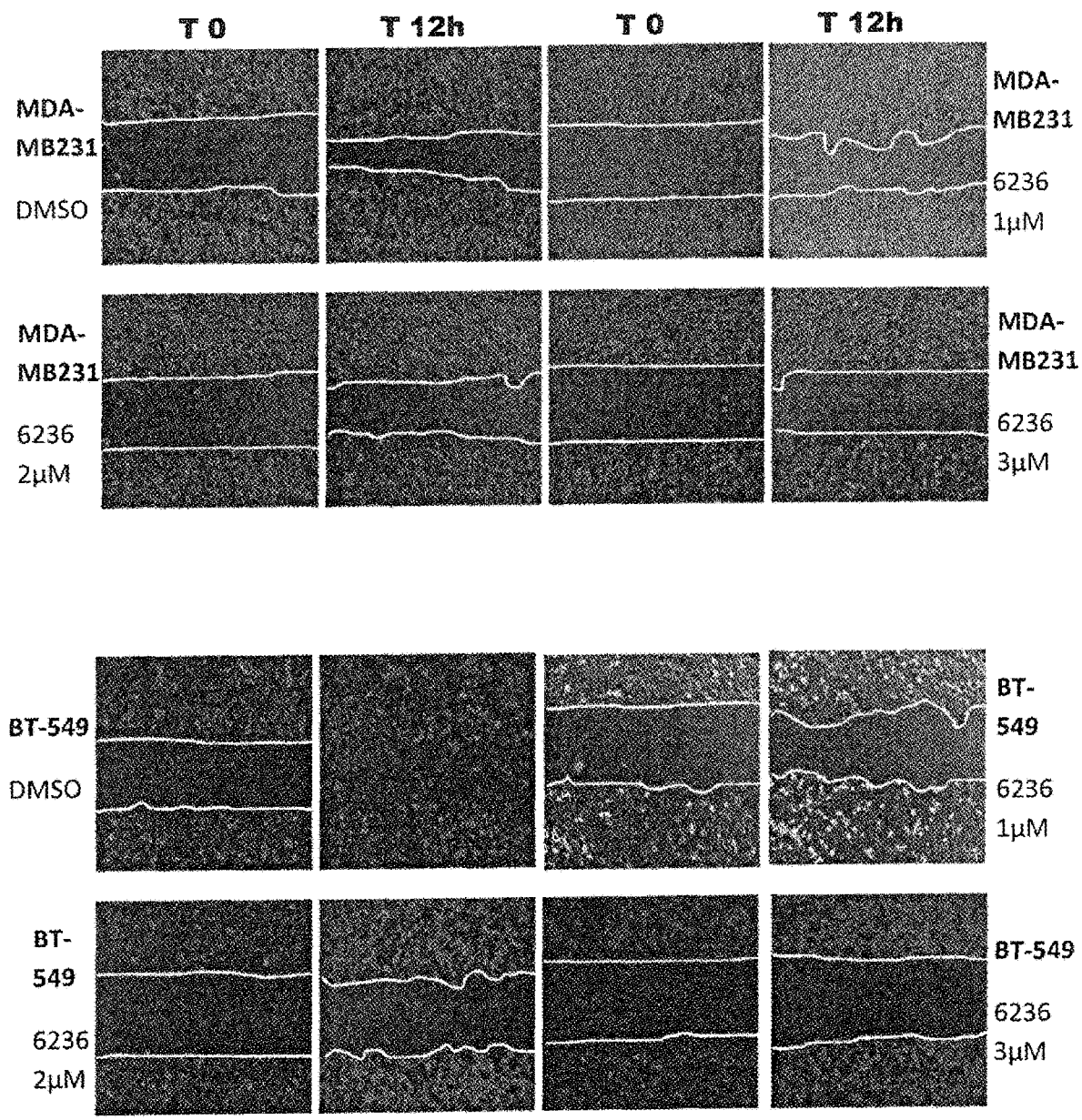

FIG. 9A: A representative picture out of 3 is presented at times 0 and 12 hours of drug treatment. The migratory front was delimited using the Image J software.

FIG. 9B: The empty surface (devoid of cells) was determined over time using Image J software.

Figure 10:
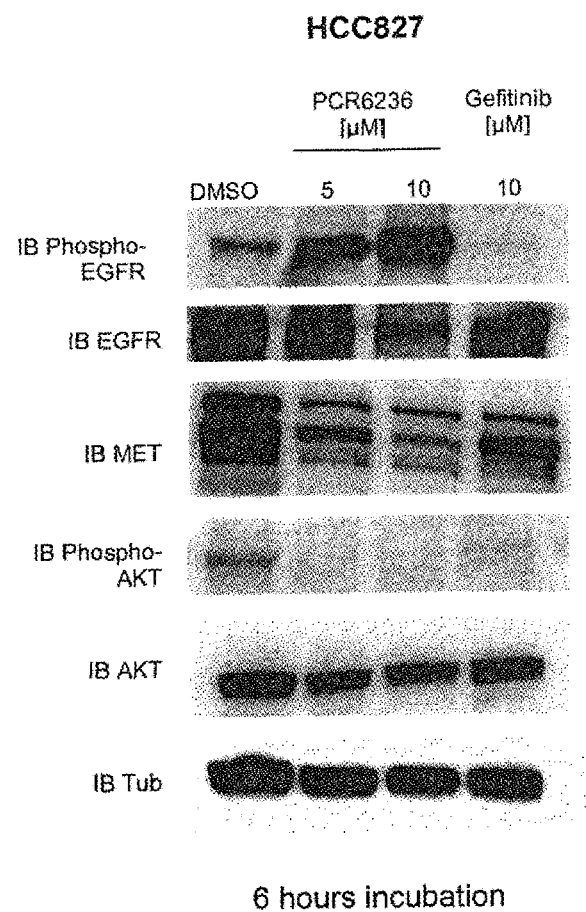

FIG. 10 illustrates the phosphorylation and degradation of EGFR, the degradation of Met, the absence of phosphorylation of AKT in HCC827 cells treated with PCR6236. Protein expression was checked by immunoblots of HCC827 cell lysates from cells treated or not with increasing concentrations of PCR6236 for 6 h. Tubulin (Tub) serve as loading controls. One representative experiment out of two is presented.

Figure 11:
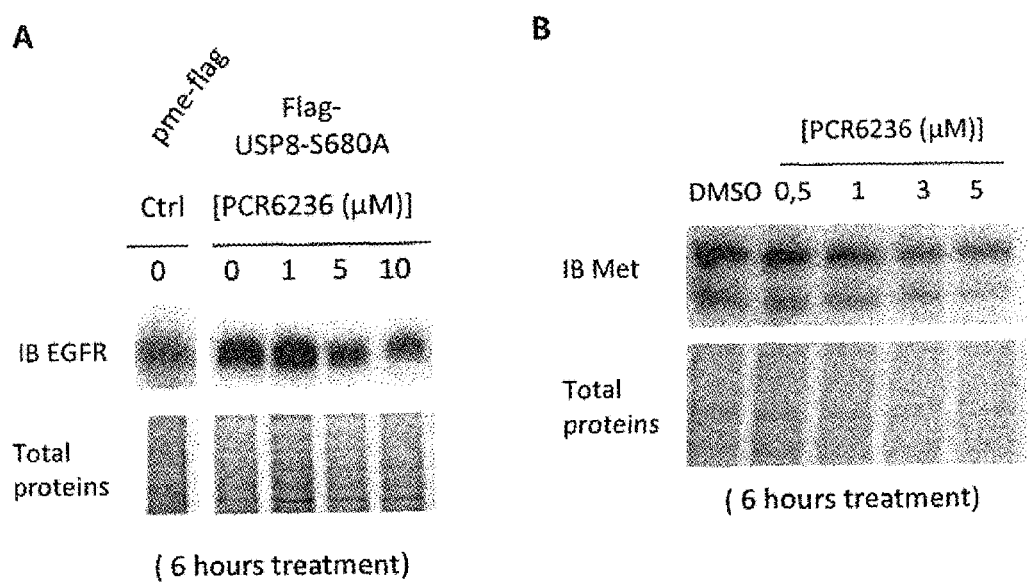

FIG. 11 illustrates the degradation of EGFR in HEK293T cells expressing the Flag-USP8-S680A construct and the degradation of Met in HEK293T by PCR6236. Protein expression was checked by immunoblots of HEK293T cell lysates from cells treated or not with increasing concentrations of PCR6236 for 6 h. Total proteins staining serves as loading controls. One representative experiment out of two is presented.

FIG. 12: The cell growth inhibition and cell death induction of non-small cell lung cancers (NSCLC), HCC827 cells and derivative Gefitinib-resistant clone H1975 (FIG. 12 A,B) and of PC-3 (FIG. 12 C,D) and LnCAP (FIG. 12 E,F) were monitored using Incucyte microscope. Histogram represent in A,C,E: the final cell area relative to the total well area in (%) and in B,D,F: the fluorescent area in µm2. Error bars indicate standard deviation between 6 technical replicates.

FIG. 13: Inhibition of Ub-Vs (ubiquitin-vinyl sulfone) binding to either USP2-CD or USP8-CD by PCR6236 as evidence that PCR6236 inhibits ubiquitin substrate binding to USP2 and USP8 both on purified proteins and on protein purified from HEK-293T cell lysates FIG. 13 A: The HA-tagged purified catalytic domain of USP2 (indicated USP2-CD) at 75 nM concentration was incubated for 20 minutes with HA-Ub-Vs at 2 µM concentration and/or with PCR6236 at indicated concentrations or DMSO at 0.5% as control. The mixture was then separated on SDS page and immunoblotted with anti-USP2 antibodies. The upper band corresponds to USP2-CD linked to HA-Ub-Vs while the lower band corresponds to unbound USP2-CD.

FIG. 13 B: The His-tagged purified catalytic domain of USP8 (indicated USP8-CD) at 3 µM concentration was incubated for 20 minutes with HA-Ub-Vs at 2 µM concentration and/or with PCR6236 at indicated concentrations or DMSO at 0.5% as control. The mixture was then separated on SDS page and immunoblotted with anti-His (to reveal USP8-CD) antibodies. The upper band corresponds to USP8-CD linked to HA-Ub-Vs while the lower ban corresponds to unbound USP8-CD.

FIG. 13 C: HA-USP2 constructs were transfected in HEK293T cells for 48 hours using standard protocols. After cell lysis, the whole cell lysate was incubated with HA-Ub-Vs at 0.75 µM during 12 hours. Then the mixture was separated on SDS-page gel and immunoblotted with anti USP2 antibodies. The upper band corresponds to USP2 linked to HA-Ub-Vs while the lower band corresponds to free USP2. Immunoblot with anti-tubulin (Tub) antibodies served as internal loading control.

FIG. 13 D: Flag-USP8 constructs were transfected in HEK293T cells for 48 hours using standard protocols. After cell lysis, the whole cell lysate was incubated with HA-Ub-Vs at 1.5 µM during 12 hours. Then the mixture was separated on SDS-page gel and immunoblotted with anti Flag antibodies (to reveal USP8). The upper band corresponds to USP8 linked to HA-Ub-Vs while the lower band corresponds to free USP8. Immunoblot with anti-tubuline antibodies served as internal loading control.

Increasing concentrations of PCR6236 prevents HA-Ub-VS binding to USP2CD.

Increasing concentrations of PCR6236 prevents HA-Ub-VS binding to USP8CD.

Increasing concentrations of PCR6236 decreased HA-Ub-VS binding to USP2 in the whole cell lysate.

Increasing concentrations of PCR6236 decreased HA-Ub-VS binding to USP8 in the whole cell lysate.

EXAMPLES

Example 1: Synthesis of the benzo[g]quinoxaline-5,10-diones Compounds

General Procedure

In a two-necked flask equipped with a drying tube, a solution of 4.5 mmol (9 eq.) of the corresponding sulfonyl chloride, 7.7 mmol (15.4 eq.) of sodium sulfite and 7.7 mmol (15.4 eq.) of sodium hydrogenocarbonate in water is stirred at 100° C. for two hours. Then, 0.2 g (0.5 mmol, 1 eq.) of PCR8146 (obtained according to the procedure described in Remusat et al., *J. Heterocycl. Chem.* 2004, 41, 221-225) dissolved in 20 mL of dimethylsulfoxide is added to the solution. The mixture is stirred at 100° C. for two hours and poured into cold iced water. The crude precipitate obtained is washed several times with water and purified two times with the appropriate solvent.

Example 2: Synthesis of PCR9301

A solution of 1.4 mmol of butane sulfonyl chloride, 2.3 mmol (1.7 eq.) of sodium sulfite, 2.3 mmol (1.7 eq.) of sodium hydrogenocarbonate in 10 mL water is stirred under microwave irradiation at 300 watts for 45 minutes. Then, 0.5 g (1.4 mmol, 1 eq.) of 2-(bromomethyl)naphtho[2,3-d]oxazole-4,9-dione (obtained according to the procedure described Rathelot et al., Heterocycles 2000, 53, 1075-1084) dissolved in 30 mL of dimethysulfoxide is added to the solution. The mixture is stirred under microwave irradiation at 300 watts for 30 minutes and then poured into cold iced water. The crude precipitate obtained is filtrated and washed several times with water. After recrystallization in toluene, PCR9301 is obtained in 57% yield.

Example 3: Inhibition of USP8 and USP2 by benzo[g]quinoxaline-5,10-diones of the Invention Materials and Methods Protein Expression and Purification USP2CD or USP8CD were expressed in *E. coli* BL21 Gold. Cells were grown in LB Miller to mid-log phase and induced by addition of 0.5 mM IPTG for USP2CD for 5 h at 20° C., while 1 mM IPTG was added for USP8CD for 3 h at 37° C. Then, cells were harvested and frozen at −80° C.

For His-tagged USP8CD, cells were resuspended in buffer A (50 mM TRIS pH 8.0, 500 mM NaCl, 2 mM Imidazole) and lysed using a sonicator. The lysate was clarified by centrifugation and applied to Ni Sepharose6 Fast Flow resin (GE Healthcare). The resin was sequentially washed first with buffer A containing 10 mM Imidazole then with buffer A containing 20 mM Imidazole, and finally with buffer A containing 50 mM Imidazole. Protein sample was eluted from the resin using buffer A containing 300 mM Imidazole. The eluted protein was buffer exchanged by gel-filtration on a Superdex 200 10/300 GL column (GE Healthcare) equilibrated in Buffer B (20 mM HEPES pH 7.5, 300 mM NaCl, 2 mM dithiothreitol (DTT)).

For His-tagged USP2CD, cells were resuspended in buffer C (10 mM TRIS pH 8.0, 100 mM NaCl, 10 mM Imidazole) and lysed using a sonicator. The lysate was clarified by centrifugation and applied to Ni Sepharose6 Fast Flow resin (GE Healthcare). The resin was sequentially washed with buffer C, then with buffer C containing 50 mM Imidazole. Protein sample was eluted from the resin using buffer C containing 250 mM Imidazole. The eluted protein was buffer exchanged by gel-filtration on a Superdex 200 10/300 GL column (GE Healthcare) equilibrated in Buffer D (15 mM Bis-TRIS pH 6.0, 100 mM NaCl, 1 mM dithiothreitol (DTT)).

Protein concentrations were determined by measuring the absorbance at 280 nm using a molar extinction coefficient calculated from the amino acid sequence. Aliquots were flash-frozen in liquid $N_2$ and stored at −80° C.

Monitoring USP2 or USP8 Enzymatic Activity on Various Ubiquitin Substrates

The purified catalytic domain of USP2 ($USP2^{CD}$, in-house purified) or the purified full length USP2 (ref. 80352, BioSciences) or the purified catalytic domain of USP8 ($USP8^{CD}$, in-house purified) were used at a concentration of 2 nM ($USP2^{CD}$ or USP2-Full length) or 10 nM ($USP8^{CD}$) in the presence of the artificial substrate Ub-AMC (réf. U550 BostonBiochem) at a final concentration of 1 µM, or in the presence of Ub-Rhodamine 110 (Ub-Rho) (Ubiquigent réf.60-0117-050) at a final concentration of 0.1 µM. Enzymatic assay was performed in a HEPES buffer (50 mM pH7.6 1 mM DTT, 2% glycerol, 0.5 mM EDTA) or in a Tris buffer (40 mM pH7.4 1 mM DTT, 5% glycerol, 0.05 mg/ml BSA) respectively, following manufacturer's instructions. Compounds were added to the reaction mixture just prior to the substrate. The enzymatic reaction kinetics was monitored through the apparition of fluorescence due to the hydrolysis of the peptidyl Ub-AMC or Ub-Rho bound over 20 or 30 minutes. The negative control, showing no inhibiting activity on the enzyme, thereafter designed "bioinactive control" was the solvent DMSO at 1.5%. The positive control, mimicking the desired inhibitory activity, was the cystein protease inhibitor iodoacetamide (11149-5 g Sigma) at 1 mM final concentration in the case of USP2, or a mutated ubiquitin variant Ubv.8.2 (Ernst et al., 2013) at 1 µM final concentration in the case of USP8.

The degradation of purified lysine 63-linked tree-Ubiquitin chains (triUb$^{K63}$) over a 90 minutes period of time was visualized by western blot analysis. The $USP2^{CD}$ or the USP8CD were preincubated for 15 minutes at a concentration of 0.4 µM ($USP2^{CD}$) final or 0.5 µM ($USP8^{CD}$) with either DMSO or selected chemicals at indicated concentrations before the addition of triUb$^{K63}$ chains at a final concentration of 3.75 µM. Enzymatic assay was performed in a HEPES buffer (50 mM pH7.4, 150 mM NaCl, 0.5 mM EDTA, 2% glycerol, 0.2 mg/ml BSA, 5 mMDTT).

$IC_{50}$ Analysis

The $IC_{50}$ of PCR6236 and a number of derivatives was determined on in-house purified USP2CD or USP8CD at a concentration of 4 nM or 10 nM, respectively, in the presence of 0.1 µM Ub-Rhodamine 110 (Ubiquigent ref. 60-0117-050) or 1 µM Ub-AMC (Ubiquigent ref. 60-0116-050) as described above.

In additional assay, the $IC_{50}$ of PCR6236 was determined on full length purified enzymes USP2 and USP8 (Ubiquigent DUBprofiler™ Compound Screening Service). In these assays, an eight point half-log duplicate compound dilution curve was prepared starting at 100 µM PCR6236 and either USP2 or USP8 inhibition was monitored in the presence of 0.1 µM Ubiquitin-rhodamine 110 (assays are operating at <40% substrate conversion).

$IC_{50}$ data are reported as a percentage of the activity of the enzyme in the presence of the test compound relative to 'plus' (bioactive) (100% activity towards DUBs inhibition) and 'minus' (bioinactive) (0% activity towards DUB inhibition) controls. Medium value out of duplicates is reported.

Results

The inhibition of Ub-AMC hydrolysis by compounds of the invention were tested against USP2 full length (ref. 80352, BioSciences) at 50 µM, 25 µM, 5 µM and 1 µM average concentrations or purified $USP8^{CD}$ at 50 µM, 25 µM, 5 µM, 1 µM, 0.5 µM and 0.1 µM average concentrations using Ub-AMC at 1 µM (Table 1).

TABLE 1a

Assay of benzo[g]quinoxaline-5,10-diones of the invention against $USP2^{FL}$ and $USP8^{CD}$

| Compound | Structure | $USP2^{FL}$ % inhibition | | | | $USP8^{CD}$ % inhibition | | | | | |
|---|---|---|---|---|---|---|---|---|---|---|---|
| | | 50 µM | 25 µM | 5 µM | 1 µM | 50 µM | 25 µM | 5 µM | 1 µM | 0.5 µM | 0.1 µM |
| PCR6236 | | 101 | 94 | 65 | 34 | ND | ND | ND | 99 | 100 | 11 |

TABLE 1a-continued

Assay of benzo[g]quinoxaline-5,10-diones of the invention against USP2$^{FL}$ and USP8$^{CD}$

| | | USP2$^{FL}$ % inhibition | | | | USP8$^{CD}$ % inhibition | | | | | |
|---|---|---|---|---|---|---|---|---|---|---|---|
| Compound | Structure | 50 μM | 25 μM | 5 μM | 1 μM | 50 μM | 25 μM | 5 μM | 1 μM | 0.5 μM | 0.1 μM |
| PCR7986 | | 92 | 78 | 74 | 46 | 36 | ND | ND | ND | 13 | 1 |
| PCR7985 | | 95 | 59 | 49 | 33 | 98 | 61 | 23 | 55 | 20 | 1 |
| PCR7991 | | 93 | 94 | 79 | 46 | ND | ND | ND | 98 | 97 | 42 |
| PCR7993 | | 98 | 58 | 59 | 29 | 102 | 101 | 22 | 34 | 16 | 0 |

TABLE 1a-continued
Assay of benzo[g]quinoxaline-5,10-diones of the invention against USP2$^{FL}$ and USP8$^{CD}$
| Compound | Structure | USP2$^{FL}$ % inhibition | | | | USP8$^{CD}$ % inhibition | | | | | |
|---|---|---|---|---|---|---|---|---|---|---|---|
| | | 50 μM | 25 μM | 5 μM | 1 μM | 50 μM | 25 μM | 5 μM | 1 μM | 0.5 μM | 0.1 μM |
| PCR7996 | 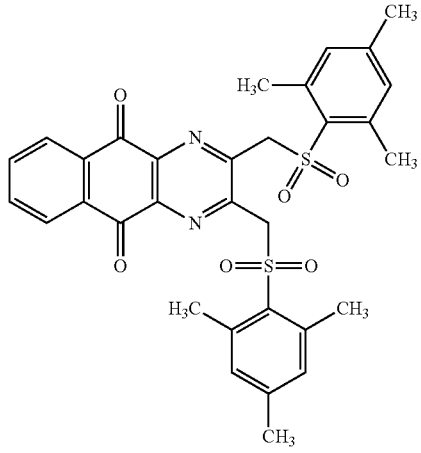 [SMILES: Cc1cc(C)c(S(=O)(=O)Cc2nc3c(nc2CS(=O)(=O)c2c(C)cc(C)cc2C)C(=O)c2ccccc2C3=O)c(C)c1] | 95 | 85 | 51 | 25 | 100 | 100 | 70 | 10 | ND | ND |
| PCR7997 | 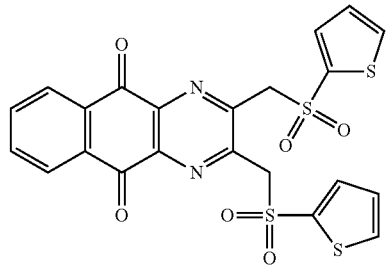 [SMILES: O=C1c2ccccc2C(=O)c2nc(CS(=O)(=O)c3cccs3)c(CS(=O)(=O)c3cccs3)nc21] | 99 | 70 | 22 | 0 | 100 | 97 | 61 | 13 | 3 | 17 |
| PCR8146 | 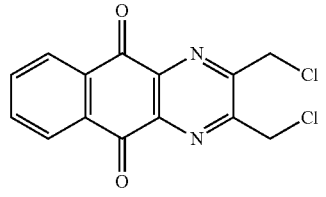 [SMILES: O=C1c2ccccc2C(=O)c2nc(CCl)c(CCl)nc21] | 99 | 89 | 50 | 30 | 100 | 90 | 43 | 6 | 35 | 11 |
| PCR8156 | 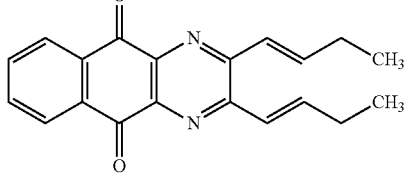 | 94 | 58 | 28 | 0 | 86 | 100 | 43 | 7 | 25 | 6 |
| PCR8153 | 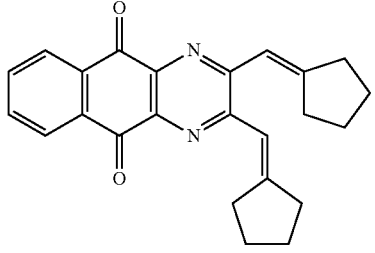 [SMILES: O=C1c2ccccc2C(=O)c2nc(C=C3CCCC3)c(C=C3CCCC3)nc21] | 98 | 98 | 54 | 8 | 100 | 100 | 22 | 0 | ND | ND |

TABLE 1b
Assay of benzo[g]quinoxaline-5,10-diones of the invention against USP2$^{CD}$ and USP8$^{CD}$
| Compound | Structure | USP2$^{CD}$ % inhibition | | | | USP8$^{CD}$ % inhibition | | | |
|---|---|---|---|---|---|---|---|---|---|
| | | 50 μM | 25 μM | 5 μM | 1 μM | 50 μM | 25 μM | 5 μM | 1 μM |
| PCR7994 | 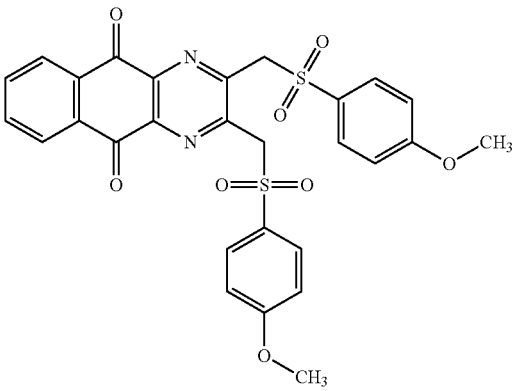 [SMILES: COc1ccc(S(=O)(=O)Cc2nc3c(nc2CS(=O)(=O)c2ccc(OC)cc2)C(=O)c2ccccc2C3=O)cc1] | 50 | 53 | 22 | −9 | 100 | 91 | 68 | 62 |
| OVM13 | 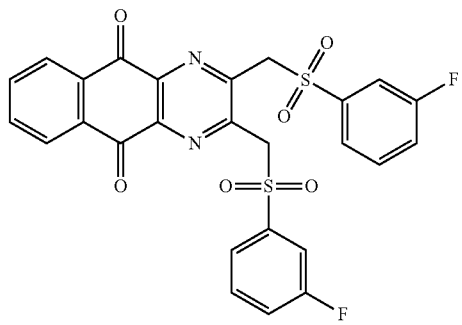 [SMILES: O=C1c2ccccc2C(=O)c2nc(CS(=O)(=O)c3cccc(F)c3)c(CS(=O)(=O)c3cccc(F)c3)nc21] | 41 | 66 | 48 | 17 | 94 | 102 | 88 | 60 |
| OVM15 | 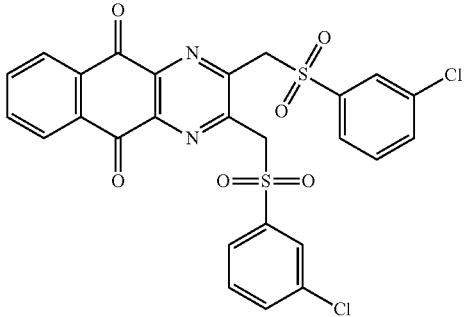 [SMILES: O=C1c2ccccc2C(=O)c2nc(CS(=O)(=O)c3cccc(Cl)c3)c(CS(=O)(=O)c3cccc(Cl)c3)nc21] | 30 | 16 | 1 | 0 | 83 | 70 | 51 | 68 |
| OVM16 | 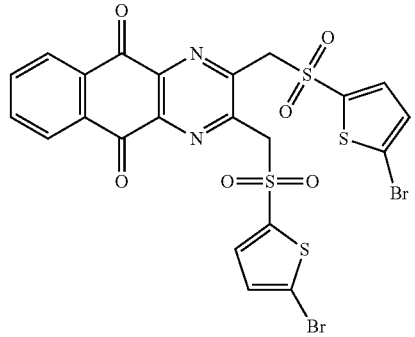 [SMILES: O=C1c2ccccc2C(=O)c2nc(CS(=O)(=O)c3ccc(Br)s3)c(CS(=O)(=O)c3ccc(Br)s3)nc21] | 80 | 42 | 26 | 1 | 104 | 92 | 56 | 10 |

TABLE 1b-continued

Assay of benzo[g]quinoxaline-5,10-diones of the invention against USP2$^{CD}$ and USP8$^{CD}$

| Compound | Structure | USP2$^{CD}$ % inhibition | | | | USP8$^{CD}$ % inhibition | | | |
|---|---|---|---|---|---|---|---|---|---|
| | | 50 μM | 25 μM | 5 μM | 1 μM | 50 μM | 25 μM | 5 μM | 1 μM |
| OVM17 | 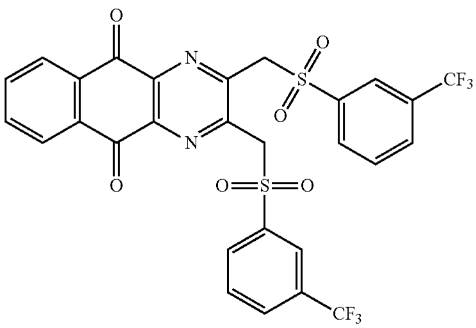 [SMILES: O=C1c2ccccc2C(=O)c2nc(CS(=O)(=O)c3cccc(C(F)(F)F)c3)c(CS(=O)(=O)c3cccc(C(F)(F)F)c3)nc21] | 25 | 27 | 9 | −11 | 85 | 68 | 33 | 25 |
| OVM18 | 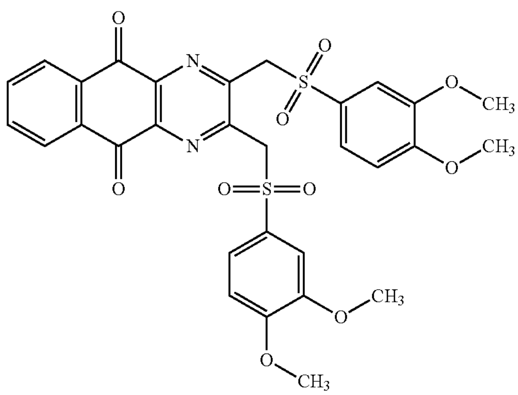 [SMILES: COc1ccc(S(=O)(=O)Cc2nc3c(nc2CS(=O)(=O)c2ccc(OC)c(OC)c2)C(=O)c2ccccc2C3=O)cc1OC] | 63 | 53 | ND | 53 | 101 | 96 | 103 | 100 |
| OVM19 | 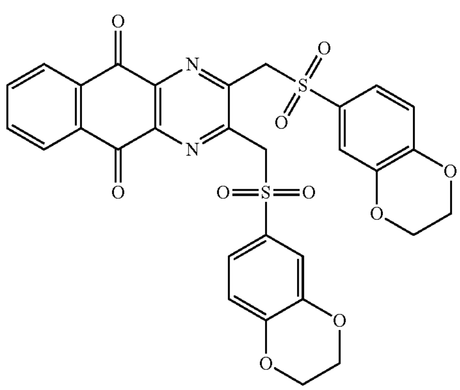 [SMILES: O=C1c2ccccc2C(=O)c2nc(CS(=O)(=O)c3ccc4c(c3)OCCO4)c(CS(=O)(=O)c3ccc4c(c3)OCCO4)nc21] | 18 | 21 | 25 | 20 | 77 | 76 | 61 | 53 |
| OVM23 | 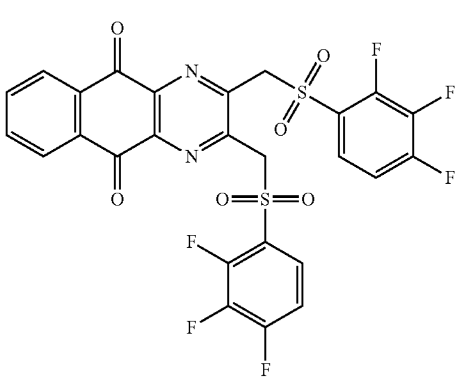 [SMILES: O=C1c2ccccc2C(=O)c2nc(CS(=O)(=O)c3ccc(F)c(F)c3F)c(CS(=O)(=O)c3ccc(F)c(F)c3F)nc21] | 97 | 94 | 53 | 69 | 103 | 100 | 92 | 83 |

TABLE 1b-continued

Assay of benzo[g]quinoxaline-5,10-diones of the invention against USP2$^{CD}$ and USP8$^{CD}$

| Compound | Structure | USP2$^{CD}$ % inhibition | | | | USP8$^{CD}$ % inhibition | | | |
| --- | --- | --- | --- | --- | --- | --- | --- | --- | --- |
| | | 50 μM | 25 μM | 5 μM | 1 μM | 50 μM | 25 μM | 5 μM | 1 μM |
| OVM24 | 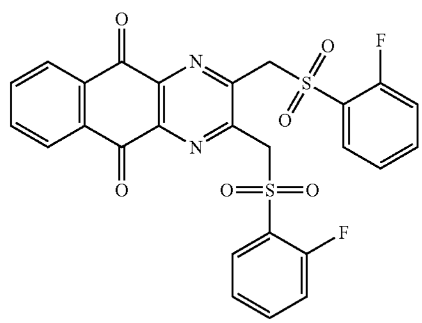 [SMILES: O=C1c2ccccc2C(=O)c2nc(CS(=O)(=O)c3ccccc3F)c(CS(=O)(=O)c3ccccc3F)nc21] | 96 | 86 | 68 | 54 | 103 | 115 | 103 | 64 |
| VIN6074 | 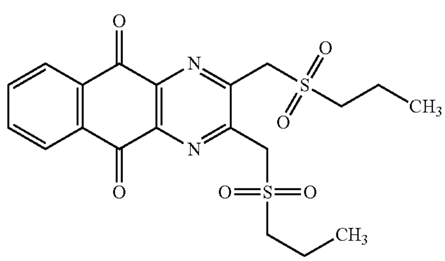 [SMILES: CCCS(=O)(=O)Cc1nc2c(nc1CS(=O)(=O)CCC)C(=O)c1ccccc1C2=O] | 101 | 98 | 81 | 38 | 107 | 100 | 98 | 93 |
| VIN6075 | 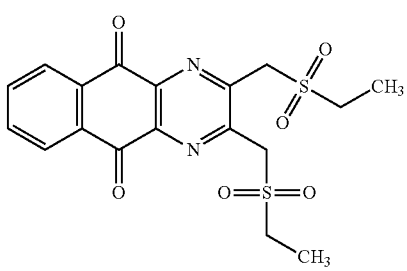 [SMILES: CCS(=O)(=O)Cc1nc2c(nc1CS(=O)(=O)CC)C(=O)c1ccccc1C2=O] | 100 | 99 | 75 | 51 | 106 | 104 | 102 | 85 |
| VIN6076 | 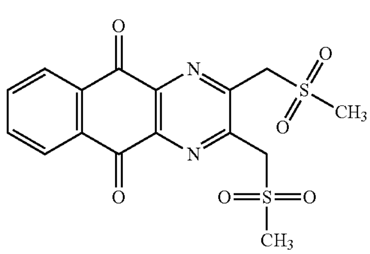 [SMILES: CS(=O)(=O)Cc1nc2c(nc1CS(C)(=O)=O)C(=O)c1ccccc1C2=O] | 97 | 95 | 66 | 23 | 103 | 106 | 100 | 77 |
| VIN6077 | 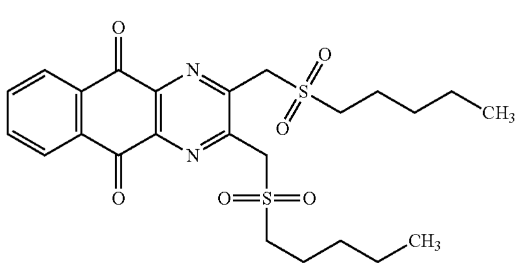 [SMILES: CCCCCS(=O)(=O)Cc1nc2c(nc1CS(=O)(=O)CCCCC)C(=O)c1ccccc1C2=O] | 76 | 63 | 51 | 24 | 100 | 101 | 94 | 54 |

TABLE 1c

Assay of benzo[g]quinoxaline-5,10-diones of the invention against USP2$^{CD}$

| Compound | Structure | USP2$^{CD}$ % inhibition | | | | | | |
|---|---|---|---|---|---|---|---|---|
| | | 10 μM | 5 μM | 1 μM | 0.5 μM | 0.1 μM | 0.05 μM | 0.01 μM |
| PCR7994 | 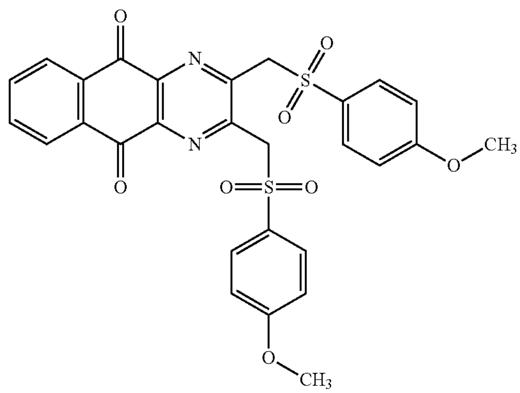 [SMILES: COc1ccc(S(=O)(=O)Cc2nc3c(nc2CS(=O)(=O)c2ccc(OC)cc2)C(=O)c2ccccc2C3=O)cc1] | 17 | 8 | 5 | 26 | 2 | −12 | −8 |
| OVM13 | 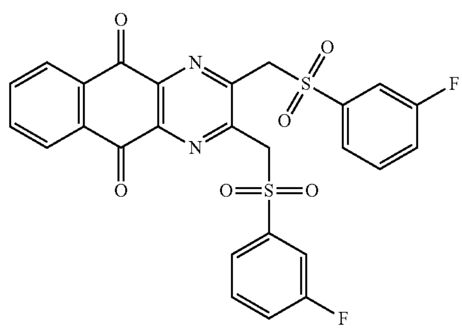 [SMILES: O=C1c2ccccc2C(=O)c2nc(CS(=O)(=O)c3cccc(F)c3)c(CS(=O)(=O)c3cccc(F)c3)nc21] | 1 | 10 | −6 | −3 | −32 | −20 | 9 |
| OVM15 | 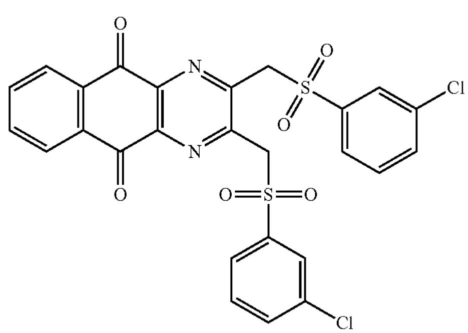 [SMILES: O=C1c2ccccc2C(=O)c2nc(CS(=O)(=O)c3cccc(Cl)c3)c(CS(=O)(=O)c3cccc(Cl)c3)nc21] | 17 | −10 | 37 | 23 | 3 | 3 | 19 |
| OVM18 | 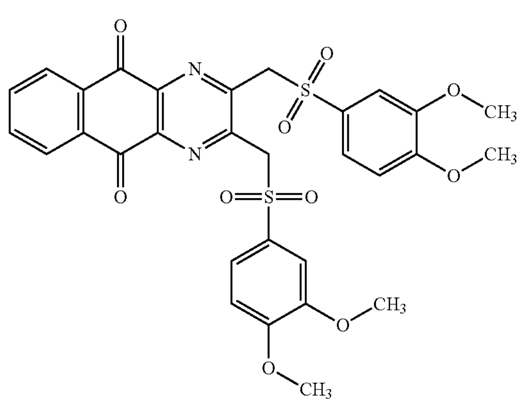 [SMILES: COc1ccc(S(=O)(=O)Cc2nc3c(nc2CS(=O)(=O)c2ccc(OC)c(OC)c2)C(=O)c2ccccc2C3=O)cc1OC] | 9 | 17 | 44 | −20 | 19 | −3 | −19 |

TABLE 1c-continued

Assay of benzo[g]quinoxaline-5,10-diones of the invention against USP2$^{CD}$

| Compound | Structure | USP2$^{CD}$ % inhibition |||||||
|---|---|---|---|---|---|---|---|---|
| | | 10 μM | 5 μM | 1 μM | 0.5 μM | 0.1 μM | 0.05 μM | 0.01 μM |
| OVM19 | 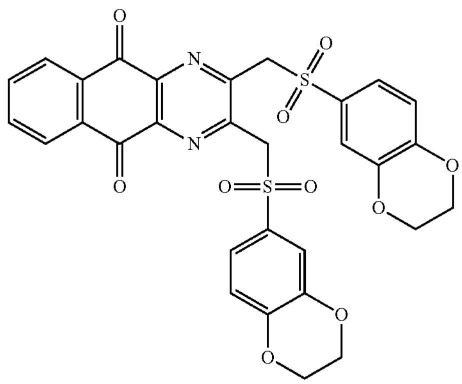 [SMILES: O=C1c2ccccc2C(=O)c2nc(CS(=O)(=O)c3ccc4c(c3)OCCO4)c(CS(=O)(=O)c3ccc4c(c3)OCCO4)nc21] | 11 | −3 | 9 | −1 | 13 | −14 | −19 |
| OVM23 | 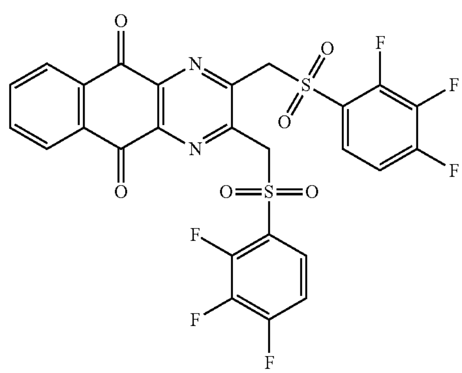 [SMILES: O=C1c2ccccc2C(=O)c2nc(CS(=O)(=O)c3ccc(F)c(F)c3F)c(CS(=O)(=O)c3ccc(F)c(F)c3F)nc21] | 4 | −1 | 18 | 16 | −22 | −26 | −20 |
| OVM24 | 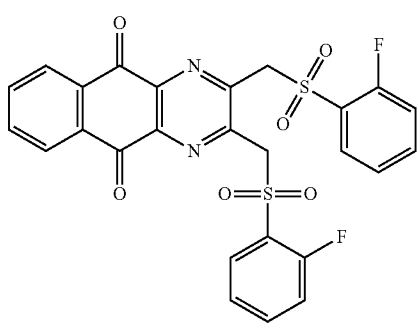 [SMILES: O=C1c2ccccc2C(=O)c2nc(CS(=O)(=O)c3ccccc3F)c(CS(=O)(=O)c3ccccc3F)nc21] | 17 | 20 | 12 | 10 | 9 | 2 | −29 |
| VIN6074 | 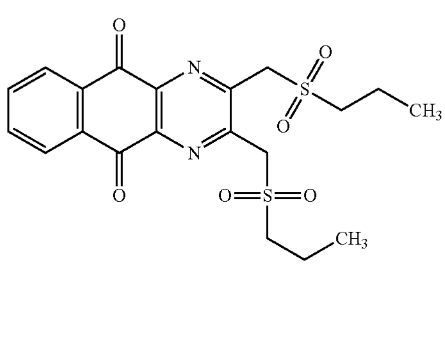 [SMILES: CCCS(=O)(=O)Cc1nc2c(nc1CS(=O)(=O)CCC)C(=O)c1ccccc1C2=O] | 77 | 70 | 17 | 23 | −23 | −13 | 1 |

TABLE 1c-continued

Assay of benzo[g]quinoxaline-5,10-diones of the invention against USP2$^{CD}$

| Compound | Structure | USP2$^{CD}$ % inhibition | | | | | | |
|---|---|---|---|---|---|---|---|---|
| | | 10 μM | 5 μM | 1 μM | 0.5 μM | 0.1 μM | 0.05 μM | 0.01 μM |
| VIN6075 | 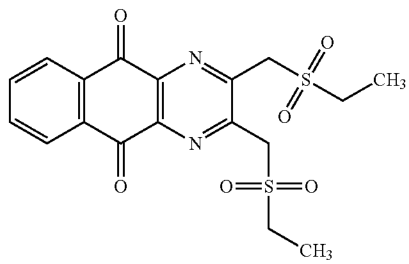 [SMILES: CCS(=O)(=O)Cc1nc2c(nc1CS(=O)(=O)CC)C(=O)c1ccccc1C2=O] | 57 | 51 | 31 | 2 | −26 | 6 | 11 |
| VIN6076 | 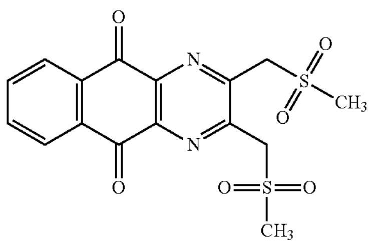 [SMILES: CS(=O)(=O)Cc1nc2c(nc1CS(C)(=O)=O)C(=O)c1ccccc1C2=O] | 56 | 19 | 57 | 6 | 4 | −7 | 17 |
| VIN6077 | 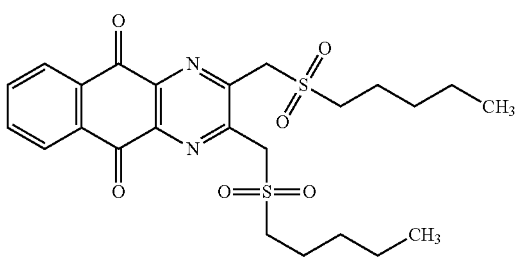 [SMILES: CCCCCS(=O)(=O)Cc1nc2c(nc1CS(=O)(=O)CCCCC)C(=O)c1ccccc1C2=O] | 27 | 20 | −17 | 11 | −13 | −16 | −11 |

TABLE 1d

Assay of benzo[g]quinoxaline-5,10-diones of the invention against USP8$^{CD}$

| Compound | Structure | USP8 CD % inhibition | | | | | | |
|---|---|---|---|---|---|---|---|---|
| | | 10 μM | 5 μM | 1 μM | 0.5 μM | 0.1 μM | 0.05 μM | 0.01 μM |
| PCR7994 | 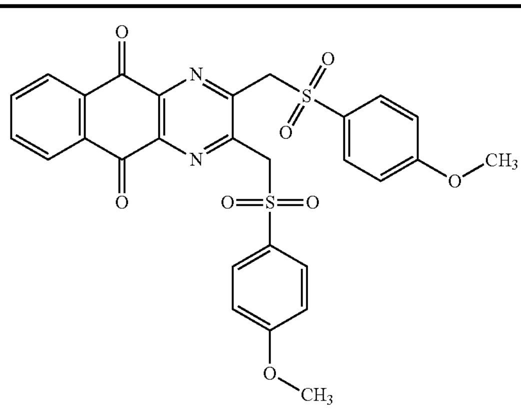 | 73 | 52 | 31 | 18 | −23 | −13 | −7 |

TABLE 1d-continued

Assay of benzo[g]quinoxaline-5,10-diones of the invention against USP8$^{CD}$

| Compound | Structure | USPS CD % inhibition ||||||| 
| | | 10 μM | 5 μM | 1 μM | 0.5 μM | 0.1 μM | 0.05 μM | 0.01 μM |
|---|---|---|---|---|---|---|---|---|
| OVM13 | | 35 | 76 | 65 | 44 | −9 | 3 | −22 |
| OVM15 | | 51 | 52 | 64 | 18 | 14 | 16 | 24 |
| OVM18 | | 71 | 77 | 83 | 63 | −8 | 21 | 2 |
| OVM19 | | 54 | 46 | 44 | 17 | −9 | −5 | −22 |

TABLE 1d-continued

Assay of benzo[g]quinoxaline-5,10-diones of the invention against USP8[CD]

| Compound | Structure | USP8 CD % inhibition | | | | | | |
|---|---|---|---|---|---|---|---|---|
| | | 10 μM | 5 μM | 1 μM | 0.5 μM | 0.1 μM | 0.05 μM | 0.01 μM |
| OVM23 | | 80 | 74 | 34 | 20 | 24 | 12 | −5 |
| OVM24 | | 97 | 78 | 74 | 65 | 7 | 3 | −25 |
| VIN6074 | | 99 | 103 | 93 | 67 | 0 | 16 | −17 |
| VIN/6075 | | 110 | 104 | 86 | 51 | 12 | 24 | −15 |
| VIN6076 | | 98 | 90 | 85 | 47 | 30 | 14 | 27 |

TABLE 1d-continued

Assay of benzo[g]quinoxaline-5,10-diones of the invention against USP8$^{CD}$

| | | USPS CD % inhibition | | | | | | |
|---|---|---|---|---|---|---|---|---|
| Compound | Structure | 10 μM | 5 μM | 1 μM | 0.5 μM | 0.1 μM | 0.05 μM | 0.01 μM |
| VIN6077 | [structure] | 91 | 100 | 44 | 26 | 26 | −2 | 19 |

TABLE 2a

IC$_{50}$ values of PCR6236 and PCR7991 against purified USP8$^{CD}$ or USP2$^{CD}$ or full length (FL) USP8 or USP2 with Ub-Rhodamine substrate (IC$_{50}$ are given in μM)

| | PCR6236 | PCR7991 |
|---|---|---|
| USP8$^{CD}$ | 0.06 | 0.05 |
| USP2$^{CD}$ | 2.10 | 1.70 |
| USP8-FL | <0.03 | ND |
| USP2-FL | 0.20 | ND |

TABLE 2b

IC$_{50}$ values against purified USP8$^{CD}$ or USP2$^{CD}$ with Ub-AMC substrate at 1 μM (IC$_{50}$ are given in μM)

| Compound | USP2 CD | USP8 CD |
|---|---|---|
| PCR7994 | >10 μM | 5 μM |
| OVM13 | >10 μM | 0.4 μM |
| OVM15 | >10 μM | 0.4 μM |
| OVM18 | >10 μM | 0.5 μM |
| OVM19 | >10 μM | 7.5 μM |
| OVM23 | >10 μM | 2.2 μM |
| OVM24 | >10 μM | 0.4 μM |
| VIN6074 | 3 μM | 0.3 μM |
| VIN6075 | 5 μM | 0.5 μM |
| VIN6076 | >10 μM | 0.5 μM |
| VIN6077 | >10 μM | 1.2 μM |
| PCR8146 | 6 μM | 2.1 μM |
| PCR8132 | 17 μM | 4.5 μM |

PCR8132 is of the following formula:

TABLE 2c

IC$_{50}$ values against purified USP8$^{CD}$ or USP2$^{CD}$ with Ub-Rhodamine substrate at 0.1 μM (IC$_{50}$ are given in μM)

[structure]

| Compound | USP2 CD | USP8 CD |
|---|---|---|
| PCR7994 | ND | ND |
| OVM13 | ND | 0.4 μM |

TABLE 2c-continued

IC$_{50}$ values against purified USP8$^{CD}$ or USP2$^{CD}$ with Ub-Rhodamine substrate at 0.1 μM (IC$_{50}$ are given in μM)

[structure]

| Compound | USP2 CD | USP8 CD |
|---|---|---|
| OVM15 | ND | 0.4 μM |
| OVM18 | ND | ND |
| OVM19 | ND | ND |
| OVM23 | ND | ND |
| OVM24 | ND | 2.3 μM |
| VIN6074 | 0.5 μM | 0.04 μM |
| VIN6075 | 0.6 μM | 0.08 μM |
| VIN6076 | 0.65 μM | 0.01 μM |
| VIN6077 | ND | ND |

In particular, compounds having a % of inhibition towards USP8 and USP2 above 50, at 25 M, are considered as active towards USP8 and/or USP2 respectively.

In particular, compounds having an IC50 below 10 μM are considered as active towards USP8 and/or USP2 respectively.

In particular, if there is at least one concentration for which a compound has a % of inhibition towards USP2 being at least 10 times greater than the % of inhibition towards USP8 and optionally towards other deubiquitinases, then said compound may be considered as selective for or preferentially inhibiting USP2.

In particular, if there is a 10 times lower IC50 towards USP8 as compared to USP2 and optionally to other deubiquitinases, then said compound is considered as selective for or preferentially inhibiting USP8.

Example 4: Inhibition of USP8 and USP2 by PCR9301 of the Invention

The inhibitory potential of PCR9301 was measured by direct monitoring of its inhibitory potential against USP2$^{CD}$ or USP8$^{CD}$ (table 3).

TABLE 3a

Assay of PCR9301 against USP2$^{CD}$ and USP8$^{CD}$

| Compound identifier | Structure | USP2$^{CD}$ % inhibition | | | | USP8$^{CD}$ % inhibition | | |
|---|---|---|---|---|---|---|---|---|
| | | 50 μM | 25 μM | 5 μM | 1 μM | 1 μM | 0.5 μM | 0.1 μM |
| PCR9301 | [structure] | 100 | 100 | 99 | 77 | 107 | 81 | 53 |

TABLE 3b

IC$_{50}$ values of PCR9301 against purified USP8$^{CD}$ or USP2$^{CD}$ with Ub-Rho substrate (IC$_{50}$ are given in μM)

| | PCR9301 |
|---|---|
| USP8$^{CD}$ | 0.08 μM |
| USP2$^{CD}$ | 0.4 +/− 0.1 μM |

Example 5: Cytotoxicity of PCR6236 and PCR9301 on Human Cancerous Cell Lines Including Chemo-Resistant Cells Materials and Methods Messa, Messa DX5, HCT116, HEK-293, PC-3, LNCaP, HCC827 and H1975 cell lines are issued from the American Type Culture Collection (ATCC).

Messa, Messa DX5 and HCT116 were maintained in McCoy's supplemented with 10% fetal bovine serum, and 1% penicillin/streptomycin. PC-3, LNCaP cells were maintained in RPMI medium supplemented with 10% fetal bovine serum, and 1% penicilin/streptomycin and in the case of Messa DX5: 500 nM Doxorubicin was added to maintain selection pressure. HEK293 were maintained in DMEM medium supplemented with 10% fetal bovine serum, and 1% penicillin/streptomycin. Cells were maintained at 37° C. with 5% CO2, 95% air, and humid atmosphere. In the case of hormonal dependent LNCaP cells, 2 μM DiHydroTestosterone (DHT) was added or not—depending on the type of biological assay—for the same incubation period as compounds.

The cell growth inhibition and cell death induction of non-small cell lung cancers (NSCLC), HCC827 cells and derivative Gefitinib-resistant clone H1975 were monitored during a period of 72 hours using Incucyte microscope and dedicated programs allowing to monitor cell confluency (i.e.: cell surface area relative to total well surface) and cell death induction by adding Propidium Iodide (PI) at 1 μg/ml (Sigma Aldrich #P4864) in the culture medium. Similar procedure was used to analyze cell growth inhibition and cell death induction during a period of 48 hours by PCR6236 and two highly active analogs OVM24 and VIN6074 on PC-3 and LNCaP prostatic cancer cells For cytotoxicity assays, cells were seeded in 96-well microplates 24 hours before the addition of increasing concentrations of each compound in the culture medium. Cell viability was analyzed 48 hours following addition of each compound through the monitoring of mitochondrial ATPase activity using PrestoBlue® Cell Viability Reagent (Invitrogen; #A-13261). Paclitaxel was used as a control which is cytotoxic on various cancerous cells although not on chemoresistant MESSA DX5 lineage.

Results

PCR6236 and PCR9301 inhibit cell growth and induce cell death in a dose dependent manner in both HCC827 and Gefitinib resistant H1975 cells. This suggests that PCR6236 can counteract Gefitinib resistance in cancer treatment (FIG. 12 A,B)

PCR6236, OVM24 and VIN6074 inhibit cell growth and induce cell death in a dose dependent manner in both PC-3 and LNCaP cells.

The cytotoxicity of PCR6236 and PCR9301 on various cancerous cells was further monitored following 48 h drug treatment at eight doses in order to determine the efficient concentration inducing 50% cell mortality (EC$_{50}$) (Table 4).

TABLE 4

Cellular toxicity of PCR6236 and PCR9301 at 48 hours treatment compared to Paclitaxel and of other analogs

| EC$_{50}$ | MESSA | MESSA DX5 | HEK293 | HCT116 | PC-3 | LNCaP | H1975 | HCC827 |
|---|---|---|---|---|---|---|---|---|
| PCR6236 | 2.0 μM +/− 0.4 μM | 3.5 μM +/− 0.7 μM | 1.4 μM +/− 0.1 μM | 1.3 μM +/− 0.4 μM | 0.8 μM +/− 0.4 μM | 2.0 μM +/− 0.5 μM | 3 μM +/− 0.1 μM | 1.8 μM +/− 0.1 μM |
| PCR9301 | 1.3 μM +/− 0.5 μM | 1.8 μM +/− 0.2 μM | ND | 1.7 μM +/− 0.4 μM | 1.0 μM +/− 0.5 μM | 1.3 μM +/− 0.3 μM | ND | ND |
| Paclitaxel | 1.5 μM | >100 μM | ND | ND | ND | ND | ND | ND |
| OVM 18 | 1.3 μM +/− 0.2 μM | 2.5 μM +/− 0.4 μM | 2.5 μM +/− 0.1 μM | ND | 3.0 μM +/− 0.1 μM | 2.1 μM +/− 0.1 μM | >3 μM +/− 0.1 μM | ND |

TABLE 4-continued

Cellular toxicity of PCR6236 and PCR9301 at 48 hours treatment compared to Paclitaxel and of other analogs

| $EC_{50}$ | MESSA | MESSA DX5 | HEK293 | HCT116 | PC-3 | LNCaP | H1975 | HCC827 |
|---|---|---|---|---|---|---|---|---|
| OVM 24 | 0.7 µM +/− 0.1 µM | 0.8 µM +/− 0.2 µM | 2.5 µM +/− 0.1 µM | ND | 2.5 µM +/− 0.4 µM | 1.3 µM +/− 0.2 µM | 2 µM +/− 0.1 µM | ND |
| VIN 6074 | 2.7 µM +/− 0.5 µM | 3.5 µM +/− 1.5 µM | 1.5 µM +/− 0.1 µM | ND | 2.3 µM +/− 0.5 µM | 1.9 µM +/− 0.1 µM | 2 µM +/− 0.1 µM | ND |
| YIN 6075 | 3.0 µM +/− 0.5 µM | >3 µM +/− 0.1 µM | >3 µM +/− 0.1 µM | ND | 3.0 µM +/− 0.5 µM | 2.8 µM +/− 0.1 µM | >3 µM +/− 0.1 µM | ND |

The two compounds PCR6236 and PCR9301 induced cells death with an $EC_{50}$ ranging from 1 µM to 3.5 µM in all cancerous cells tested. As expected, high concentration of paclitaxel treatment (100 µM) did not induce MESSA-DX5 cells death, where these cells are known to be resistant to paclitaxel treatment (Table 4). In contrast, the chemo-resistant MESSA-DX5 were equally sensitive to PCR6236 or PCR9301 as their nonresistant counterpart MESSA cell line indicating that these two drugs may overcome chemo-resistance. PCR6236 and a number of derivatives also induced death of Gefitinib resistant cells H1975 with an EC50 of 3 µM or less.

Example 6: Cancerous Cell Death Induced by PCR6236 and PCR9301 in 3D Model Systems Materials and Methods For 3D cell culture (spheroids), the LNCaP-FGC (fast growing colony) cell line (ATCC #CRL1740) was used. This cell line derives from the LNCaP cell line (Human Prostatic Carcinoma) which shares all the main characteristics, including its androgen sensitivity, described for the parental line and HCT116 (ATCC #CCL 247) (Human Colorectal Carcinoma) cell lines.

Cells were cultured in 96-well tissue culture plate poly-HEMA-coated U-bottom with low evaporation Lid (Plates 96 wells round bottom culture in suspension Cellstar Greiner Bio-One #650185) to allow the formation of spheroids. Prostatic cancer cells LNCaP (taken from exponentially growing cultures) were seeded at a density of $2.8 \times 10^4$ cells/ml in RPMI-1640 Glutamax medium (GIBCO #61870-010). Colorectal cancer cells HCT116 (taken from exponentially growing cultures) were seeded at a density of $1.1 \times 10^4$ cells/ml in Mc Coy's 5A medium (GIBCO #26600-080). Media were supplemented with 10% FCS, and 1% Penicillin/Streptomycin. Then, 90 µL of each cell suspension were added in the corresponding wells and centrifuged at 400 g during 5 min. Microplates were then incubated at 37° C. and 5% $CO_2$ for 3 days before drug treatment (at this moment, 10 µl of 10 times concentrated drug (at various concentration) were added in corresponding well for the indicated time.

An automated imaging protocol was designed to monitor the induction of cell death in the spheroids by high content analysis methods (HCA). 3 hours before reading, cells were labeled with vital Hoechst (400 ng/ml) (Thermo Fischer Scientific #33342) and Propidium Iodide (PI) at 1 µg/ml (Sigma Aldrich #P4864) as markers of cell nuclei and cell death respectively. Images of PI and Hoechst fluorescence were acquired using the automated microscope Array-Scan$^{VTI}$ (ThermoScientific) and 5 times magnification. Bio-Application Colocalization (HCS Studio software) has been used to automatically extract features of interest as spheroid area. This methodology has been applied to 72 h old spheroids treated with increasing doses of either PCR6236 or PCR9301 for either 24 h or 48 h. Pictures of one to seven days old LNCaP spheroids were independently acquired on a Zeiss Observer Z1 microscope.

In vitro migration out of the spheroid was performed using a 96-well tissue culture plate (Cell Culture Microplate, 96 wells, Flat-BOTTOM, CellStar #655090). 100 µL (72 h hours old+24 h drug treatment spheroids) were placed in corresponding well of the new flat microplate, and daily observed in bright field with a Zeiss Axio Observer microscope. Each condition was made in six replicates. The migration area was measured with the tools of the AxioObserver software.

Results

There are growing evidences that tumor cell aggregates or spheroids produced in three-dimensional (3D) systems are more representative of in vivo tumors. They exhibit several physiological traits including similar morphology, formation of cell-cell bonds, decreased proliferation rates, increased cell survival, and a hypoxic core. Spheroid model thus associates malignant-cell microenvironment and 3D organization to better mimic avascular tumors (Vinci et al. (2013), Methods in molecular biology 986, 253-266). The published protocols of multicellular tumor spheroid were adapted to the LNCaP cell line. Spheroids were treated with Hoechst to stain DNA and with Propidium Iodure (PI) to stain dead cells (FIG. 2A,B).

An automated imaging protocol was designed to monitor the induction of cell death in the spheroids by high content analysis methods (HCA). Spheroids were observed from 1 to 3 days with optional treatment with either PCR6236 or PCR9301 at increasing concentration (FIG. 2C). Monitoring of IP area over Hoechst area indicated a significant induction of a tumorous cells death in spheroids treated with PCR6236 and to an ever higher extend with PCR9301 (FIG. 2C).

Example 7: PCR6236 Prevents Cell Migration Out of 3D Spheroids and Cell Spreading in a Wounding Assay In order to evaluate the anti-metastatic potential of PCR6236, the 3D spheroid models system was advantageously used to monitor the invasiveness and migration ability of cancerous cells. To this end, 3-days old spheroids are placed in a new flat-well microplate and daily observed in bright field. Migration area was monitored from 1 to 7 days after spheroids transfer revealing strong capacity of PCR6236 at both 2 µM and 5 µM to prevent cell migration out of the spheroids (FIG. 3).

In addition the migratory capacity of two additional triple negative breast cancer cells lines: the metastatic MDA-MB231 and BT-549 showing high migratory capacity was analyzed in a classical wound assay.

Method of the Wounding Assay

BT-549, MDA-MB231 cell lines were issued from the American Type Culture Collection (ATCC). For wounding assays, cells were seeded in 24-well microplates (Culture Insert 21, ref 250210, Ibidi®). After 24 hours, the gap was removed following manufacturer instructions before the addition of increasing concentrations of PCR6236 in the culture medium in the presence of mitomycine at 2 µg/ml to prevent cell proliferation. Cell spreading was then visualized during 24 hours by videomicroscopy (1 acquisition each 30 min). A representative picture of 3 is presented at 0 and 12 hours of drug treatment out. In Graphs, curves represents the empty surface (devoid of cells) between the two cell layers (delimited by using Image J software).

Results (FIGS. 9A and 9B)

PCR6236 prevents triple negative breast cancer cell migration from 1 µM concentration.

Example 8: In Vivo Anti-Tumorigenic Properties of PCR6236 on Chicken Embryonic Xenograft Tumors Materials and Methods Anti-tumorigenic potential of PCR6236 was assayed on in ovo induced tumors. Fertilized White Leghorn eggs were incubated at 37.5° C. with 50% relative humidity for 9 days. At this time (E9), the chorioallantoic membrane (CAM) was dropped by drilling a small hole through the eggshell into the air sac and a 1 cm² window was cut in the eggshell above the CAM. Twenty one eggs were used for each condition.

Prior to xenografting, PC-3 cells were cultivated in F12K medium with 10% of fetal bovine serum (and 1% penicillin/ streptomycin). Cells were detached with trypsin, washed with complete medium, labeled and suspended in PBS. An inoculum of $3 \cdot 10^6$ cells was added onto the CAM of each egg (E9). Eggs were then randomized in 4 groups.

At day 10 (E10), tumors began to be detectable. They were then treated during 10 days, every two days (E10, E12, E14, E16, and E18) by dropping 100 µl of vehicle (RPMI), Vinorelbine (reference compound at 1 µM) or compound PCR6236 (STU20151116) at 2 µM onto the tumor.

At day 19 (E19) the upper portion of the CAM was removed, transferred in PBS and the tumors were then carefully cut away from normal CAM tissue. Tumors were then weighted. A one-way ANOVA analysis (for nonparametric tests) with post-tests (Dunns test) has been done on these data.

In parallel, a 1 cm² portion of the lower CAM was collected to evaluate the number of metastatic cells. Genomic DNA is extracted from the CAM, and analyzed by qPCR with specific primers for Alu sequences. Stat analysis was directly done with the Bio-Rad CFX Manager 3.1 software.

The number of dead embryo evaluates the toxicity after 10 days of the treatment as well as the research of abnormality on 22 checkpoints observed on surviving embryos at two concentrations of drugs (i.e. 2 µM and 10 µM).

Head: Size, Closure, Eyes, Ear, Face and Branchial are derivatives, Mobility;

Body: Size, Axis deformation, ventral and dorsal Closures, Caudal formation, Sexual area;

Limbs: Size, Axis morphology, Mobility,

Skin: Appendage formation, Attachment, Blood vessel;

Extra-Embryonic Structures: Vascularisation, Transparency, Attachment, Blood vessel Results Using chick embryo for xenografting of human cancerous cells provides a unique model that overcomes many limitations associated with experimentations on mammalian models. The well-vascularized extra-embryonic tissue located underneath the eggshell allows for tumor growth and metastatic cells observation and monitoring after tumour cells xenografting (FIG. 4A). Moreover, it has been well demonstrated that the avian xenograft recapitulates cancer cell characteristics including growth, invasion, angiogenesis, and remodeling of the microenvironment. No significant toxicity of PCR6236 was observed in the chick embryo model: no death and no macroscopic abnormalities were detected in the head, body, limbs, skin, and extraembryonic annexes of chicken embryos treated with PCR6236 each second day neither at 2 µM nor at 10 µM (FIG. 4B).

When tested on PC-3 xenograft tumors induced in chick embryos, the PCR6236 compound applied each second day at 2 µM had a significant effect on tumor growth (27 to 30% reduction) (FIG. 4C). This effect is also visible on metastasis invasion (40 to 60% reduction) (FIG. 4D). There results show a potent anti-tumorigenic potential of PCR6236 in vivo.

Example 9: Stability on Human and Murine Microsomes

The metabolic stability of the compounds PCR6236 and PCR9301 was monitored on suspended liver cells (microsomes) (0.25 mg/mL) of human (NC, Mixed Gender Pooled 20-donor, Corning) or mouse (CD-1, Male Pooled 500-mice, Corning) at a concentration of 0.5 µM for 0 min, 5 min, 15 min and 30 min incubation times. Each compound was incubated either with cofactors (n=2) or without cofactors (n=1). Positive controls were: Diclofenac, Midazolam and Amitriptyline.

Important interspecies difference was evidenced for the cofactors (CYP)-mediated metabolism of the compound PCR6236 which turned to be high in mouse while low in human cells. In contrast, the compound PCR9301 was not or poorly metabolized in neither human nor mice microsomes. No metabolism was observed in the absence of cofactors or the two compounds (FIG. 5).

Example 10: Modification of the Expression Levels of Oncogenic Proteins and of the Tumor Suppressor p53 in Human Cells by PCR6236

Observation of Protein Expression by Western Bot Analysis

Cells were treated by either DMSO (0.5%) or increasing doses of the selected molecules from 1 µM to 10 µM over 6 to 24 hours as indicated. Cell lysates were analyzed by immunoblotting following standard procedure using primary antibodies from Cell Signaling: anti-total P53 (#9282), anti-phosphoP53 Kit (#9919), anti-cyclinD1 (#2926), anti-FAS (#3189), anti EGFR (#4267), anti-Phospho (tyr1068) EGFR (#2234), anti Met (#4560), anti-Akt (#9272), anti Phospho(Ser473)-Akt (#9271) or anti-Myc (Santa Cruz Technology #Sc-40). Tubulin was detected using anti α-tubulin primary antibody (in-house: the polyclonal Glu-tubulin antibody (L4) is available commercially from Abcys (Paris, France)). HRP-coupled anti-rabbit (#A6154) and anti-mouse (#A4416) secondary antibodies were purchased from Sigma. HRP activity was detected through HRP chemoluminescence detection reagent (Millipore, #WBLUF0100). Apoptotic cell death induction was observed through the observation of PARP cleavage using anti-PARP primary antibodies anti-PARP (46D11) (#9532). Positive control was Epotoside at 50 μM or 100 μM, a known drug inducing cancerous cell death by apoptosis.

Results

The expression level of a panel of known proteins contributing to cancerogenesis (CyclinD1, FAS, cMyc, EGFR, P-EGFR, Met, Akt, P-Akt), protecting humans from cancers (p53) or contributing to Cushing disease (EGFR), was analyzed in order to examine the molecular processes targeted by PCR6236 in the cells.

It was observed that the expression levels of the oncogenic proteins CyclinD1 and FAS strongly decreased in prostatic cancer cells PC-3 and LNCaP, following treatment by PCR6236 in a dose and time dependent manner (FIG. 6). These oncogenic proteins are direct substrates of USP2a which is overexpressed in these prostatic cancer cells. Decreased amount of CyclinD1 and FAS is therefore likely the results of USP2 direct inhibition.

The tumor suppressor p53 prevents cancerogenesis through the regulation of multiple targets and pathways preventing damaged cells proliferation and promoting cancerous cell death by apoptosis. Here, it has been showed that treating cells with PCR6236 restored high levels of p53 expression in a dose dependent manner in both LNCaP and HCT-116 cells (FIG. 7A,B), these two cancerous cell lines displaying reduced level of p53 expression. Moreover, it was repeatedly observed that phosphorylated p53 accumulated in PCR6236 treated cells (FIG. 7B,C). Using specific antibodies against various phosphorylated p53 demonstrated that active P-Ser392- and P-Ser15-p53 in particular, accumulated in LNCaP cells (FIG. 7C). As a consequence of p53 stabilization, treating LNCaP cells with PCR6236 for 24 h induced the cleavage of PARP, which is a direct indicator of apoptotic cell death induction, in a concentration dependent manner (FIG. 8). In addition, a decrease of the p53 regulated oncogenic protein Myc expression level was also observed (FIG. 8). In this assay, the analog PCR9301 displayed a similar activity as PCR6236 in LNCaP cells: i.e., both PCR6236 and PCR9301 induced PARP cleavage, phosphorylation of p53 on Ser15 and cMyc degradation.

USP8 protects EGFR from degradation leading to enhanced MAPK oncogenic signals in cancerous cells as notably illustrated by the phosphorylation and activation of Akt kinase. USP8 is notably a target in lung cancer for overcoming Gefitinib resistance. One mechanism of Gefitinib resistance is the accumulation of other receptor tyrosine kinases such as Met. In non-small cell lung cancers (NSCLC), HCC827 cells, PCR6236 treatment for 6 hours induces EGFR phosphorylation, EGFR and Met degradation; and prevents Akt phosphorylation in a dose dependent manner (FIG. 10). Thus, while EGFR is phosphorylated, this activation is not coupled with the phosphorylation of Akt suggesting that PCR6236 induces EGFR activation is associated with an immediate EGFR degradation bypassing EGFR signaling activity (FIG. 10). In contrast, Gefitinib treatment at 10 μM had no effect on P-EGFR or EGFR levels in these conditions, indicating a different mode of action. This argue in favor of combination therapy or the use of PCR6236 in Gefitinib-resistant cells.

In Cushing's disease, USP8 mutants show constitutive and dominant deubiquitinating activity. Permanent activation of USP8 in corticotroph adenomas is believed to favour EGFR accumulation and recycling back to the plasma membrane resulting in higher ACTH production and secretion compared to wild-type situation. EGFR accumulation was notably observed in HEK293T cell models transfected with the constitutively active USP8 form. Gefitinib, a tyrosine kinase inhibitor targeting the EGFR receptor, has been proposed as a therapeutic drug for suppressing ACTH in corticotroph adenomas. However, in the case of CD that would target a consequence of the genetic mutations in the USP8 gene and not the direct target of the disease (i.e. mutated USP8). We transfected HEK293T cells with a construct encoding a constitutively active mutant of mice USP8 (USP8-S680A, mimicking a pathological form found in human CD)) (obtained from Mizuno et al. Exp Cell Res 2007). As previously reported, expression of this mutant induced enhanced level of EGFR. Treating cells with PCR6236 markedly reduced EGFR levels induced by USP8-S680A (FIG. 11). As observed in lung cancer cells, PCR6236 treatment for 6 hours also induced Met degradation in a dose-dependent manner in HEK293T cells (FIG. 11).

In conclusion PCR6236 treatment of cancerous cells stabilize p53, induce apoptotic cell death and destabilize oncogenic proteins Myc, CyclinD1 and FAS and the receptor tyrosine kinases EGFR and Met, providing molecular explanations for the observed anti-oncogenic and anti-tumorigenic properties of this compound in 2D, 3D cell models or chicken xenograft tumors. Furthermore, degradation of EGFR in cells expressing mutated USP8-S680A indicates that PCR6236 may counteract pathological constitutively active forms of USP8 expressed in pituitary microadenomas of patients with Cushing's disease. USP8, USP2a and other ubiquitin proteases may be targeted by PCR6236 with differential efficacy depending on the cellular context, i.e.: depending on the respective levels of expression of each USP which may contribute to its anti-oncogenic and anti-tumorigenic properties. This feature contributes in particular to its wide anti-oncogenic and anti-tumorigenic properties.

The invention claimed is:
1. A method for the treatment of cancer comprising administration to a subject in need thereof a compound of following formula (I):

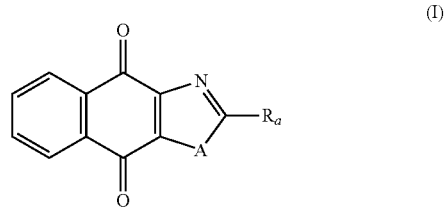

(I)

wherein:
A is selected from the group consisting of:

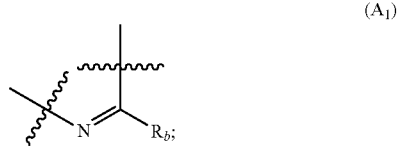

($A_1$)

-continued

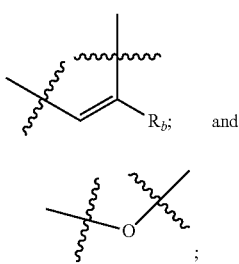
(A₂)

and (A₃)

$R_a$ and $R_b$ each independently represent:
when A is $A_1$ or $A_3$, a group of one of the following formulae:

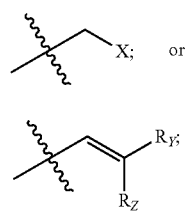
($R_{ab1}$)

or ($R_{ab2}$)

when A is $A_2$, H or a group of one of the following formulae:

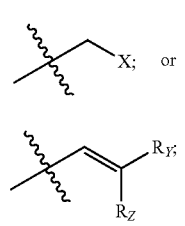
($R_{ab1}$)

or ($R_{ab2}$)

provided that at least one of $R_a$ and $R_b$ is not H;
$R_Y$ and $R_Z$ each independently represent H, a $C_1$-$C_{10}$ linear or branched alkyl group, or a $C_3$-$C_{10}$ cycloalkyl group, or $R_Y$ and $R_Z$ together form with the carbon atom to which they are attached a $C_3$-$C_{10}$ cycloalkyl group;
X represents Cl or a group the following formula:

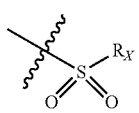
($X_1$)

$R_X$ represents a $C_1$-$C_{10}$ linear or branched alkyl group, a $C_3$-$C_{10}$ cycloalkyl group, an aryl group, or a $C_5$-$C_{10}$-membered heteroaryl;
said $C_1$-$C_{10}$ linear or branched alkyl group, and $C_3$-$C_{10}$ cycloalkyl group being optionally substituted by at least one group selected from:
a $C_3$-$C_{10}$ cycloalkyl group;
a phenyl optionally substituted by at least one group selected from a $C_1$-$C_{10}$ linear or branched alkyl group, a $C_3$-$C_{10}$ cycloalkyl group, an halogen, a —$OR_{ii}$ group, an amine of formula —$NR_{ii}'R_{ii}''$, a nitrile or a nitro group;
a —$OR_i$ group; or
an amine of formula —$NR_i'R_i''$;
said aryl and $C_5$-$C_{10}$-membered heteroaryl being optionally substituted by at least one group selected from:
a $C_1$-$C_{10}$ linear or branched alkyl group;
a $C_3$-$C_{10}$ cycloalkyl group;
a phenyl optionally substituted by at least one group selected from a $C_1$-$C_{10}$ linear or branched alkyl group, a $C_3$-$C_{10}$ cycloalkyl group, an halogen, a —$OR_{ii}$ group, an amine of formula —$NR_{ii}'R_{ii}''$, a nitrile or a nitro group;
an halogen;
a —$OR_i$ group;
an amine of formula —$NR_i'R_i''$;
a nitrile;
a nitro group; or
a $CF_3$ group;
and/or said aryl and $C_5$-$C_{10}$-membered heteroaryl being substituted by two adjacent —$OR_i$ groups that form with the two C atoms bearing said —$OR_i$ groups a 1,4-dioxane ring;
$R_i$ and $R_{ii}$ each independently represent H, a $C_1$-$C_{10}$ linear or branched alkyl group, or a $C_3$-$C_{10}$ cycloalkyl group;
$R_i'$ and $R_i''$ each independently represent H, a $C_1$-$C_{10}$ linear or branched alkyl group, or a $C_3$-$C_{10}$ cycloalkyl group, or $R_i'$ and $R_i''$ together form with the nitrogen atom to which they are attached a $C_4$-$C_7$ heterocycloalkyl group;
$R_{ii}'$ and $R_{ii}''$ each independently represent H, a $C_1$-$C_{10}$ linear or branched alkyl group, or a $C_3$-$C_{10}$ cycloalkyl group, or $R_{ii}'$ and $R_{ii}''$ together form with the nitrogen atom to which they are attached a $C_4$-$C_7$ heterocycloalkyl group,
said cancer being selected from the group consisting of prostate cancer, bladder cancer, breast cancer, lung cancer, colorectal cancer, pituitary adenomas and Cushing's disease.

2. The method according to claim 1, wherein in formula (I):

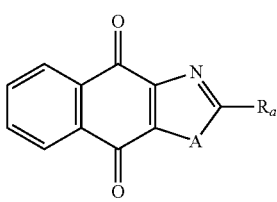
(I)

A is selected from the group consisting of:

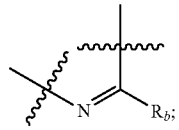
(A₁)

-continued

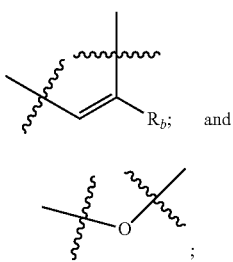
(A$_2$)

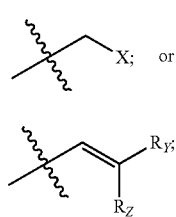
(A$_3$)

R$_a$ and R$_b$ each independently represent:
  when A is A$_1$ or A$_3$, a group of one of the following formulae:

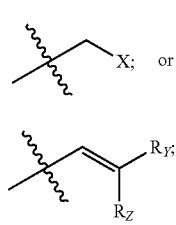
(R$_{ab1}$)

(R$_{ab2}$)

when A is A$_2$, H or a group of one of the following formulae:

(R$_{ab1}$)

(R$_{ab2}$)

provided that at least one of R$_a$ and R$_b$ is not H;
R$_Y$ and R$_Z$ each independently represent H, a C$_1$-C$_{10}$ linear or branched alkyl group, or a C$_3$-C$_{10}$ cycloalkyl group, or R$_Y$ and R$_Z$ together form with the carbon atom to which they are attached a C$_3$-C$_{10}$ cycloalkyl group;
X represents Cl or a group the following formula:

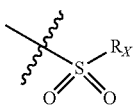
(X$_1$)

R$_X$ represents a C$_1$-C$_{10}$ linear or branched alkyl group, a C$_3$-C$_{10}$ cycloalkyl group, a phenyl group, or a C$_5$-C$_{10}$-membered heteroaryl;
said C$_1$-C$_{10}$ linear or branched alkyl group, and C$_3$-C$_{10}$ cycloalkyl group being optionally substituted by at least one group selected from:
  a C$_3$-C$_{10}$ cycloalkyl group;
  a phenyl optionally substituted by at least one group selected from a C$_1$-C$_{10}$ linear or branched alkyl group, a C$_3$-C$_{10}$ cycloalkyl group, an halogen, a —OR$_{ii}$ group, an amine of formula —NR$_{ii}$'R$_{ii}$", a nitrile or a nitro group;
  a —OR$_i$ group; or
  an amine of formula —NR$_i$'R$_i$";
said phenyl and C$_5$-C$_{10}$-membered heteroaryl being optionally substituted by at least one group selected from:
  a C$_1$-C$_{10}$ linear or branched alkyl group;
  a C$_3$-C$_{10}$ cycloalkyl group;
  a phenyl optionally substituted by at least one group selected from a C$_1$-C$_{10}$ linear or branched alkyl group, a C$_3$-C$_{10}$ cycloalkyl group, an halogen, a —OR$_{ii}$ group, an amine of formula —NR$_{ii}$'R$_{ii}$", a nitrile or a nitro group;
  an halogen;
  a —OR$_i$ group;
  an amine of formula —NR$_i$'R$_i$";
  a nitrile; or
  a nitro group;
R$_i$ and R$_{ii}$ each independently represent H, a C$_1$-C$_{10}$ linear or branched alkyl group, or a C$_3$-C$_{10}$ cycloalkyl group;
R$_i$' and R$_i$" each independently represent H, a C$_1$-C$_{10}$ linear or branched alkyl group, or a C$_3$-C$_{10}$ cycloalkyl group, or R$_i$' and R$_i$" together form with the nitrogen atom to which they are attached a C$_4$-C$_7$ heterocycloalkyl group; and
R$_{ii}$' and R$_{ii}$" each independently represent H, a C$_1$-C$_{10}$ linear or branched alkyl group, or a C$_3$-C$_{10}$ cycloalkyl group, or R$_{ii}$' and R$_{ii}$" together form with the nitrogen atom to which they are attached a C$_4$-C$_7$ heterocycloalkyl group.

3. The method according to claim 1, wherein formula (I) is formula (I$_A$):

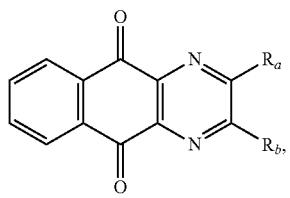
(I$_A$)

and
R$_a$ and R$_b$ are as defined in claim 1.

4. The method according to claim 1, wherein formula (I) is formula (I$_C$):

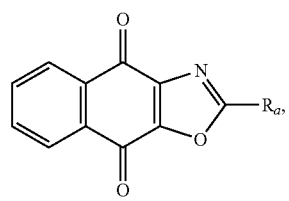
(I$_C$)

and
R$_a$ is as defined in claim 1.

5. The method according to claim 4 wherein R$_a$ represents a group of the following formula:

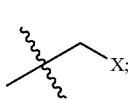

(R$_{ab1}$)

and

X represents a group of the following formula:

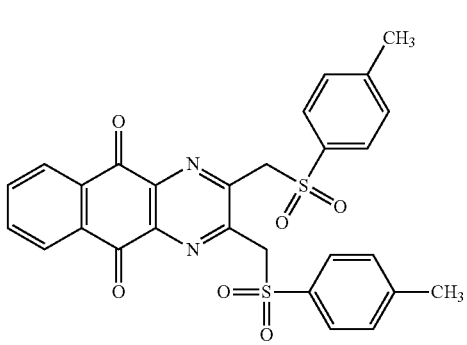

(X$_1$)

6. The method according to claim 1, wherein R$_X$ represents a C$_1$-C$_{10}$ linear or branched alkyl group, a C$_3$-C$_{10}$ cycloalkyl group, an aryl, or a C$_5$-C$_{10}$-membered heteroaryl; said C$_1$-C$_{10}$ linear or branched alkyl group, and C$_3$-C$_{10}$ cycloalkyl group being optionally substituted as defined in claim 1;

said aryl or C$_5$-C$_{10}$-membered heteroaryl being optionally substituted by at least one group selected from:
- a C$_1$-C$_{10}$ linear or branched alkyl group;
- a C$_3$-C$_{10}$ cycloalkyl group;
- a phenyl optionally substituted by at least one group selected from a C$_1$-C$_{10}$ linear or branched alkyl group, a C$_3$-C$_{10}$ cycloalkyl group, an halogen, a —OR$_{ii}$, group, an amine of formula —NR$_{ii}$'R$_{ii}$", a nitrile or a nitro group;
- —F;
- a —OR$_i$ group;
- an amine of formula —NR$_i$'R$_i$";
- a nitrile;
- a nitro group; or
- a CF$_3$ group;

and/or said aryl and C$_5$-C$_{10}$-membered heteroaryl being substituted by two adjacent —OR$_i$ groups that form with the two C atoms bearing said —OR$_i$ groups a 1,4-dioxane ring.

7. The method according to claim 1, wherein the compound is any one of the following formulae:

PCR6236

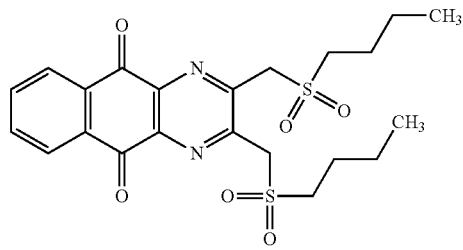

PCR7986

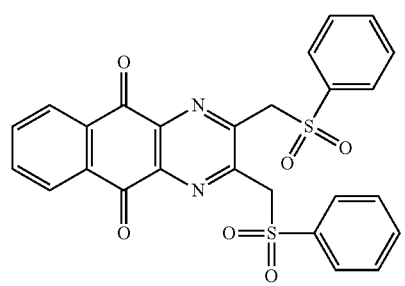

PCR7985

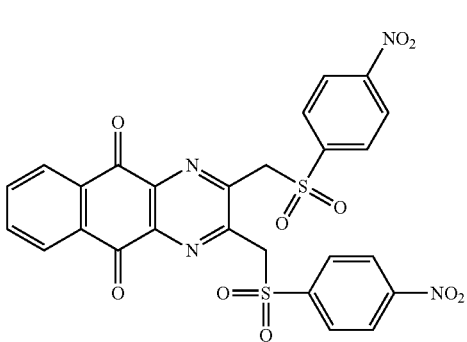

PCR7991

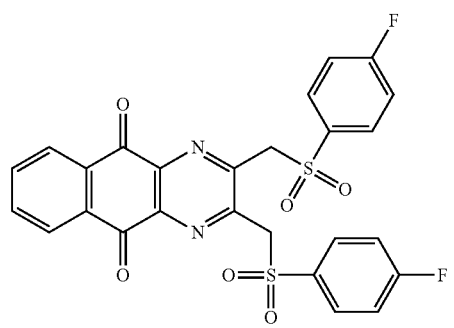

PCR7993

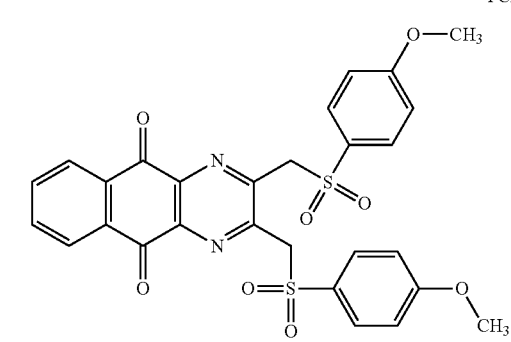

PCR7994

-continued
PCR7996
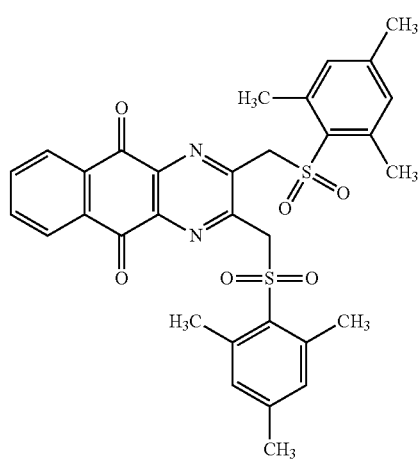
PCR7997
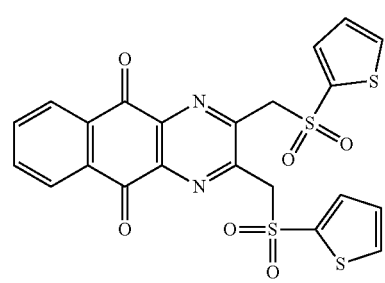
PCR8146
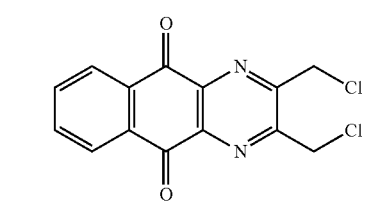
PCR8156
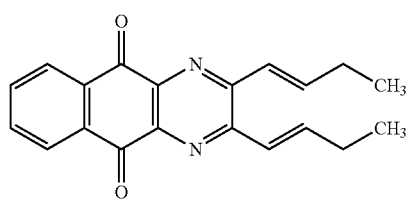
PCR8153
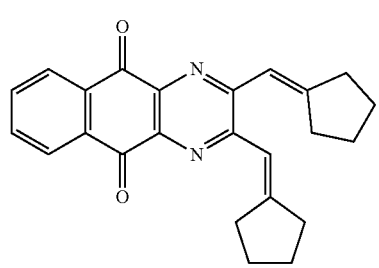
PCR9301
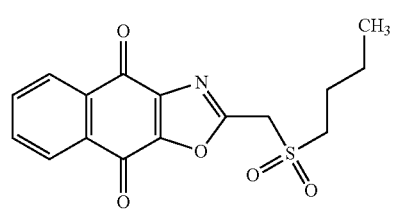 [SMILES: CCCCS(=O)(=O)Cc1nc2c(o1)C(=O)c1ccccc1C2=O]
-continued
OMV1
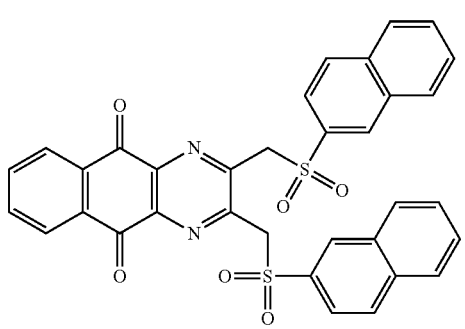
OMV3
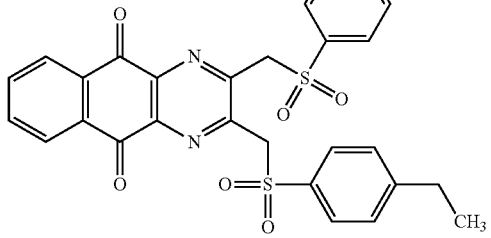
OMV4
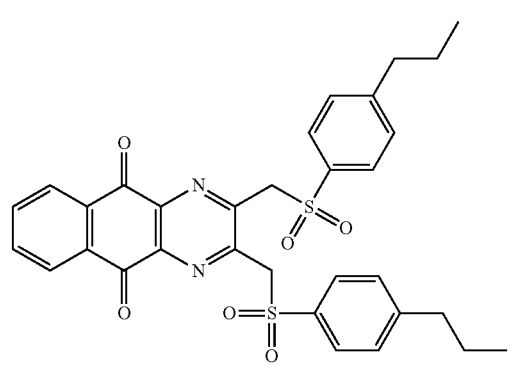
OMV5
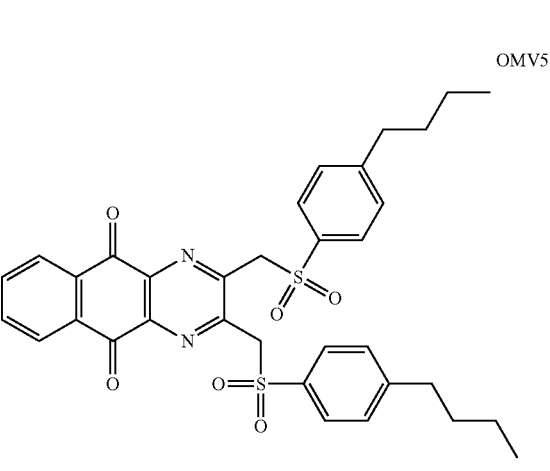

87
-continued
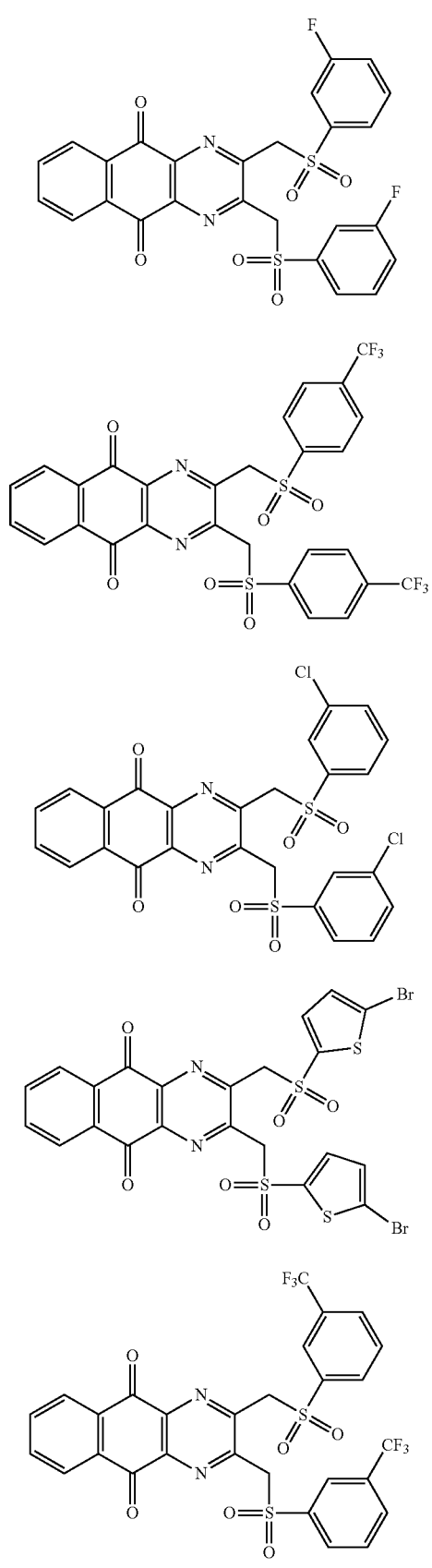
OMV13
OMV14
OMV15
OMV16
OMV17
88
-continued
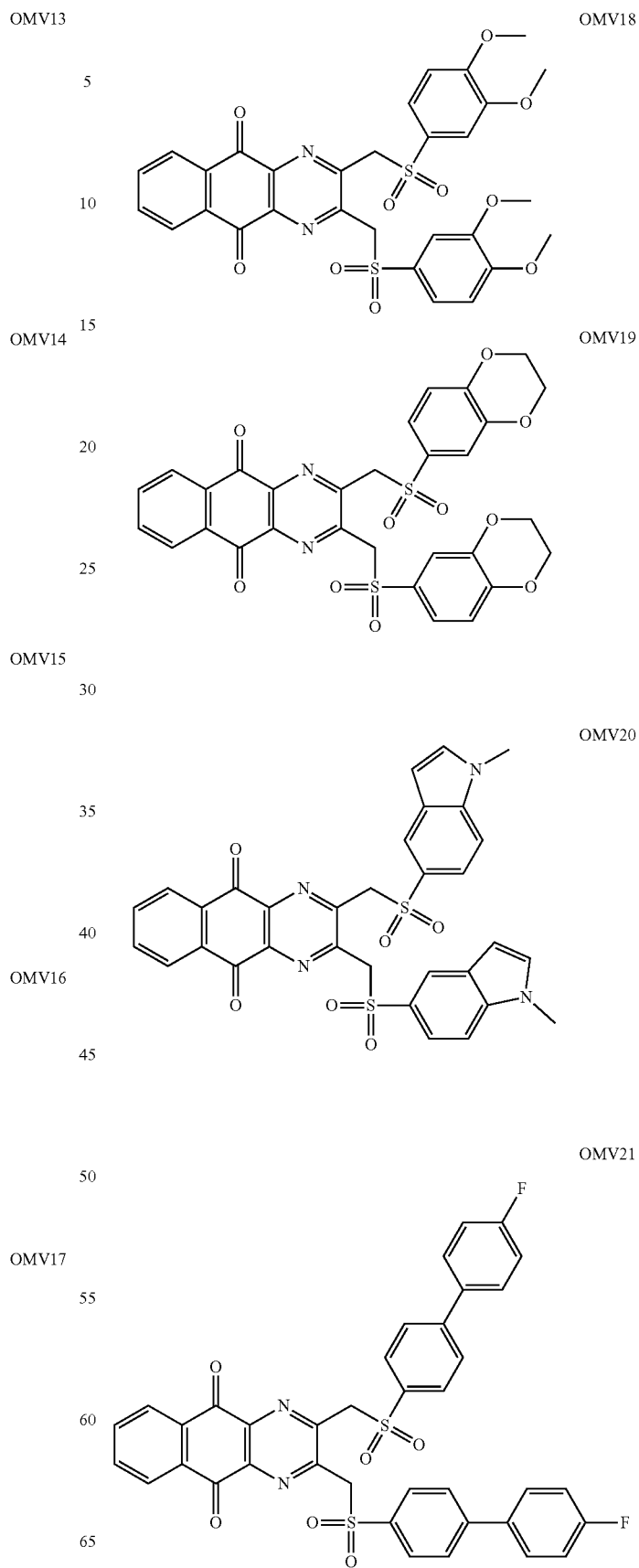
OMV18
OMV19
OMV20
OMV21

OMV23
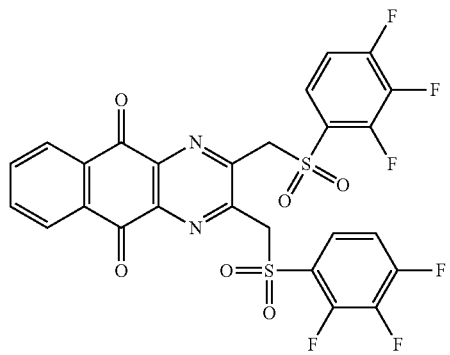

OMV24
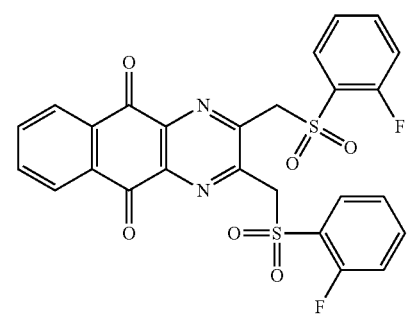

OMV8
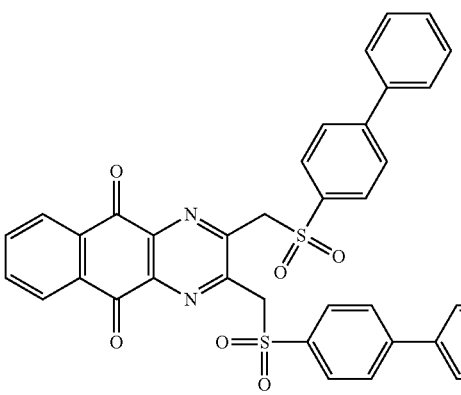

VIN6074
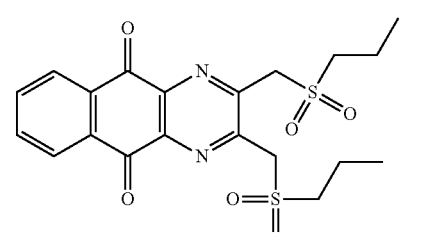

VIN6075
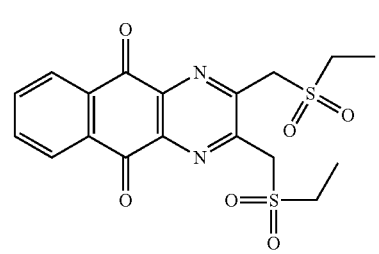

VIN6076
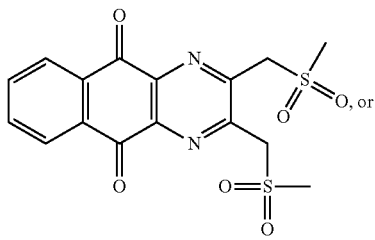

VIN6077
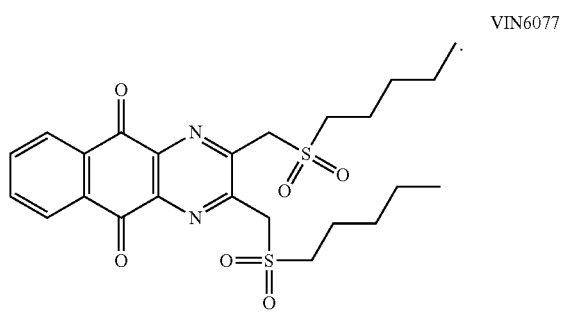

8. The method according to claim 1, wherein the compound is administered in an amount effective to inhibit USP2 and/or USP8.

9. The method according to claim 8, wherein the compound is administered in an amount effective to inhibit USP2, and said cancer being selected from the group consisting of prostate cancer, bladder cancer and breast cancer.

10. The method according to claim 9, wherein the compound is any one of the following formulae:

PCR7986
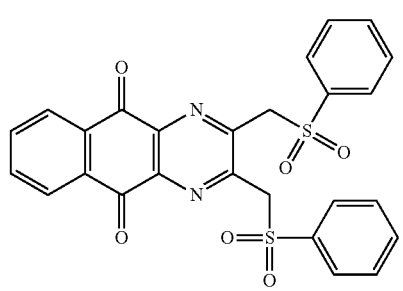

PCR7994
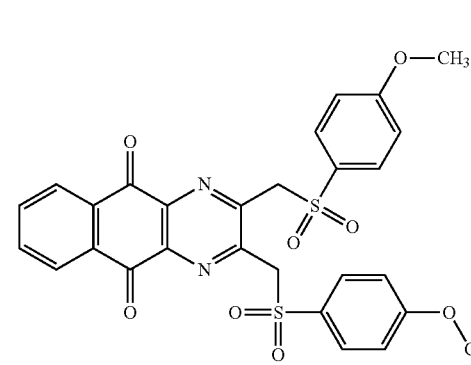

PCR7996
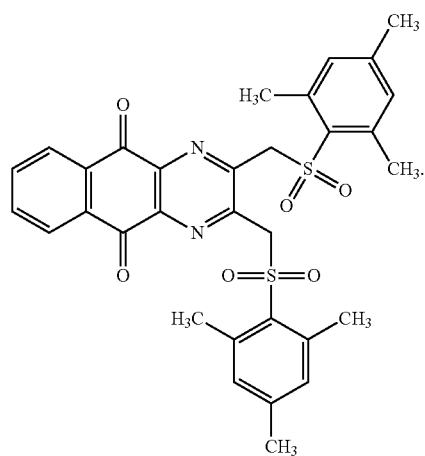
PCR7994
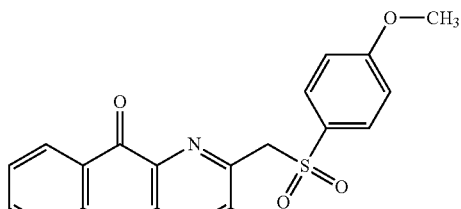
OMV15
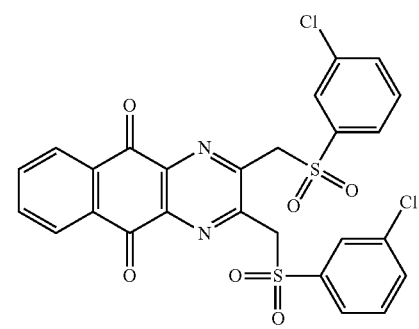
11. The method according to claim 8, by inhibiting USP8, said cancer being selected from the group consisting of lung cancer, pituitary adenomas and Cushing's disease.
12. The method according to claim 11, wherein the compound is any one of the following formulae:
PCR236
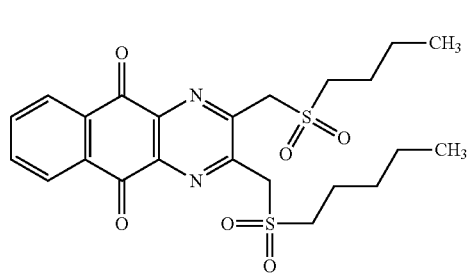
VIN6077
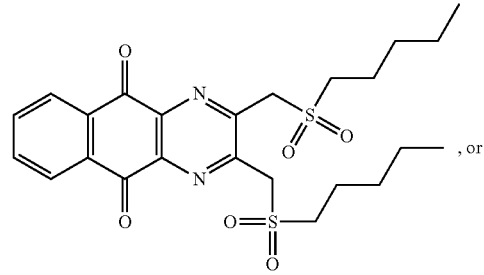
, or
PCR7991
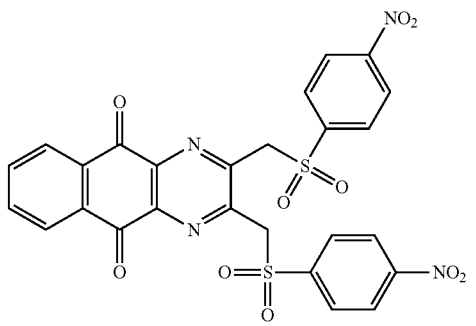
PCR7996
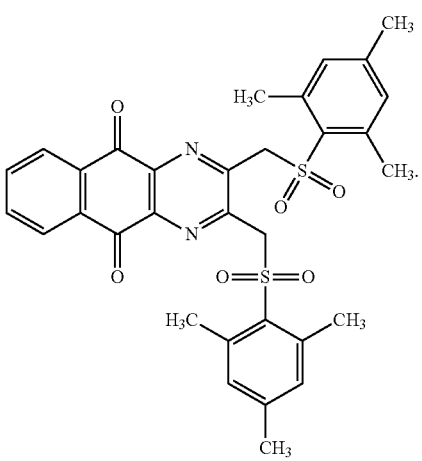
* * * * *